US012690865B2

(12) United States Patent
Batty et al.

(10) Patent No.: US 12,690,865 B2
(45) Date of Patent: Jul. 28, 2026

(54) METHODS OF OPERATING A SURGICAL INSTRUMENT OR A SUBSYSTEM THEREOF

(71) Applicant: CILAG GMBH INTERNATIONAL, Zug (CH)

(72) Inventors: Christopher Batty, Cincinnati, OH (US); Raffaele Definis, Cincinnati, OH (US); Jonathan Von Stein, Cincinnati, OH (US); Christopher Denzinger, Cincinnati, OH (US); David Keilholz, Cincinnati, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 0 days.

(21) Appl. No.: 18/775,023

(22) Filed: Jul. 17, 2024

(65) Prior Publication Data

US 2025/0025164 A1     Jan. 23, 2025

Related U.S. Application Data

(60) Provisional application No. 63/634,201, filed on Apr. 15, 2024, provisional application No. 63/634,171, (Continued)

(51) Int. Cl.
*A61B 17/072*     (2006.01)
*A61B 17/00*     (2006.01)
(Continued)

(52) U.S. Cl.
CPC ........ *A61B 17/072* (2013.01); *A61B 17/0643* (2013.01); *A61B 17/07207* (2013.01); *A61B 34/30* (2016.02); *A61B 2017/00017* (2013.01);

*A61B 2017/00367* (2013.01); *A61B 2017/00398* (2013.01); *A61B 2017/00411* (2013.01); *A61B 2017/00477* (2013.01); (Continued)

(58) Field of Classification Search
CPC .................................................... A61B 17/072
See application file for complete search history.

(56) References Cited

U.S. PATENT DOCUMENTS

| | | | |
|---|---|---|---|
| 8,292,150 B2 | 10/2012 | Bryant | |
| 8,460,275 B2 | 6/2013 | Taylor et al. | |

(Continued)

FOREIGN PATENT DOCUMENTS

| | | |
|---|---|---|
| EP | 2768418 B1 | 7/2017 |
| EP | 2811932 B1 | 6/2019 |

(Continued)

*Primary Examiner* — Daniel Jeremy Leeds
(74) *Attorney, Agent, or Firm* — Troutman Pepper Locke LLP

(57) ABSTRACT

Systems and subsystems for using a robotic instrument are disclosed. The method includes engaging a first closure input puck with a first closure robotic output. The method includes rotating the first closure robotic output to cause the first closure input puck to rotate. The method includes rotating a cam gear via the rotation of the first closure input puck. Rotation of the cam gear causes a yoke pin to track through a cam track in the cam gear, and the yoke pin is coupled to a closure tube. Tracking of the yoke pin through the cam track causes the yoke pin to translate from a first position to a second position, thereby translating the closure tube.

18 Claims, 77 Drawing Sheets

Related U.S. Application Data filed on Apr. 15, 2024, provisional application No. 63/515,001, filed on Jul. 21, 2023, provisional application No. 63/514,972, filed on Jul. 21, 2023.

(51) Int. Cl.

| | |
|---|---|
| *A61B 17/064* | (2006.01) |
| *A61B 17/068* | (2006.01) |
| *A61B 17/29* | (2006.01) |
| *A61B 34/30* | (2016.01) |

(52) U.S. Cl.

CPC .............. *A61B 2017/00831* (2013.01); *A61B 2017/00862* (2013.01); *A61B 17/068* (2013.01); *A61B 17/0686* (2013.01); *A61B 2017/07257* (2013.01); *A61B 2017/07271* (2013.01); *A61B 2017/07285* (2013.01); *A61B 2017/2903* (2013.01); *A61B 2217/007* (2013.01)

(56) References Cited

U.S. PATENT DOCUMENTS

| | | | |
|---|---|---|---|
| 8,800,838 | B2 | 8/2014 | Shelton, IV et al. |
| 9,232,979 | B2 | 1/2016 | Parihar et al. |
| 10,085,748 | B2 | 10/2018 | Morgan et al. |
| 10,143,524 | B2 | 12/2018 | Koch |
| 10,251,716 | B2 | 4/2019 | Overmyer |
| 10,307,215 | B2 | 6/2019 | Swayze |
| 10,327,854 | B2 | 6/2019 | Overmyer |
| 10,376,276 | B2 | 8/2019 | Overmyer |
| 10,433,920 | B2 | 10/2019 | Overmyer |
| 10,542,982 | B2 | 1/2020 | Beckman |
| 10,675,025 | B2 | 6/2020 | Swayze |
| 10,702,349 | B2 | 7/2020 | Overmyer |
| 10,918,385 | B2 | 2/2021 | Overmyer |
| 10,987,177 | B2 | 4/2021 | Overmyer et al. |
| 11,033,344 | B2 | 6/2021 | Overmyer |
| 11,058,477 | B2 | 7/2021 | Messerly et al. |
| 11,191,539 | B2 | 12/2021 | Overmyer |
| 11,191,543 | B2 | 12/2021 | Overmyer |
| 11,191,560 | B2 | 12/2021 | Overmyer |
| 11,219,495 | B2 | 1/2022 | Overmyer et al. |
| 11,419,605 | B2 | 8/2022 | Denzinger |
| 11,419,606 | B2 | 8/2022 | Overmyer |
| 11,439,474 | B2 | 9/2022 | Kallenberger |
| 11,446,098 | B2 | 9/2022 | Swayze |
| 11,471,228 | B2 | 10/2022 | Overmyer |
| 11,547,494 | B2 | 1/2023 | Swayze |
| 11,559,366 | B2 | 1/2023 | Overmyer |
| 11,622,825 | B2 | 4/2023 | Overmyer |
| 11,813,032 | B2 | 11/2023 | Overmyer |
| 11,813,746 | B2 | 11/2023 | Overmyer |
| 11,864,954 | B2 | 1/2024 | Overmyer |
| 12,023,116 | B2 | 7/2024 | Overmyer |
| 12,070,287 | B2 * | 8/2024 | Overmyer .............. B25J 9/0009 |
| 2003/0130677 | A1 | 7/2003 | Whitman et al. |
| 2007/0023476 | A1 | 2/2007 | Whitman et al. |
| 2009/0114699 | A1 | 5/2009 | Viola |
| 2014/0263541 | A1 | 9/2014 | Leimbach et al. |
| 2014/0303645 | A1 | 10/2014 | Morgan et al. |
| 2016/0067001 | A1 | 3/2016 | Parihar et al. |
| 2016/0174976 | A1 | 6/2016 | Morgan et al. |
| 2016/0174978 | A1 | 6/2016 | Overmyer et al. |
| 2016/0213438 | A1 | 7/2016 | Jogasaki et al. |
| 2019/0021752 | A1 | 1/2019 | Boudreaux et al. |
| 2019/0105117 | A1 | 4/2019 | Brisson et al. |
| 2019/0183491 | A1 | 6/2019 | Shelton, IV |
| 2019/0183504 | A1 | 6/2019 | Shelton, IV et al. |
| 2019/0183592 | A1 | 6/2019 | Shelton, IV et al. |
| 2019/0183597 | A1 * | 6/2019 | Shelton, IV ..... A61B 17/07207 |
| 2020/0093489 | A1 | 3/2020 | Parihar et al. |
| 2020/0330120 | A1 | 10/2020 | Koch, Jr. |
| 2020/0375596 | A1 | 12/2020 | Corsetto |
| 2021/0059664 | A1 | 3/2021 | Hensel et al. |
| 2021/0059773 | A1 * | 3/2021 | Overmyer .............. A61B 17/29 |
| 2021/0059777 | A1 | 3/2021 | Overmyer et al. |
| 2021/0346050 | A1 | 11/2021 | Boudreaux et al. |
| 2022/0105638 | A1 | 4/2022 | Zhang et al. |
| 2022/0105639 | A1 | 4/2022 | Zhang et al. |
| 2022/0125538 | A1 | 4/2022 | Overmyer et al. |
| 2022/0192707 | A1 | 6/2022 | Barakat et al. |
| 2022/0346897 | A1 | 11/2022 | Black et al. |
| 2022/0409310 | A1 | 12/2022 | Overmyer |
| 2023/0001579 | A1 | 1/2023 | Overmyer |
| 2023/0181275 | A1 | 6/2023 | Overmyer |
| 2023/0338051 | A1 | 10/2023 | Koch, Jr. |
| 2023/0355338 | A1 | 11/2023 | Overmyer |
| 2024/0081191 | A1 | 3/2024 | Beckman |
| 2024/0271574 | A1 | 8/2024 | Hill et al. |

FOREIGN PATENT DOCUMENTS

| | | | |
|---|---|---|---|
| EP | 2866697 | B1 | 12/2021 |
| KR | 20150100137 | A | 9/2015 |
| WO | 2020212875 | A1 | 10/2020 |
| WO | 2021038360 | A2 | 3/2021 |
| WO | 2022144818 | A1 | 7/2022 |
| WO | 2023225866 | A1 | 11/2023 |

* cited by examiner

836B

112

830B

880A

830F

831

833

880B

METHODS OF OPERATING A SURGICAL INSTRUMENT OR A SUBSYSTEM THEREOF

CROSS REFERENCE TO RELATED APPLICATIONS

The present application claims the benefit of, and priority to, U.S. Provisional Application Ser. No. 63/514,972 filed on Jul. 21, 2023, U.S. Provisional Application Ser. No. 63/515,001 filed on Jul. 21, 2023, U.S. Provisional Application Ser. No. 63/634,201 filed on Apr. 15, 2024, and U.S. Provisional Application Ser. No. 63/634,171 filed on Apr. 15, 2024, the disclosures of which are expressly incorporated herein by reference.

FIELD OF INVENTION

The present disclosure generally relates to systems, devices, and subsystems for cutting and stapling tissue. More specifically, the present disclosure relates to systems, devices, and subsystems for attachments for robotic surgeries.

BACKGROUND

Stapling is a crucial aspect of many surgical procedures, such as gastrointestinal, thoracic, and gynecological surgeries. Robotic surgical systems have gained significant recognition in recent years due to their potential to enhance surgical precision and dexterity. However, the development of a dedicated surgical stapling instrument that integrates seamlessly into the surgical workflow of a multi-purpose robot remains an unmet need for many surgeons.

SUMMARY

It is an object of the present designs to provide devices and methods to meet the above-stated needs. The designs can be for systems, devices, and subsystems for stapling attachments for robotic surgeries. The attachments can have several subsystems that can be independently actuated to provide a specific action, such as closing of an end effector of the stapler, articulation of the end effector, rolling of the end effector, and firing of the staples within the end effector.

The instant disclosure describes a closure subsystem, which can be one of a number of subsystems for a surgical instrument. The closure subsystem includes a first closure input puck engageable with a first closure robotic output. The closure subsystem includes a cam gear rotatably engaged with the first closure input puck. The closure subsystem includes a yoke pin coupled to a closure tube and movable from a first position to a second position in response to a rotation of the cam gear, Movement of the yoke pin from the first position to the second position translates the closure tube distally onto an anvil ramp of an anvil.

The instant disclosure describes a closure subsystem, which can be one of a number of subsystems for a surgical instrument. The closure subsystem includes a cam gear comprising a cam track. The closure subsystem includes a yoke pin coupled to a closure tube and movable from a first position to a second position in response to a rotation of the cam gear, the yoke pin extending into the cam track. The cam track is shaped to provide a non-linear movement profile of the yoke pin and comprises an open position, a high-speed compression region, a high force region, and a constant force region. The high-speed compression region, the high force region, and the constant force region each have different curvatures. The constant force region is shaped such that the yoke pin remains stationary when tracking through the constant force region as the cam gear rotates.

The instant disclosure describes an articulation subsystem, which can be one of a number of subsystems for a surgical instrument. The articulation subsystem includes a rotatable shaft having a longitudinal axis. The articulation subsystem includes a distal channel retainer coupled to an end effector, the distal channel retainer being pivotable about an articulation joint. The articulation subsystem includes a first articulation bushing slidable from a first position to a second position along the longitudinal axis of the rotatable shaft. The articulation subsystem includes an articulation rod extending distally from the first articulation bushing and coupled at a distal end to the distal channel retainer. The articulation subsystem includes a first rack movable with respect to the longitudinal axis of the rotatable shaft. Movement of the first rack with respect to the longitudinal axis imparts an axial force onto the first articulation bushing moving the first articulation bushing from the first position to the second position. Movement of the first articulation bushing from the first position to the second position actuates the articulation rod causing the distal channel retainer to pivot about the articulation joint.

The instant disclosure describes an articulation subsystem, which can be one of a number of subsystems for a surgical instrument. The articulation subsystem includes a rotatable shaft having a longitudinal axis. The articulation subsystem includes an articulation rod extending along the longitudinal axis of the rotatable shaft and being rotationally coupled to the rotatable shaft. The articulation subsystem includes a first articulation bushing slidable from a first position to a second position along the longitudinal axis of the rotatable shaft, the first articulation bushing being rotationally coupled to the rotatable shaft. The articulation subsystem includes a first rack movable with respect to the longitudinal axis of the rotatable shaft, the first rack being rotationally independent of the rotatable shaft and the first articulation bushing. The articulation subsystem includes a first rack gear engaged with the first rack. Rotation of the first rack gear moves the first rack with respect to the longitudinal axis. Movement of the first rack with respect to the longitudinal axis imparts an axial force onto the first articulation bushing moving the first articulation bushing from the first position to the second position.

The instant disclosure describes a roll subsystem, which can be one of a number of subsystems for a surgical instrument. The roll subsystem includes a rotatable shaft. The roll subsystem includes a first roll input puck engageable with a roll robotic output. The roll subsystem includes a worm gear coupled to and rotatable by the first roll input puck. The roll subsystem includes a worm follower coupled to the rotatable shaft. Rotation of the first roll input puck causes the worm gear to rotate the worm follower and thereby roll the rotatable shaft.

The instant disclosure describes a transection subsystem, which can be one of a number of subsystems for a surgical instrument. The transection subsystem includes a rotatable shaft having a lumen. The transection subsystem includes a firing rod extending at least partially through the lumen. The transection subsystem includes a firing rack coupled to a proximal end of the firing rod such that the firing rod is rotationally independent of the firing rack. The transection subsystem includes a firing gear engaged with the firing rack. Rotation of the firing gear moves the firing rack and the firing rod axially.

The instant disclosure describes a housing with a fluid management system, which can be one of a number of subsystems for a surgical instrument. The housing includes a first opening positioned to be engaged with at least a portion of a robotic arm; a second opening positioned proximate a rod extending from within the housing; and a fluid management system positioned within the housing proximate one of the first opening or the second opening, the fluid management system being configured to hold or divert fluid within the housing.

The instant disclosure describes a surgical instrument including a housing. The surgical instrument includes a closure subsystem disposed within the housing, the closure subsystem being engaged with a shaft. The surgical instrument includes an articulation subsystem movable along the shaft and independently of the closure subsystem. The surgical instrument includes a fluid management system positioned between the closure subsystem and the articulation subsystem and in contact with the shaft.

The instant disclosure describes a method. The method includes attaching a surgical instrument to a robotic arm. The method includes rotating a first input puck and a second input puck of the robotic arm until a predetermined threshold force on both the first input puck and the second input puck is detected, the first input puck and the second input puck being in mechanical communication with an articulation subsystem of the surgical instrument. The method includes rotating the first input puck and the second input puck to a predetermined articulation home position.

The instant disclosure describes a method of operating a closure subsystem of a surgical instrument. The method includes engaging a first closure input puck with a first closure robotic output. The method includes rotating the first closure robotic output to cause the first closure input puck to rotate. The method includes rotating a cam gear via the rotation of the first closure input puck. Rotation of the cam gear causes a yoke pin to track through a cam track in the cam gear, the yoke pin being directly or indirectly coupled to a closure tube. Tracking of the yoke pin through the cam track causes the yoke pin to translate from a first position to a second position, thereby translating the closure tube.

Other aspects of the present disclosure will become apparent upon reviewing the following detailed description in conjunction with the accompanying figures. Additional features or manufacturing and use steps can be included as would be appreciated and understood by a person of ordinary skill in the art.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation. It is expected that those of skill in the art can conceive of and combine elements from multiple figures to better suit the needs of the user.

FIG. 5A depicts a surgical instrument with an "outboard" articulation subsystem, according to aspects of the present disclosure. FIG. 5B depicts a surgical instrument with an "inboard" articulation subsystem, according to aspects of the present disclosure.

FIG. 8 shows the closure subsystem in an open configuration, and FIG. 9 shows the closure subsystem in a closed configuration, according to aspects of the present disclosure.

FIG. 14 shows the articulation subsystem at 0° degrees of articulation, and FIG. 15 shows the articulation subsystem fully articulated in one direction.

FIG. 22 shows the end effector articulated right, FIG. 23 shows the end effector unarticulated (i.e., straight), and FIG. 24 shows the end effector articulated left.

FIG. 26 is a perspective view of the components of the roll subsystem, and FIG. 27 is a cross-sectional view of the components of the roll subsystem.

FIG. 28 shows the roll subsystem a first end position of roll, FIG. 29 shows the roll subsystem an intermediate position of roll, and FIG. 30 shows the roll subsystem a second end position of roll.

FIG. 31A is a perspective view of the components of the roll subsystem, and FIG. 31B is a top, cross-sectional view of the components of the roll subsystem.

FIG. 32A shows an example of a shaft with two flat sections (or "flats"), FIG. 32B shows an example of a shaft with a keyway and a worm follower with a corresponding key feature, FIG. 32C shows an example of a shaft with a keyway and a worm follower with a corresponding key feature, and FIG. 32D shows an example of a shaft and a worm follower with corresponding steps or ledges.

FIG. 33A is a side cross sectional view thereof, and FIG. 33B is cross sectional view from the direction indicated in FIG. 33A.

FIG. 35 shows the transection subsystem in home position, FIG. 36 shows the transection subsystem in a first firing position, and FIG. 37 shows the transection subsystem in a second firing position.

FIG. 54A shows a manual knife return key inside the compartment, FIG. 54B shows the manual knife return key removed from the compartment, and FIG. 54C shows the manual knife return key attached to a key receiver.

FIG. 56A-56C show features to control fluid egress from a housing, according to aspects of the present disclosure. FIG. 56A shows fluid management cavities surrounded by walls, and FIG. 56B shows absorbent materials positioned inside cavities.

DETAILED DESCRIPTION

Specific examples of the present invention are now described in detail with reference to the Figures, where identical reference numbers indicate elements which are functionally similar or identical. The examples address many of the deficiencies associated with prior robotic attachment systems, for instance prior systems that did not provide integrated capabilities to close, articulate, roll, and fire, all with the actuation of their designated robotic outputs. The present surgical instrument includes a housing that contains the gearing and other components necessary to effect the close, articulate, roll, and fire features. In particular, the present disclosure provides a detailed discussion of the closure subsystem, articulation subsystem, roll subsystem, and transection subsystem that are usable to close, articulate, roll, and fire an end effector of the device. Use of the term "fire" throughout this disclosure means to advance the distal portions of the transection subsystem distally. "Firing" the components shall be understood to mean acts to cut, staple, or both.

Overview

Figure 1:
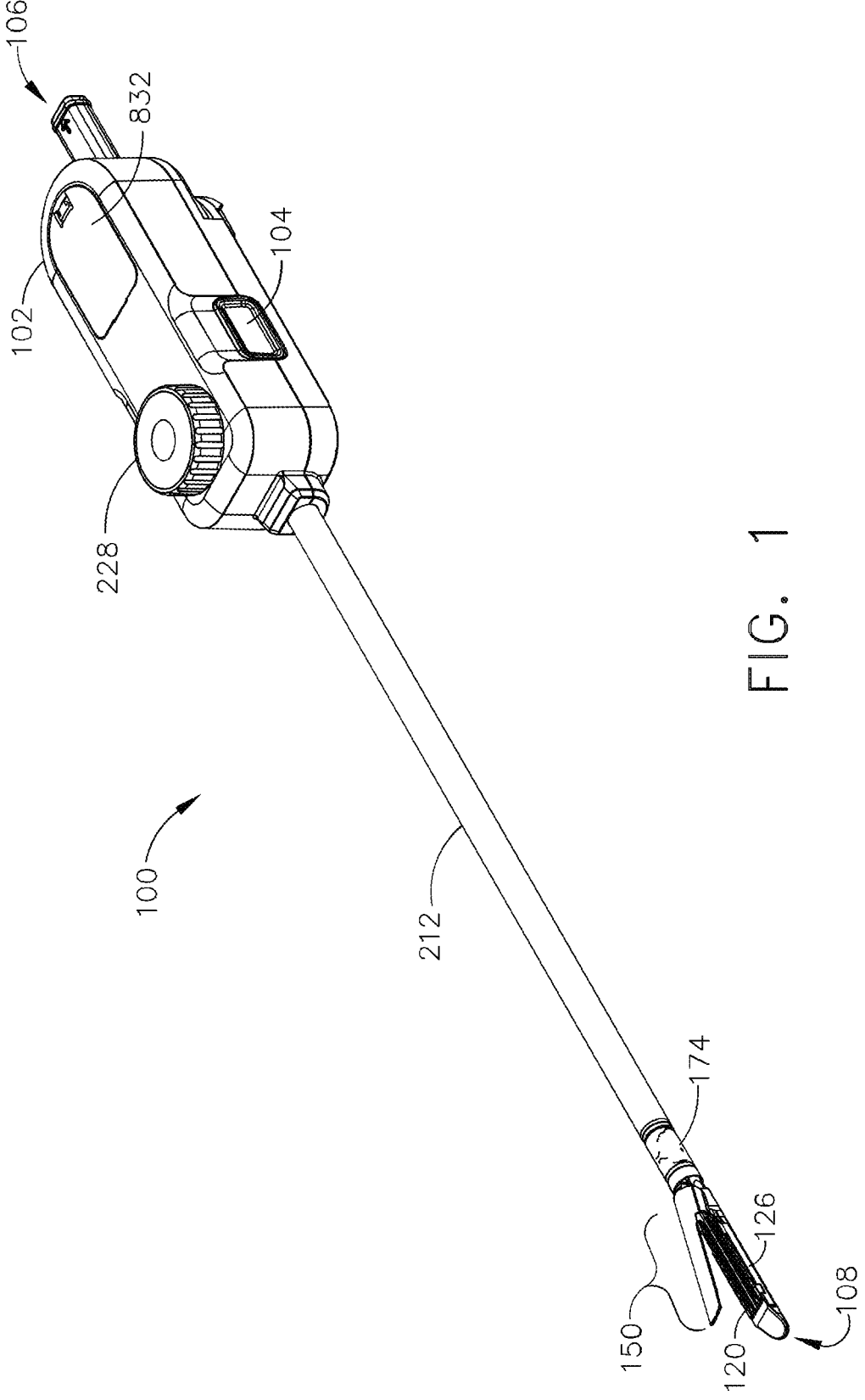
FIG. 1 shows a surgical instrument, according to aspects of the present disclosure.

Turning to the figures, FIG. 1 is a perspective view illustrating a surgical instrument 100, according to aspects of the present disclosure. A housing 102 of the surgical instrument 100 can be attachable to a robotic arm that includes a plurality of outputs, or rotatable disks, that can actuate pucks, or other disks, on the surgical instrument 100. The proximal end 106 of the surgical instrument 100 is therefore attachable to the multi-use robot, and the distal end 108 of the surgical instrument 100 effects the transection and stapling of patient tissue. The surgical instrument can include a release button 104 that allow the device to be detached from the robotic arm. As shown, the surgical instrument 100 can include more than one release buttons 104.

Figure 2:
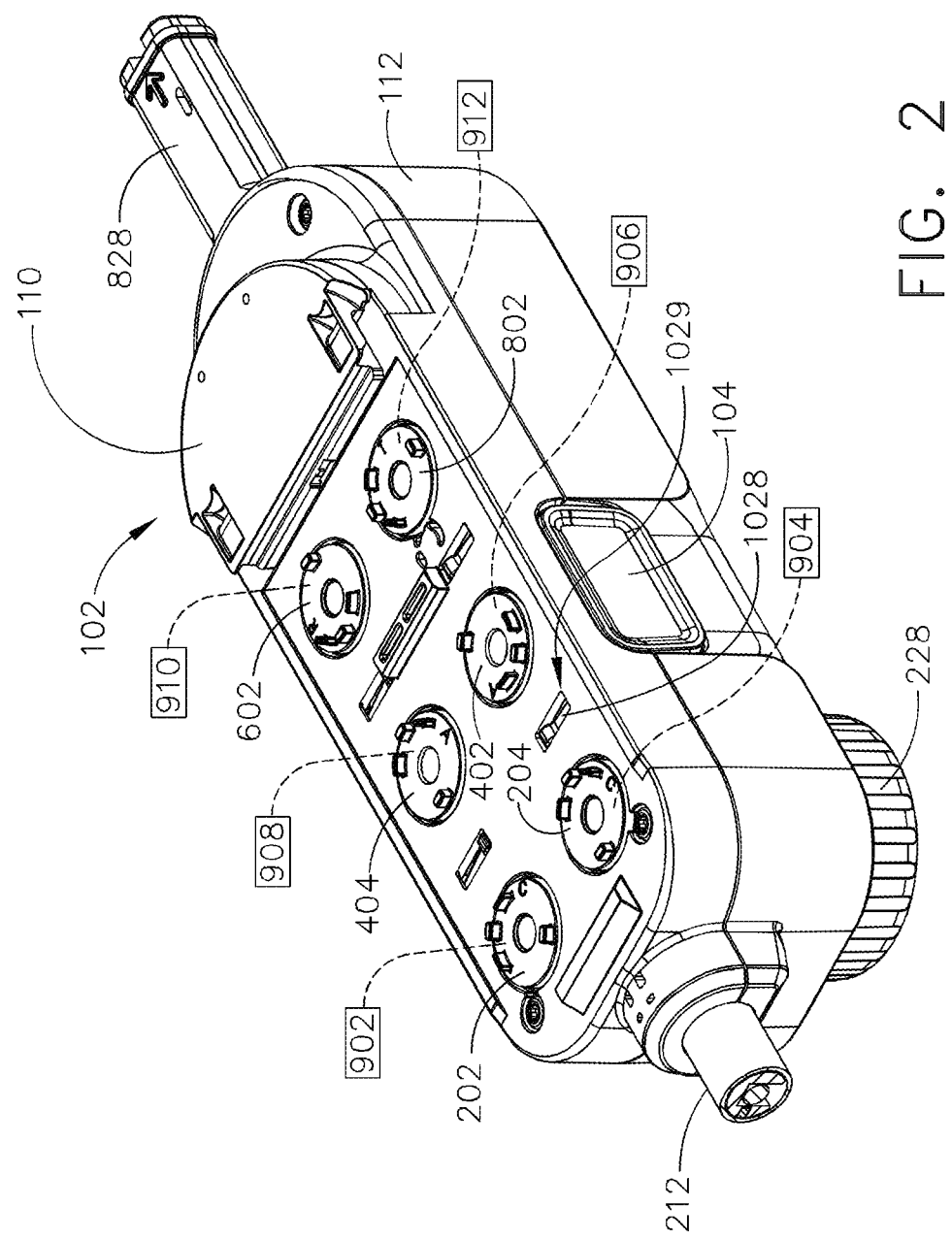
FIG. 2 shows a housing at a proximal end of a surgical instrument, according to aspects of the present disclosure.
Figure 3:
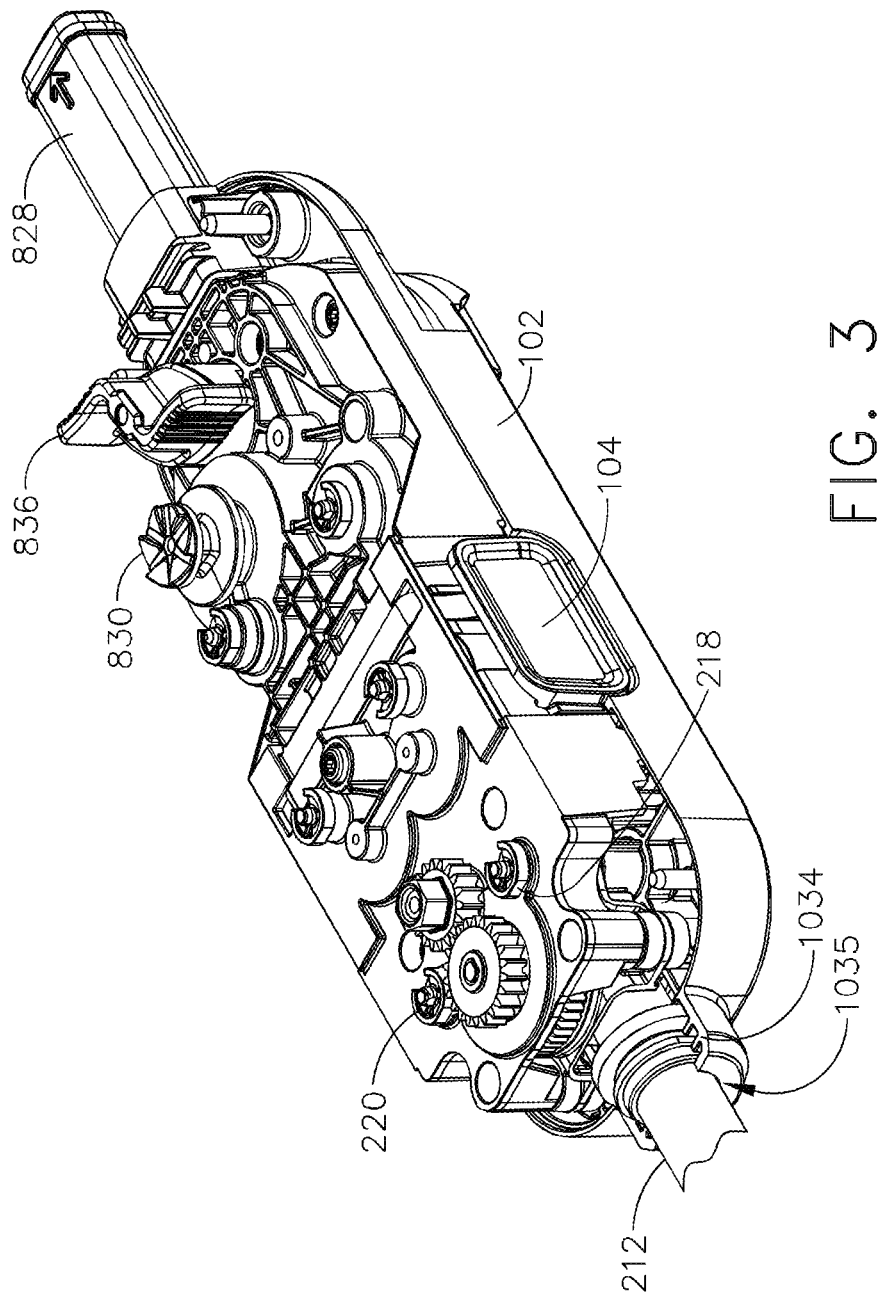
FIGS. 3 and 4 show internal components of a housing at a proximal end of a surgical instrument, according to aspects of the present disclosure.
Figure 4:
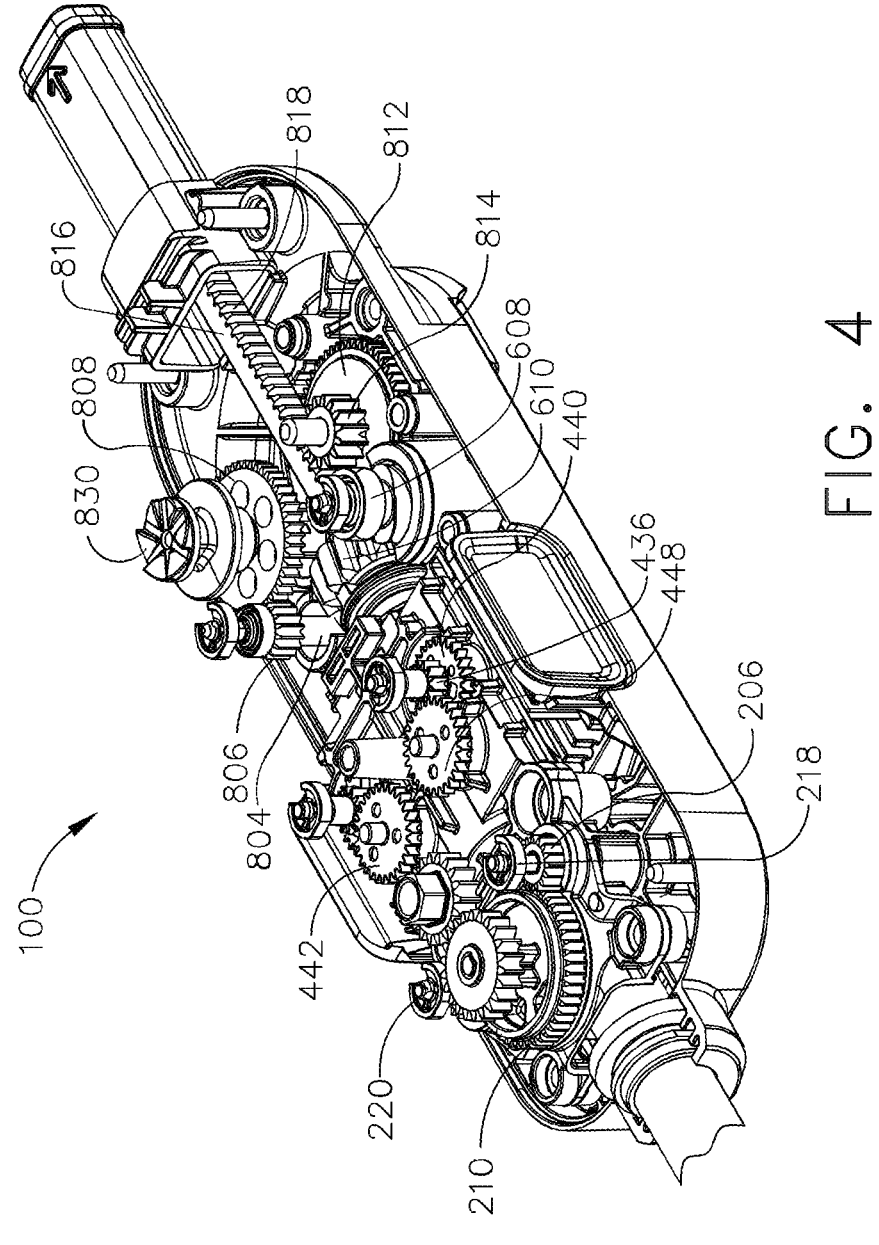

FIG. 2 is a perspective view of the housing 102 as shown from the opposite side from what is shown in FIG. 1. The housing 102 can include a first portion 110 and a second portion 112. The housing 102 includes a series of pucks (e.g., first closure input puck 202, second closure input puck 204, first articulation input puck 402, second articulation input puck 404, roll input puck 602, and transection input puck 802). The pucks can have features that enable them to engage with the rotating features of the robotic arm, such that rotation of the pucks can actuate the gears and other components of the closure subsystem 200, articulation subsystem 400, roll subsystem 600, and transection subsystem 800 described herein. FIGS. 3 and 4 show internal components of the housing 102 at the proximal end 106 of the surgical instrument 100. More detail about features of the housing 102 is provided below, particularly with respect to FIGS. 56A-63B.

Figure 5A:
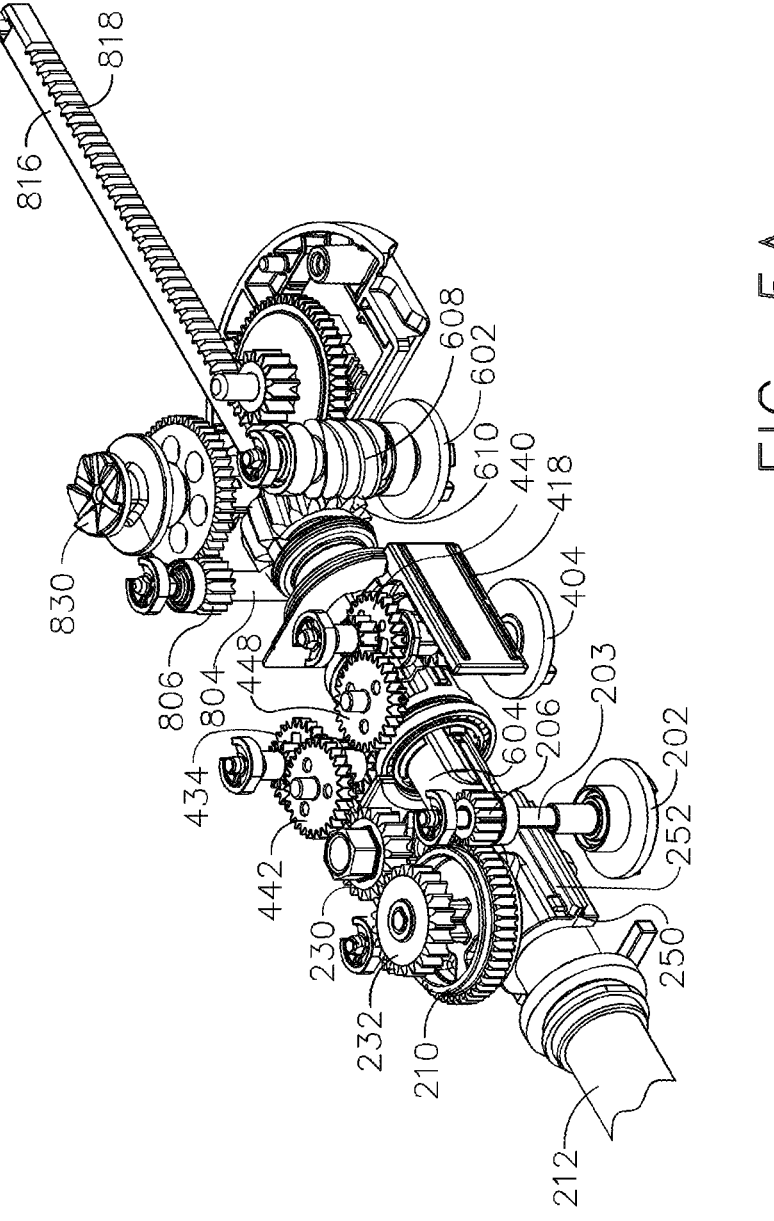
FIGS. 5A and 5B show internal components of a surgical instrument shown without an outer housing, according to aspects of the present disclosure.
Figure 5B:
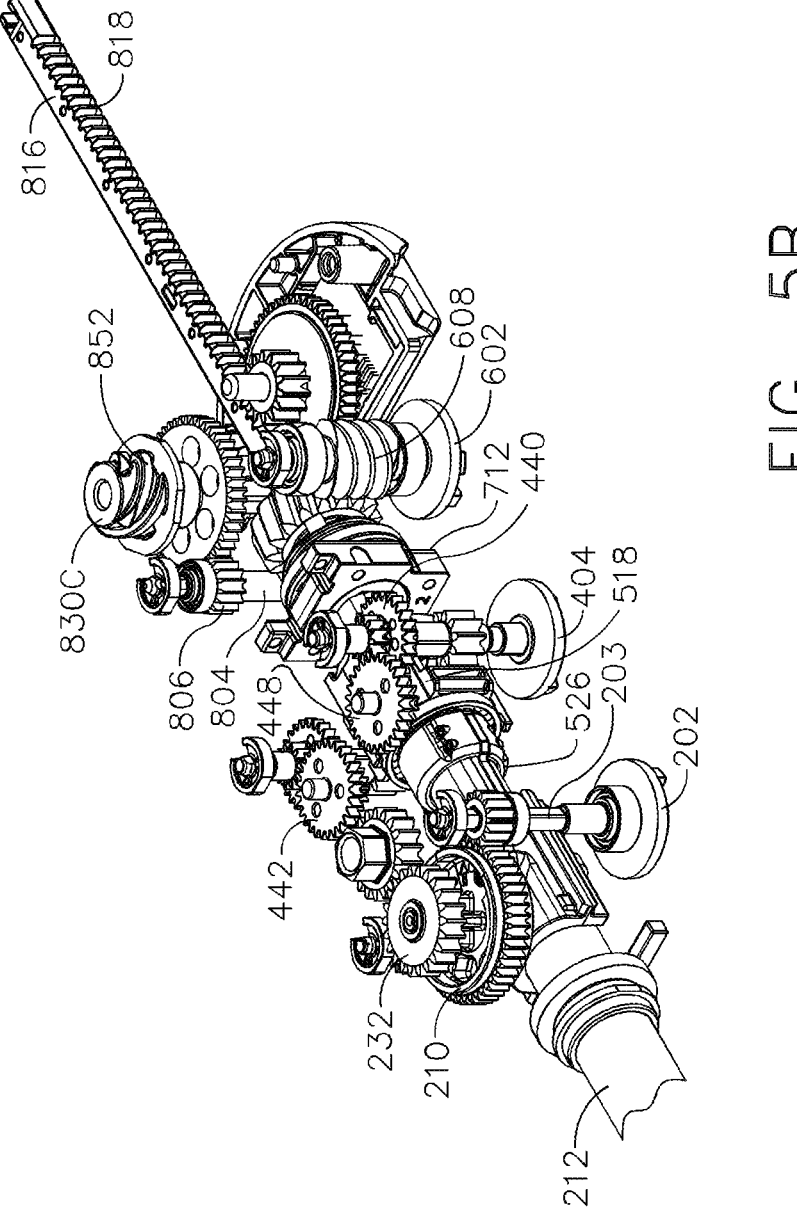
Figure 6A:
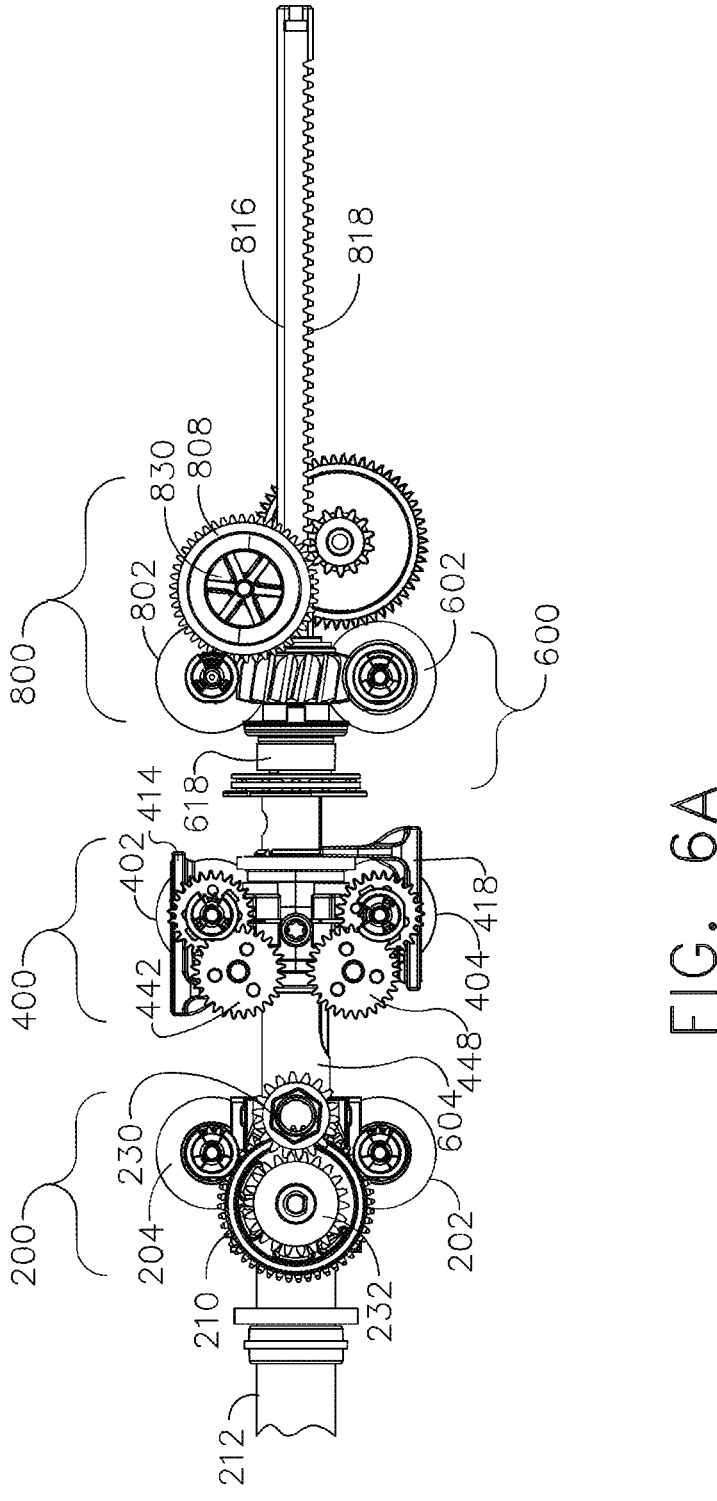
FIG. 6A is a top plan view of the features shown in FIG. 5A.
Figure 6B:
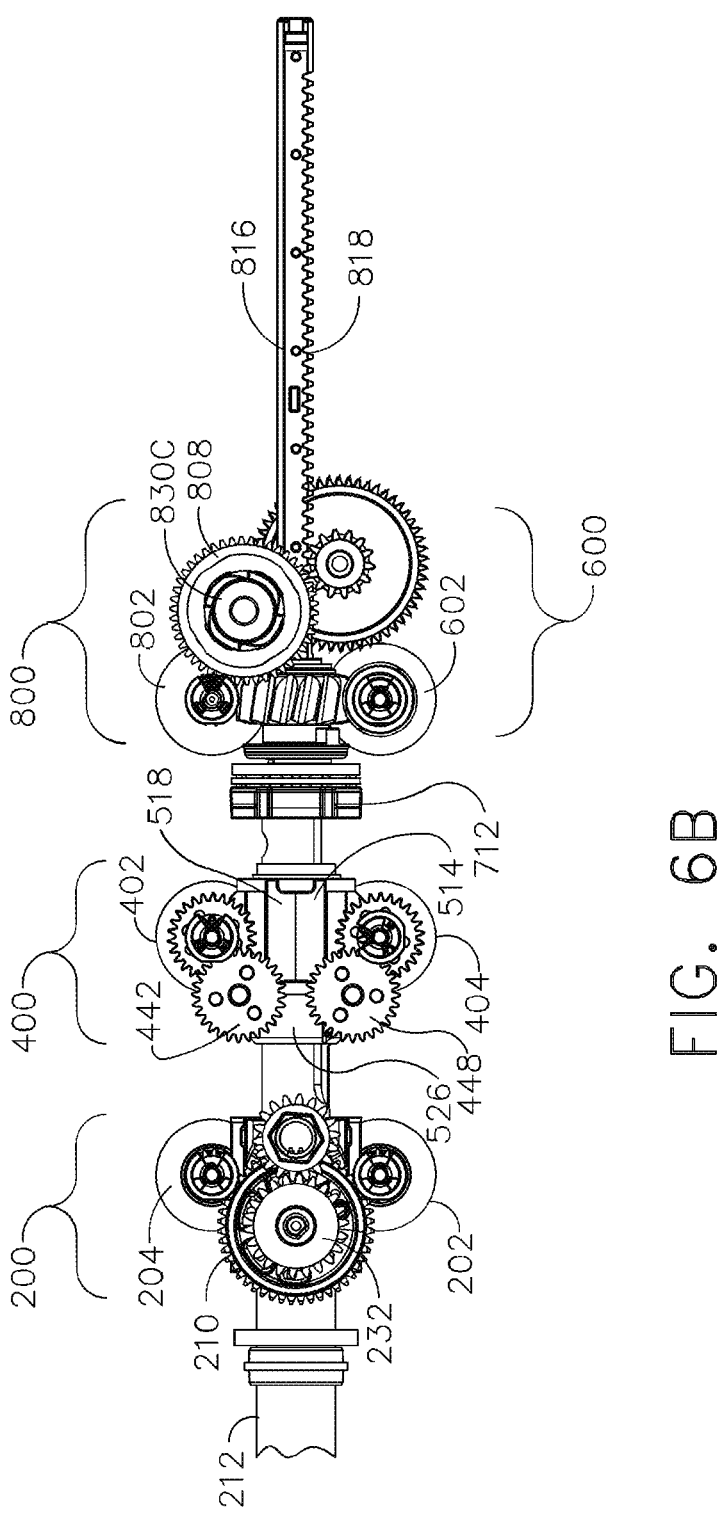
FIG. 6B is a top plan view of the features of FIG. 5B.
Figure 50:
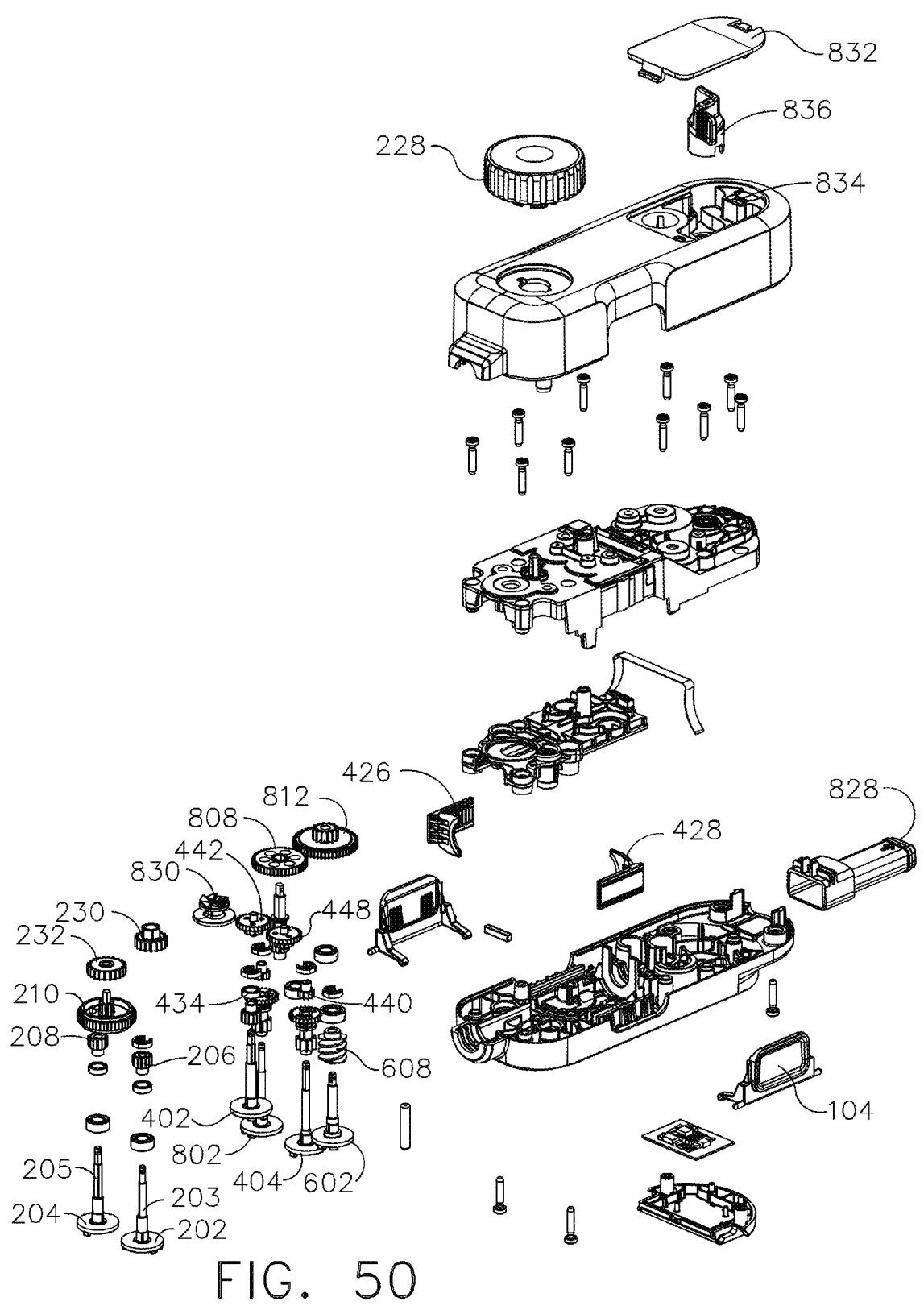
FIG. 50 is an exploded view of the components within a proximal end of a surgical instrument, according to aspects of the present disclosure.
Figure 51:
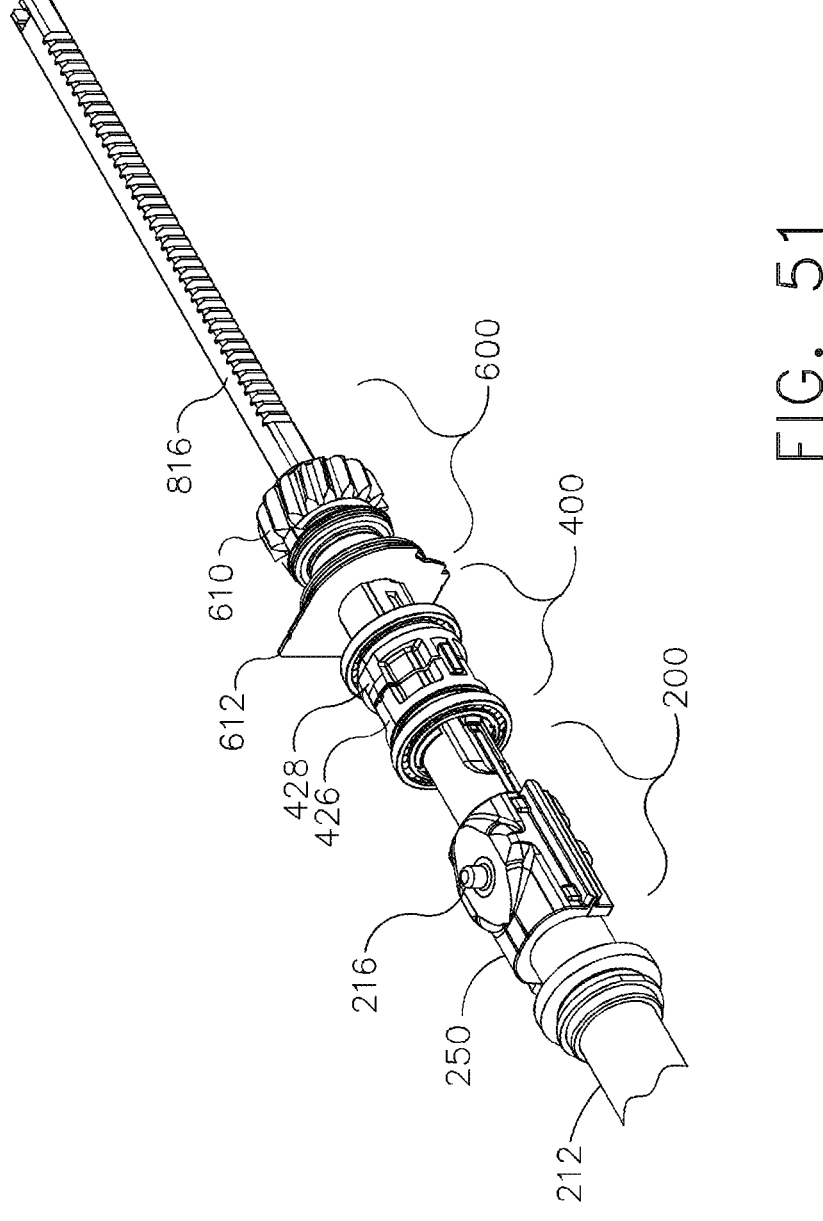
FIG. 51 shows a proximal end of components of a closure subsystem, an articulation subsystem, and a roll subsystem of a surgical instrument, according to aspects of the present disclosure.

FIG. 5A shows internal components of the surgical instrument 100 shown without an outer housing 102, according to aspects of the present disclosure. FIG. 6A is a top plan view of the features shown in FIG. 5A. FIG. 5B depicts a surgical instrument 100 with an "inboard" articulation subsystem, which is described in greater detail below (FIG. 6B is a top plan view of the features of FIG. 5B). The views highlight the different subsystems of the internal components, showing how the closure subsystem 200 and the articulation subsystem 400 each utilize two different pucks (e.g., first closure input puck 202, second closure input puck 204, first articulation input puck 402, and second articulation input puck 404) for their respective actions, whereas the roll subsystem 600 and transection subsystem 800 each utilize only one puck (e.g., roll input puck 602 and transection input puck 802) for their respective actions. As will be described below, alternative embodiments implement the different subsystems with a different number of inputs (i.e., how many pucks are turned to effect their action). There are certain benefits to the closure subsystem 200 and the articulation subsystem 400 utilizing two different pucks, including but not limited to providing additional force for closure and providing antagonistic compression of the bushings for the articulation subsystem 400. FIG. 5A depicts a surgical instrument with an "outboard" articulation subsystem 400. FIG. 5B depicts a surgical instrument with an "inboard" articulation subsystem 400. The differences between an inboard and outboard system are described in greater detail below. FIG. 51 shows the closure subsystem 200, articulation subsystem 400 (outboard version), roll subsystem 600, and transection subsystem 800 without gearing for case of view. FIG. 50 is a fully exploded view of the components within a proximal end 106 of the surgical instrument 100.

Figure 39:
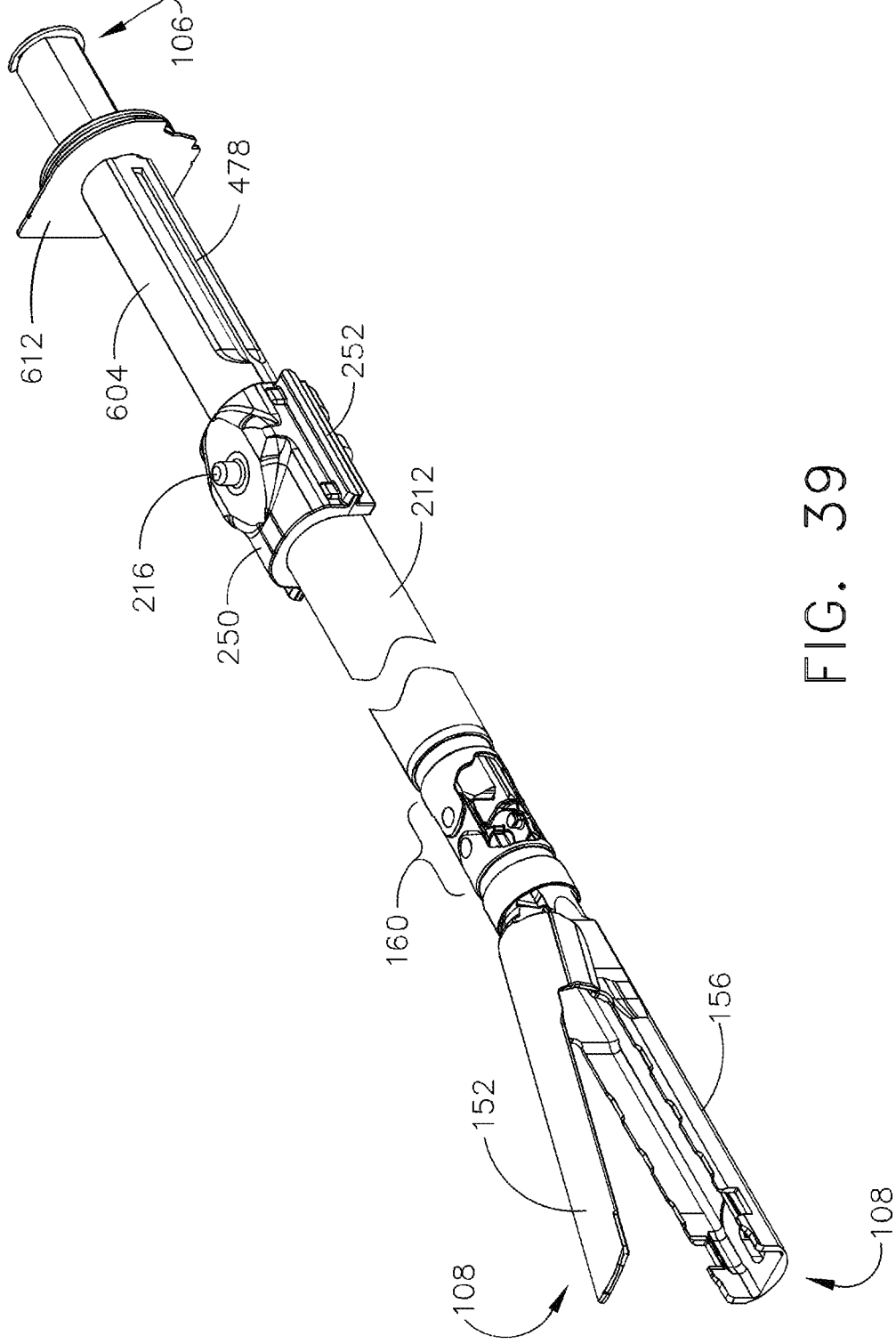
FIG. 39 shows shaft closure components with an anvil in an open position.
Figure 44:
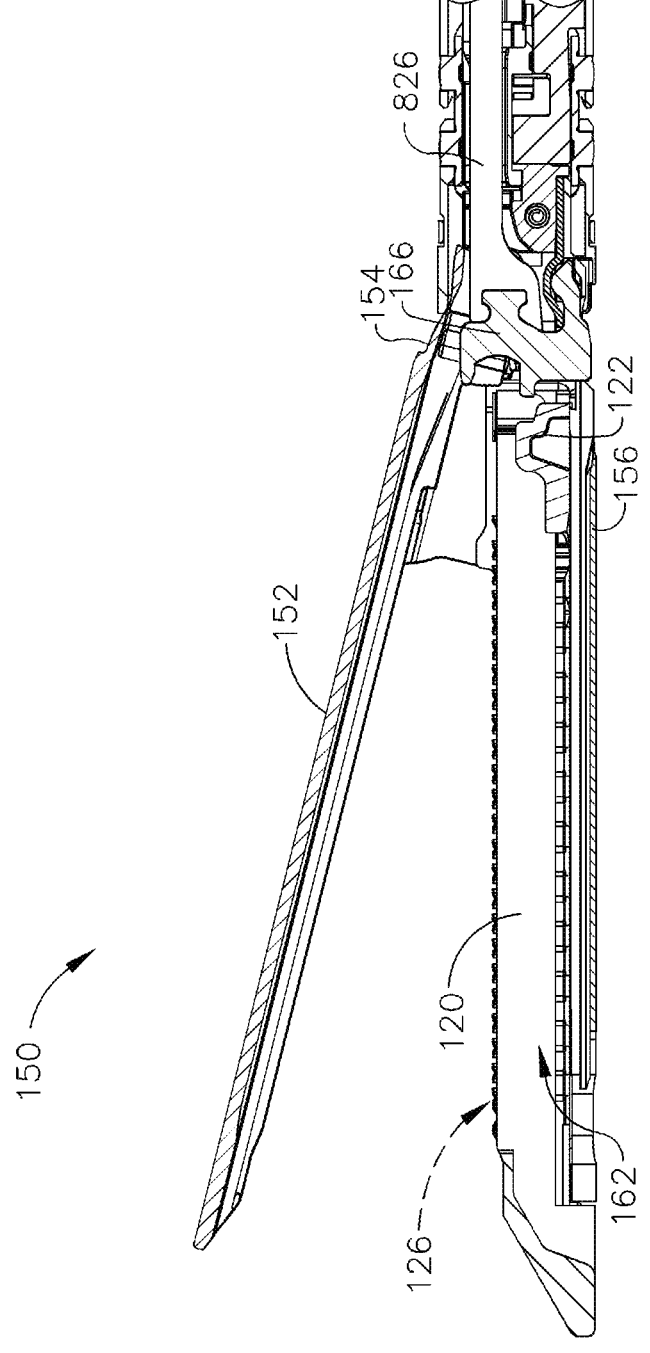
FIG. 44 is a cross-sectional view of an end effector portion of a surgical instrument, according to aspects of the present disclosure. The end effector is in an open configuration.
Figure 45:
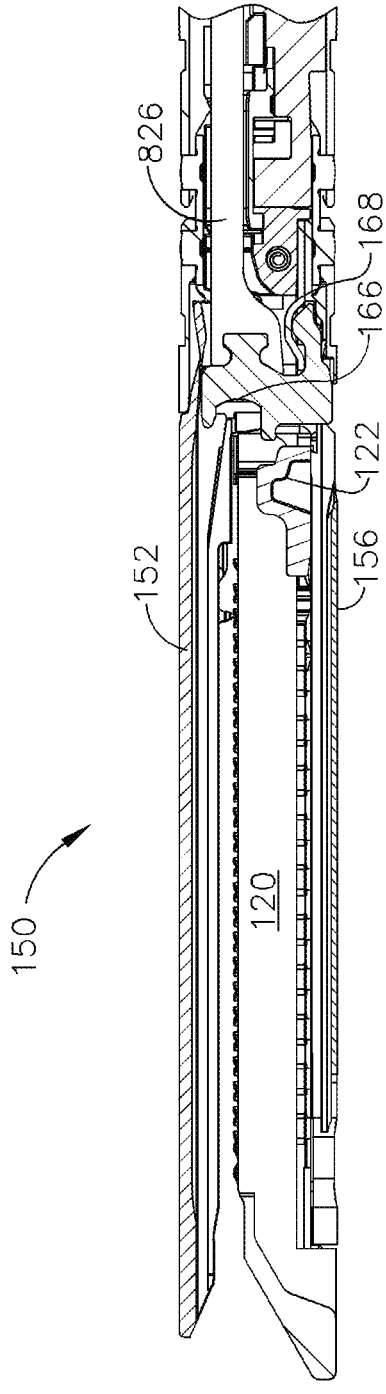
FIG. 45 is a cross-sectional view of an end effector portion of a surgical instrument, according to aspects of the present disclosure. The end effector is in a closed configuration.
Figure 46:
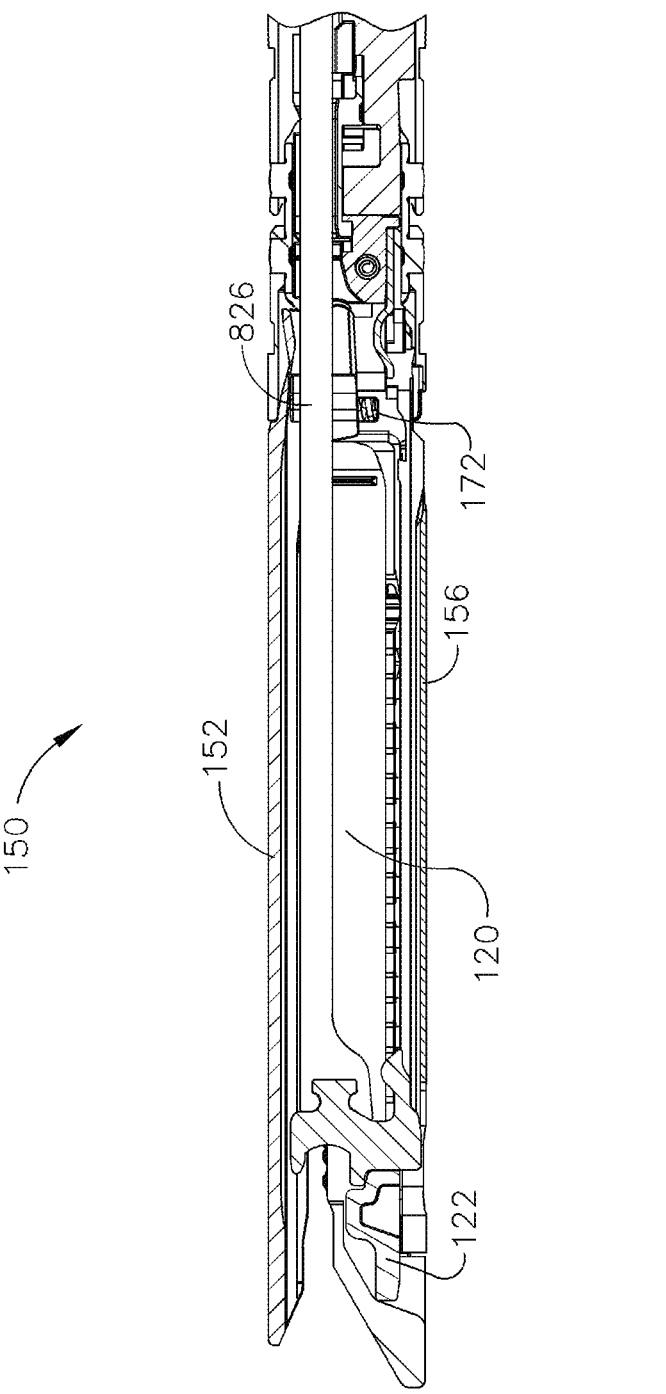
FIG. 46 is a cross-sectional view of an end effector portion of a surgical instrument, according to aspects of the present disclosure. Staples in the cartridge of the end effector have been fired in the view (although staples are not pictured), and the sled of the cartridge is positioned distal within the cartridge.

As shown in FIGS. 1 and 39, for example, the surgical instrument 100 includes an end effector 150 disposed at the distal end 108 of the surgical instrument 100. As shown, the end effector 150 includes an anvil 152 and a channel 156. As will be described in greater detail herein, the anvil 152 can be caused to move with respect to the channel 156 to open and close the end effector 150. Furthermore, as will be described in greater detail herein, the surgical instrument 100 can include a closure ring 226 and a closure tube 212 that can be actuated to cause the anvil 152 to close with respect to the channel 156. The anvil 152 can be opened by retracting the closure ring 226 from the anvil 152. The end effector 150 of the disclosed technology can be configured for cutting and stapling of tissue of a patient. FIG. 45 further illustrates an end effector 150 in a closed configuration while FIG. 44 illustrates an end effector 150 in an open configuration. The anvil 152 of the end effector 150 can be opened and closed by operation of a closure ring 226 that is coupled to the anvil 152 and can be slid proximally and distally by the closure tube 212. As the closure ring 226 is slid distally the closure ring 226 causes the anvil 152 to close. The closure subsystem 200 can close the anvil 152 by moving the closure ring 226 distally and over the anvil ramp 154, thereby hinging the anvil 152 closed. As the closure ring 226 is slid proximally, the closure ring 226 slides away from the anvil 152, allowing it to open. The anvil 152 can be biased in an open configuration (see FIG. 44) with a series of springs 172 (see FIG. 46) within the end effector 150. The closure ring 226 can be caused to move between the opened and closed position by actuation of the closure tube 212. As the closure tube 212 is slid proximally and distally, the closure tube 212, which is engaged with the closure ring 226, causes the closure ring 226 to also slide proximally and distally, thereby opening and closing the anvil 152.

The closure tube 212 can be actuated by movement of a closure yoke 250 between an open position in which the anvil 152 is opened and a closed position in which the anvil 152 is closed. The closure yoke 250 can slide axially in a proximal direction to open the anvil 152 and slide axially in a distal direction to cause the anvil 152 to close. In other words, when the closure yoke 250 is in the open position it will be more proximal, and when the closure yoke 250 is in the closed position it will be more distal. As will be described in greater detail herein, the closure yoke 250 can be transitioned between the open and closed positions by actuation of several gears.

Closure Subsystem

Figure 7A:
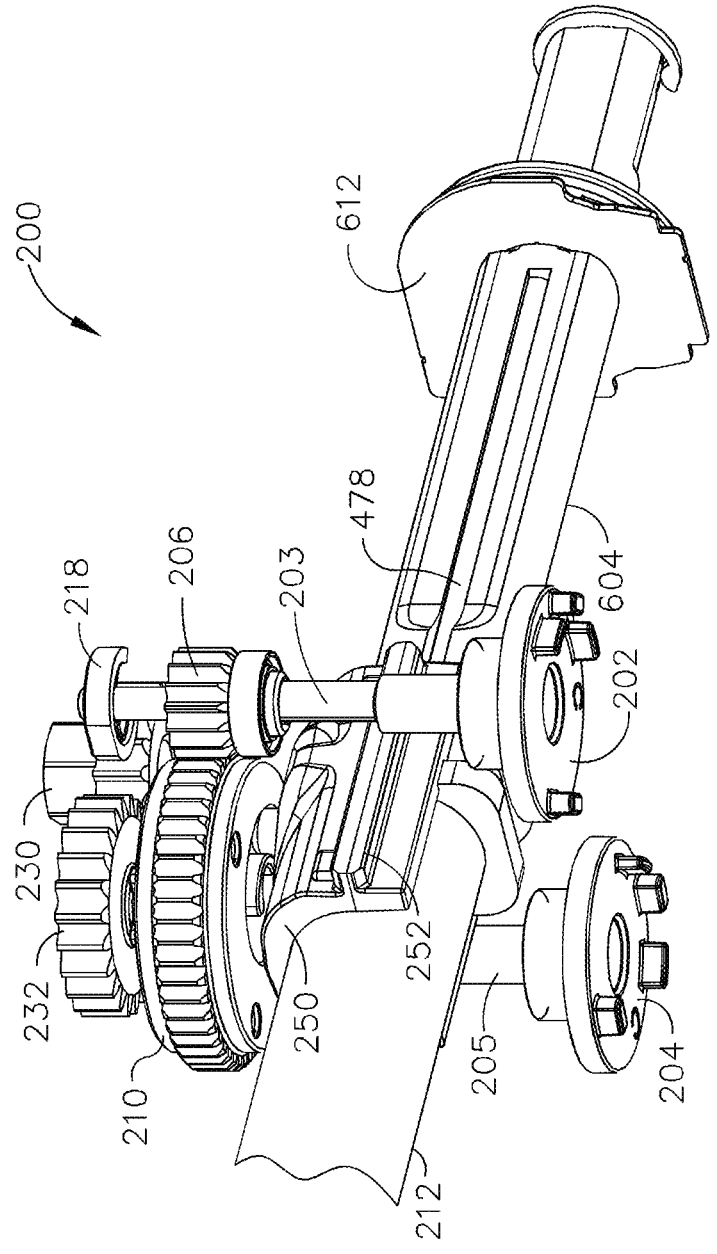
FIG. 7A shows a side perspective view of a closure subsystem, according to aspects of the present disclosure.
Figures 7B, 7C:
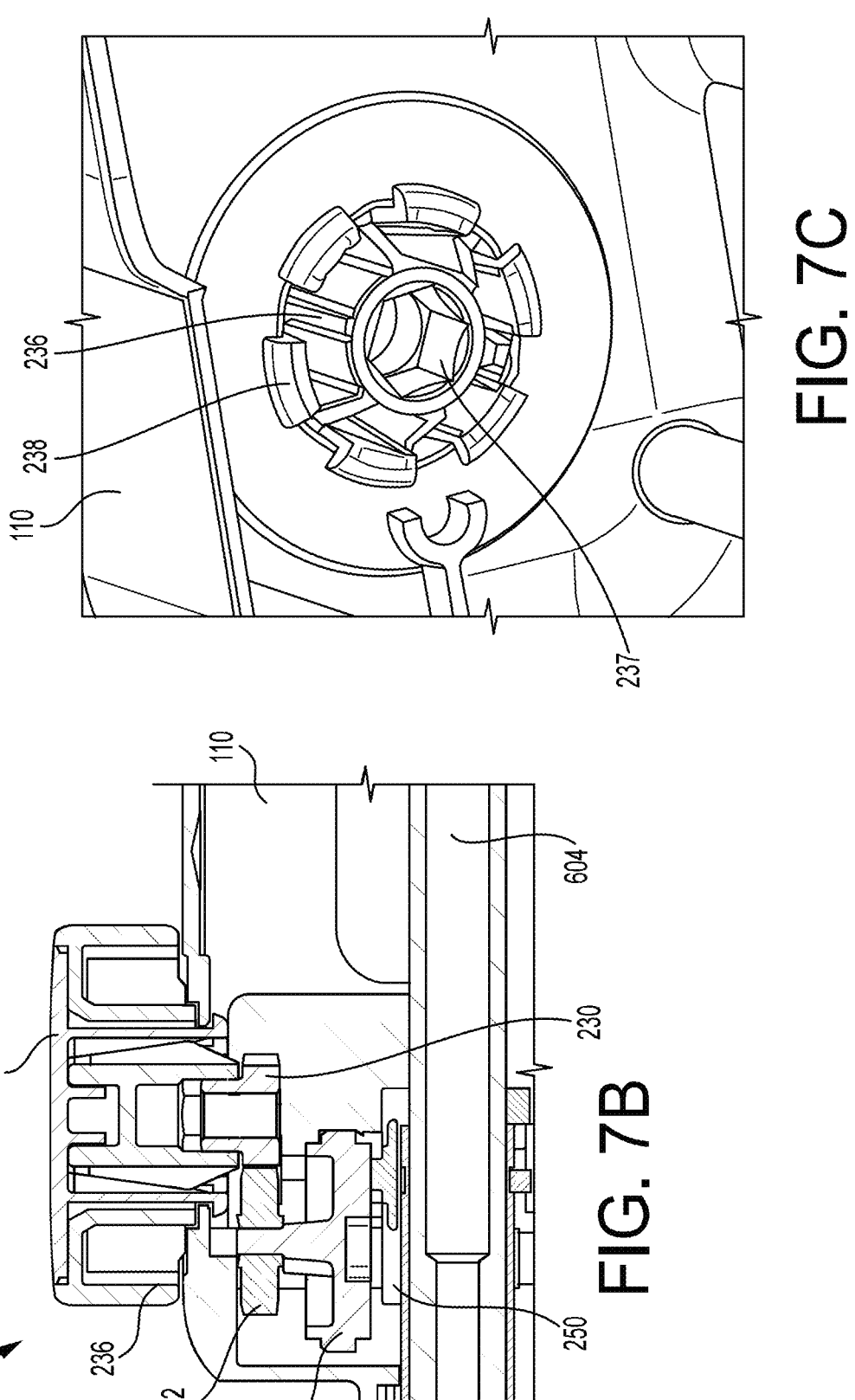
FIG. 7B is a cross-sectional view taken along the longitudinal axis of the surgical instrument and showing details of a manual closure handle, according to aspects of the present disclosure.
FIG. 7C is an underside perspective view of the manual closure handle, according to aspects of the present disclosure.
Figures 8, 9:
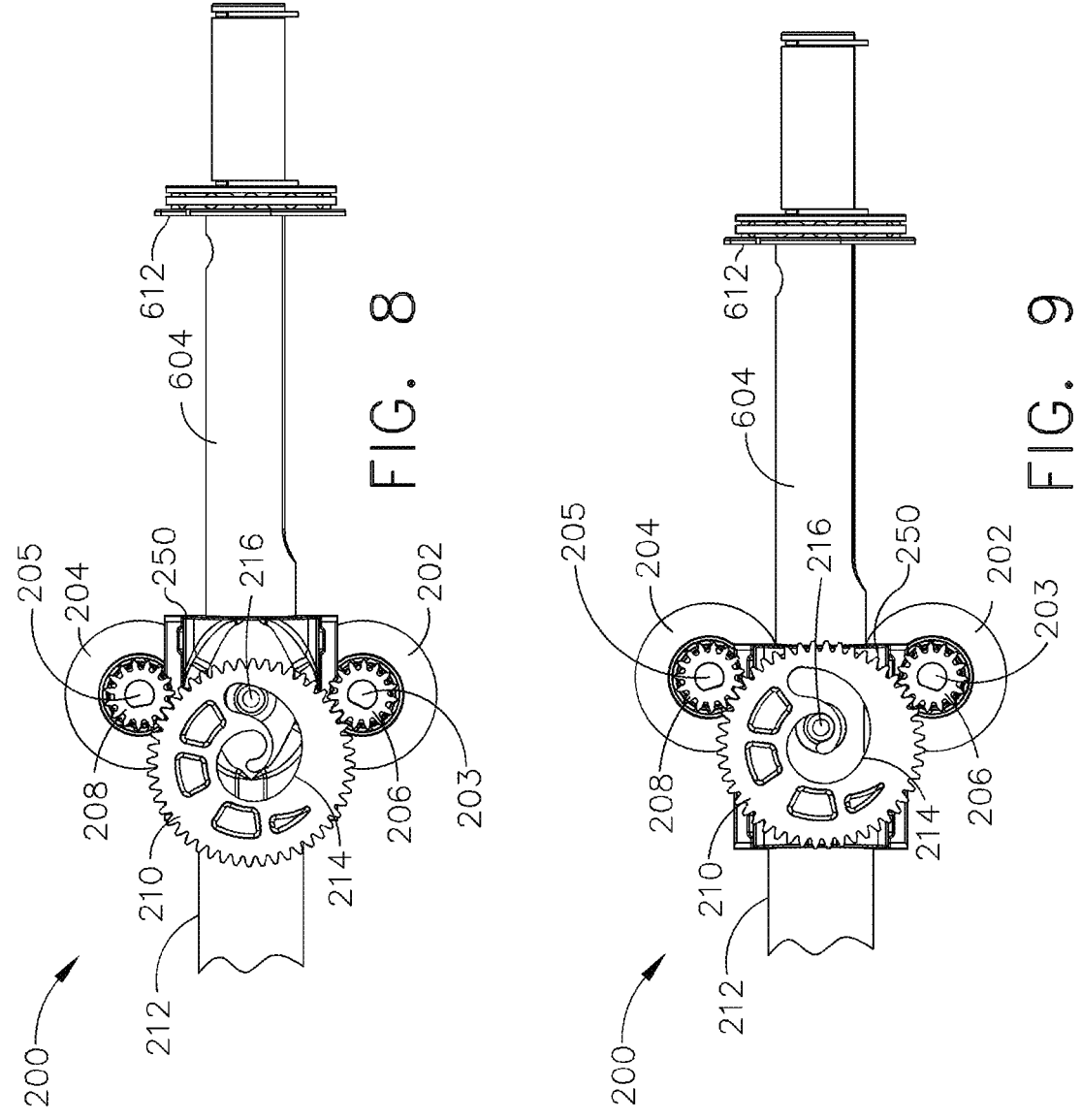
FIGS. 8 and 9 show a top plan view of a closure subsystem, according to aspects of the present disclosure.
Figure 64:
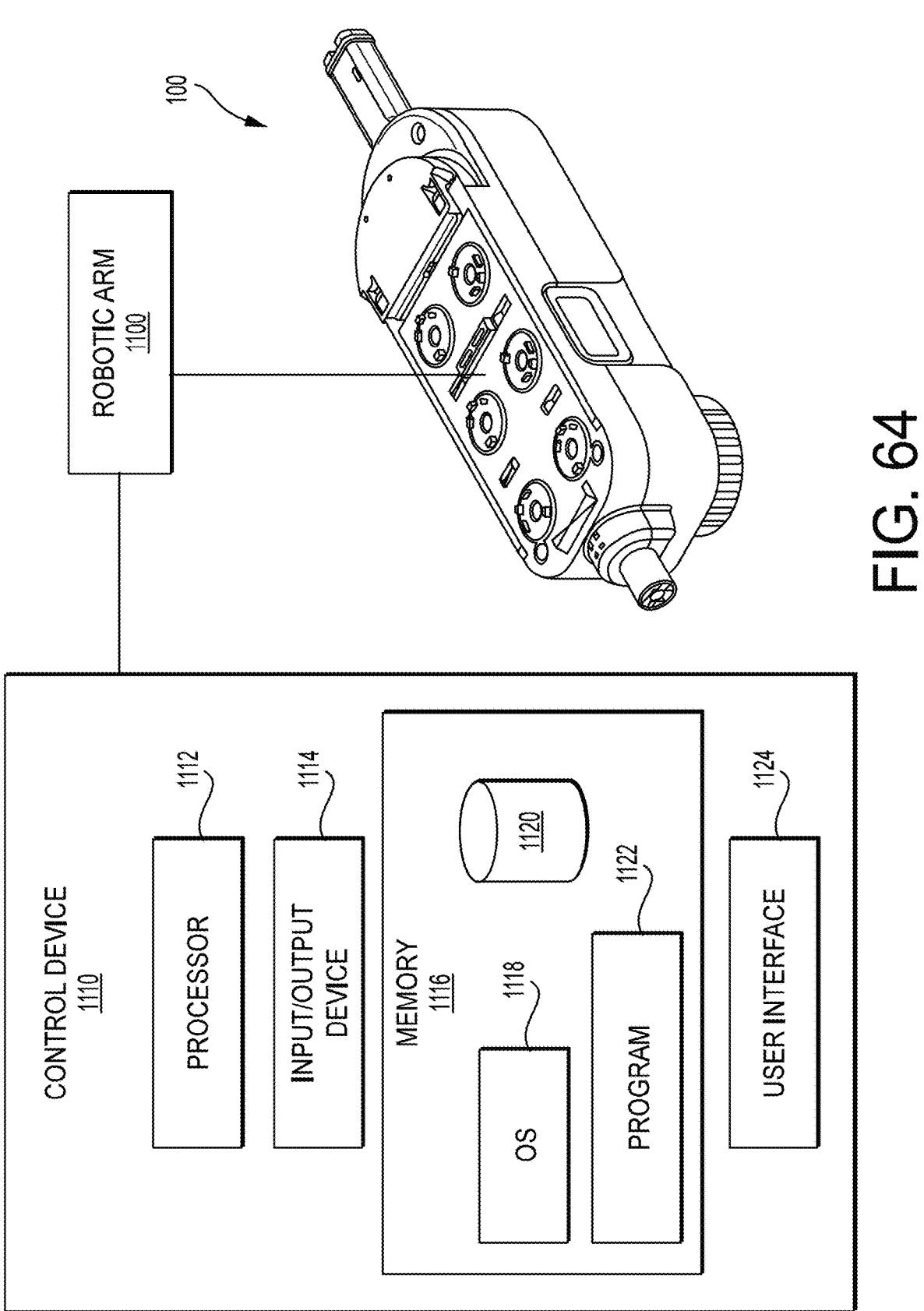
FIG. 64 is a block diagram of a control device, robotic arm, and the surgical instrument, according to aspects of the present disclosure.

Referring now to the closure subsystem 200, FIG. 7A provides a perspective view of the subsystem and FIGS. 8 and 9 provide side views of the subsystem. The closure subsystem 200 includes a first closure input puck 202 and a second closure input puck 204. The first closure input puck 202 is configured to engage with a first rotating feature of the robotic arm (e.g., first closure robotic output 902 in FIG. 2) and the second closure input puck 204 is configured to engage with a second rotating feature of the robotic arm (e.g., second closure robotic output 904 in FIG. 2). In this way, the robotic arm can be configured to transmit a greater amount of torque to the closure subsystem 200 to cause the anvil 152 to open or close than would be possible with only a single input puck. Robotic arm 1100 is also shown in the schematic of FIG. 64.

The first closure input puck 202 can be coupled to a first closure input rod 203 that extends into the outer housing 102. The first closure input rod 203 can be further coupled to a first closure spur gear 206. Thus, when the first closure input puck 202 rotates, it will also cause the first closure input rod 203 and the first closure spur gear 206 to rotate. Similarly, the second closure input puck 204 can be coupled to a second closure input rod 205 that extends into the outer housing 102. The second closure input rod 205 can be further coupled to a second closure spur gear 208. Thus, when the second closure input puck 204 rotates, it will also cause its corresponding second closure input rod 205 and the second closure spur gear 208 to rotate. The first closure input rod 203 can be held in place by a first retention clip 218 and the second closure input rod 205 can be held in place by a second retention clip 220.

Figure 42:
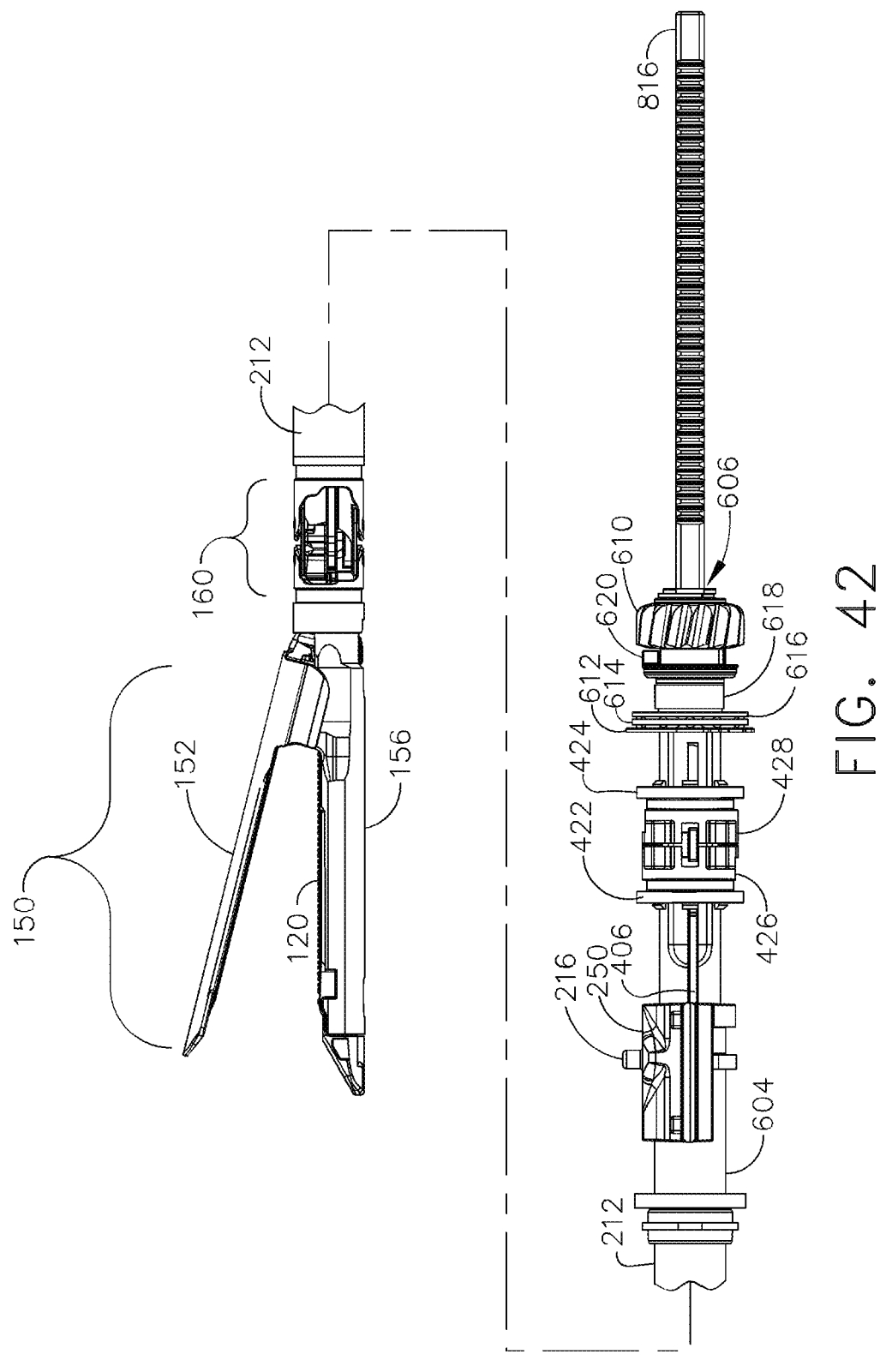
FIG. 42 shows shaft closure components of a surgical instrument with an anvil in an open position, according to aspects of the present disclosure.
Figure 43:
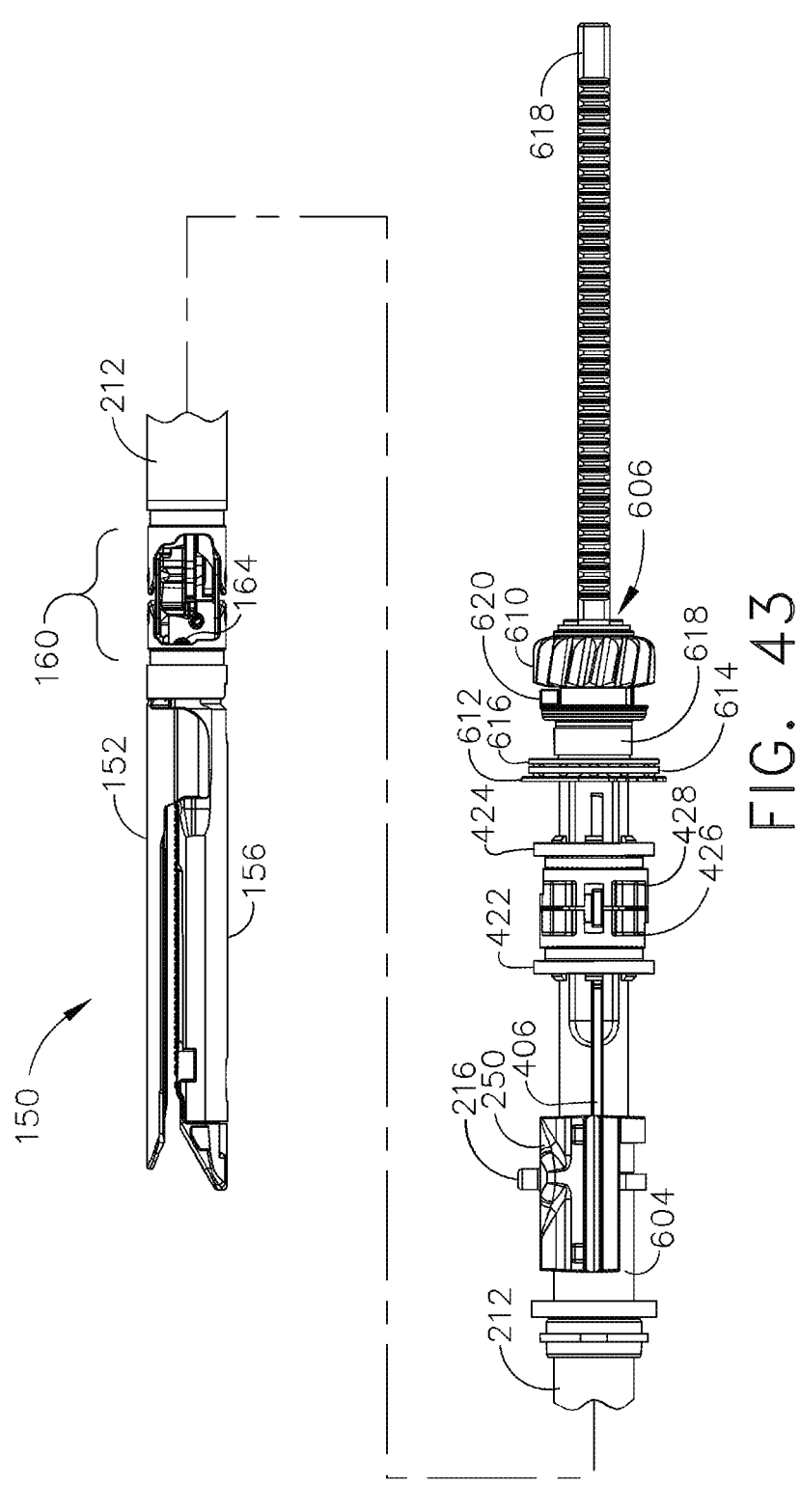
FIG. 43 shows shaft closure components of a surgical instrument with an anvil in a closed position, according to aspects of the present disclosure.

The first closure spur gear 206 and the second closure spur gear 208 can each be rotationally engaged with a closure cam gear 210. As shown in FIGS. 8 and 9, the closure cam gear 210 includes a cam track 214 that receives a yoke pin 216 that can be coupled to the closure yoke 250. As the closure cam gear 210 rotates, the cam track 214 can cause the yoke pin 216 to slide proximally and distally, thereby causing the closure yoke 250 to slide proximally and distally. In other words, as the closure cam gear 210 is rotated in a first direction, the cam track 214 will guide the yoke pin 216 along the cam track 214 in either the proximal or distal direction. Because the yoke pin 216 is coupled to the closure yoke 250, movement of the yoke pin 216 proximally or distally causes the closure yoke 250 to move proximally or distally. As explained previously, movement of the closure yoke 250 causes the anvil 152 to open or close via the closure tube 212. FIG. 42 shows the anvil 152 in an open configuration and the closure yoke 250 is positioned more proximally, and FIG. 43 shows the anvil 152 in a closed configuration where the closure yoke 250 has slid more distally. The closure yoke 250 can have a wing 252 (see FIGS. 7A and 39) extending therefrom that can track through a corresponding track in the housing 102 to allow the closure yoke 250 to translate proximally and distally but not rotate. The closure yoke 250 can be, as shown in FIGS. 8 and 9, a full or partial sleeve attached to the closure tube 212, such that translational movement of the yoke pin 216, which extends from the closure yoke 250, causes translation of the closure tube 212. The yoke pin 216 can, therefore, be directly or indirectly connected to the closure tube 212, i.e., directly to the closure to or indirectly by means of being coupled to a sleeve-like closure yoke 250.

The cam track 214 can be a non-linear track that is configured to have changing movement profile as the closure cam gear 210 rotates. The cam track 214 is highlighted in detail in FIG. 10A, which shows a top view of the cam track 214 with an example non-linear profile. In some implementations, the cam track 214 can be a logarithmic spiral. The cam track 214 is not necessarily fully logarithmic, and in some instances can be represented by higher order polynomials, as some implementations can include a portion that is non-linear, a portion that has a constant radius, and a portion that connects the non-linear and constant radius portions. These different portions can be created by splines. One novel aspect of this non-linear cam track 214 design is that it can be shaped such that once the yoke pin 216 reaches a portion of the cam track 214 with a constant radius, the closure cam gear 210 rotates but the yoke pin 216 does not move axially. This feature can provide benefits by accounting for, and providing tolerance for, robotic inaccuracies.

Figure 10A:
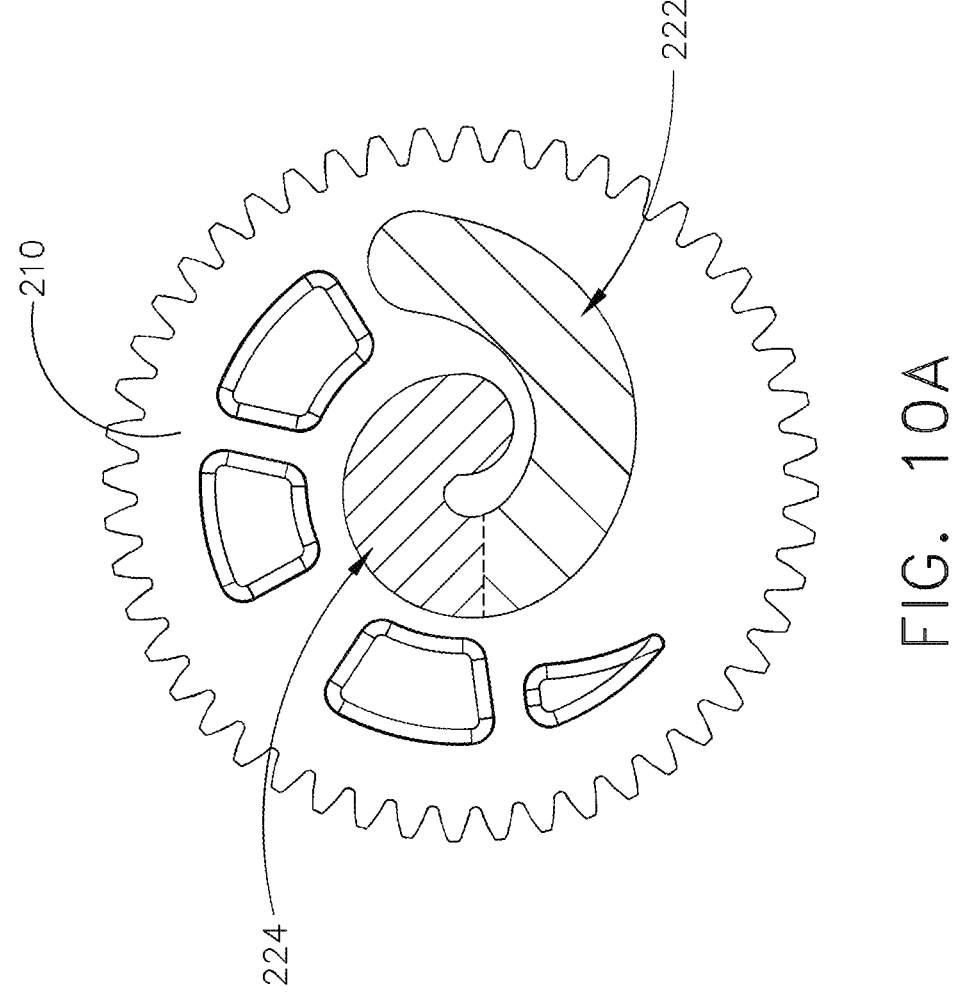
FIG. 10A is a top view of a closure cam gear, according to aspects of the present disclosure.

Continuing to refer to the closure cam gear 210 shown in FIG. 10A, the cam track 214 can include a first zone 222 and a second zone 224. The first zone 222 of the cam track 214 can be configured to cause the move the yoke pin 216 such that the anvil 152 compresses tissue without a great amount of force. The second zone 224 of the cam track 214, on the other hand, can be configured to cause the anvil 152 to compress tissue with a force sufficient to keep the tissue in place within the end effector 150 for cutting and/or stapling of the tissue. Furthermore, the slope of the cam track 214 at the first zone 222 and the second zone 224 can be varied to affect the speed and force with which the anvil 152 opens and closes. This change in speed and force therefore can be altered all while the speed of the input pucks 202, 204 remains the same. It will be understood that the cam track 214 is contiguous, non-linear, and smooth, so FIG. 10A depicting the different "zones" is not to indicate that there is a break or discontinuity in certain sections of the cam track 214. FIG. 8 shows a fully open configuration, where the yoke pin 216 is at a position within the cam track 214 such that the anvil 152 is fully open, thereby maximizing the amount of tissue that can be placed in the jaws (e.g., anvil and channel) of the end effector 150. FIG. 9 shows a fully closed configuration, where the yoke pin 216 is within a constant radius portion of the cam track 214 (in this view the yoke pin 216 is also at the very end of the cam track 214). A fully closed configuration can indicate that the surgical instrument 100 is ready to proceed with firing (e.g., transection and/or stapling). Partially open configurations can exist between the examples shown in FIGS. 8 and 9 wherein the system can grasp tissue.

Figure 10B:
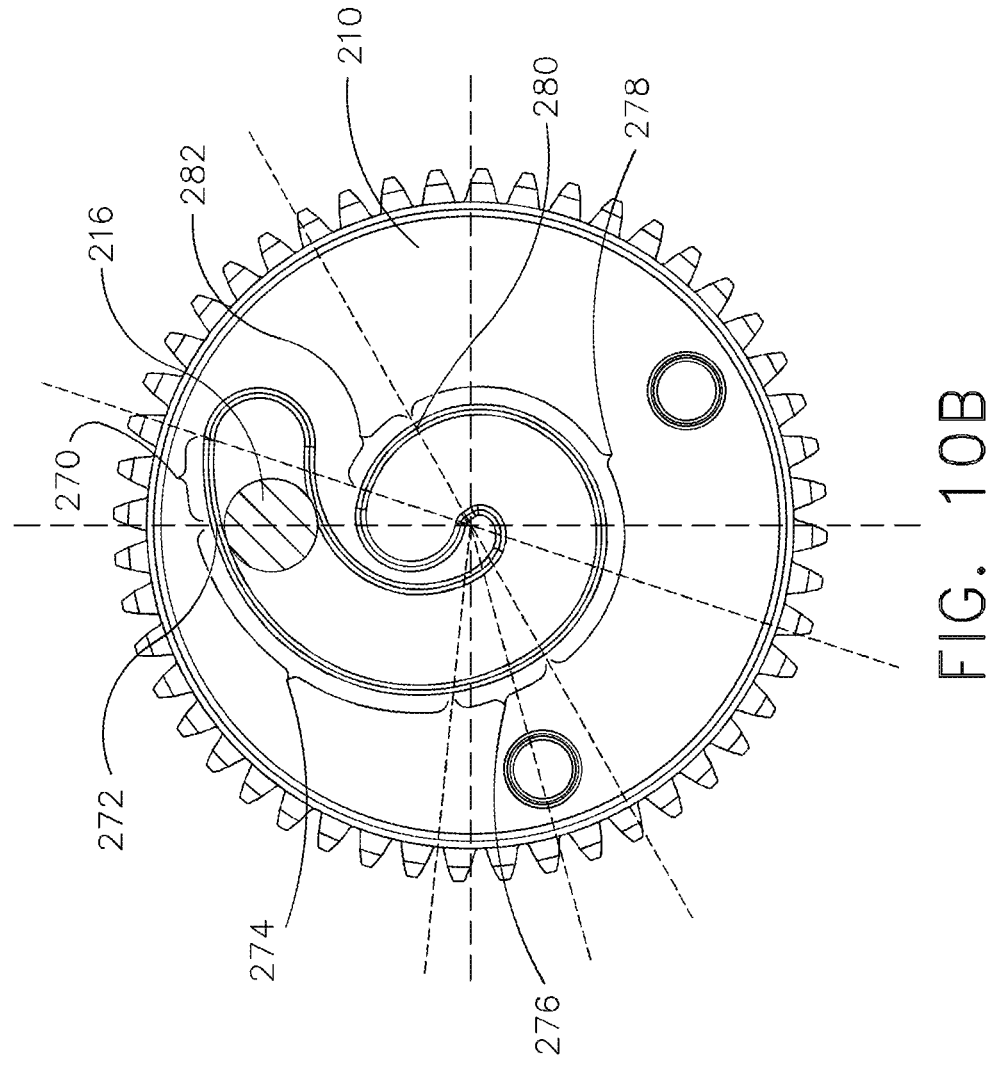
FIG. 10B is a bottom view of a closure cam gear, according to aspects of the present disclosure.

Referring now to FIG. 10B, which is a bottom view of the closure cam gear 210, the view shows different regions of the cam track 214 that can provide different movement profiles for the yoke pin 216. Referencing this view in FIG. 10B, as the closure cam gear 210 rotates clockwise, the yoke pin 216 translates downward in the view (downward being distally in relation to the shaft 604, see FIG. 7A). The regions of the cam track 214 can provide different movement profiles depending on where in the cam track 214 the yoke pin 216 is located. For example, the closure cam gear 210 in FIG. 10B has indications of degrees for reference, up being labeled 0°, left being labeled 90°, down being labeled 180°, and right being labeled 270°. The cam track 214 can include an open dead zone 270 that exists between around −20° and around 0°. The open dead zone 270 is a region beyond an open position 272 that provides a level of tolerance should the closure cam gear 210 be rotated beyond the open position 272. The open position 272, or home position, can be a hard stop position where the closure ring 226 is positioned proximally, allowing the anvil 152 to be fully open (see FIG. 42). The cam track 214 of FIG. 10B includes a high-speed compression region 274 positioned in the next portion of the cam track 214 beyond the open position 272. This high-speed compression region 274 can extend from around 0° to around 90°. The high-speed compression region 274 has a curvature that enables the yoke pin 216 to transition distally quickly while providing a low amount force (for example closing force on the anvil 152, see FIG. 42). At around 90° on the closure cam gear 210 of FIG. 10B is a force transition region 276. Extending beyond the force transition region 276 is a high force region 278. The high force region 278 can extend from around 90° to around 300° on the closure cam gear 210 of FIG. 10B. This region provides a low speed, high force movement profile for the distal movement of the yoke pin 216. The high force region 278, for example, can be a portion of the movement profile that begins to put a large amount of compression on the tissue that is being cut and/or stapled. At around 300° on the closure cam gear 210 of FIG. 10B is a closing target 280. Any point beyond the closing target 280 can be considered as "fully closed", as in the force and distal movement yoke pin 216 are considered met. Extending beyond the closing target 280, and from about 300° to the end of the cam track 214, is a constant force region 282. Like the constant radius portion described above, the constant force region 282 can be a section of the cam track 214 where the closure cam gear 210 rotates but the yoke pin 216 does not move axially. This can help to provide tolerance for any positional error by the robot (e.g., positional errors by the first closure robotic output 902 and/or second closure robotic output 904 in FIG. 2).

The closure subsystem 200 can further include a manual closure spur gear 230 that is coupled to a manual closure handle 234 (as shown in FIGS. 7B and 7E-7I) that extends through the outer housing 102. The manual closure handle 234 can be used, for example, by a surgical staff if the surgical robot is unable to open or close the anvil 152. The manual closure spur gear 230 can be rotationally coupled to a manual closure cam gear 232 that can be keyed to the closure cam gear 210. In this way, rotation of the manual closure handle 234 will cause the manual closure spur gear 230 and the manual closure cam gear 232 to rotate, thereby causing the closure cam gear 210 to rotate and open or close the anvil 152. As will be appreciated, the manual closure handle 234 provides a surgical staff with the ability to open and close the anvil 152 when the surgical instrument 100 is disconnected from a surgical robot or to override the opening or closing of the anvil 152 when connected to the surgical robot.

As shown in FIGS. 7E-7I, the manual closure handle 234, in some examples, includes a manual closure handle grip 236 and a manual closure handle clip 238. The manual closure handle grip 236 can extend beyond an outer portion of the housing 102 such that the physician or surgical staff can grip the manual closure grip 236 and rotate it to cause the anvil 152 to open or close. The manual closure handle clip 238 can be configured to extend through the manual closure handle grip 236 and into the housing 102 to attached to the manual closure handle 234 to the housing 102. The manual closure handle clip 238 can include one or more protruding features that can snap into place when pushed into the housing 102 to attached to the manual closure handle 234 to the housing 102. In other examples, the manual closure handle grip 236 and the manual closure handle clip 238 can be integrated into a single component.

Figure 7E:
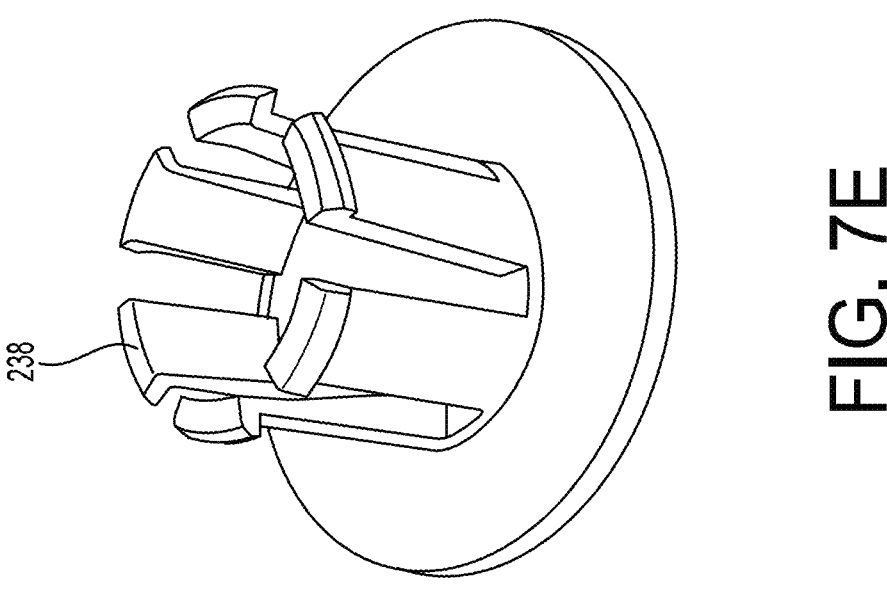
FIG. 7E is a detail view of a manual closure handle clip, according to aspects of the present disclosure.
Figure 7D:
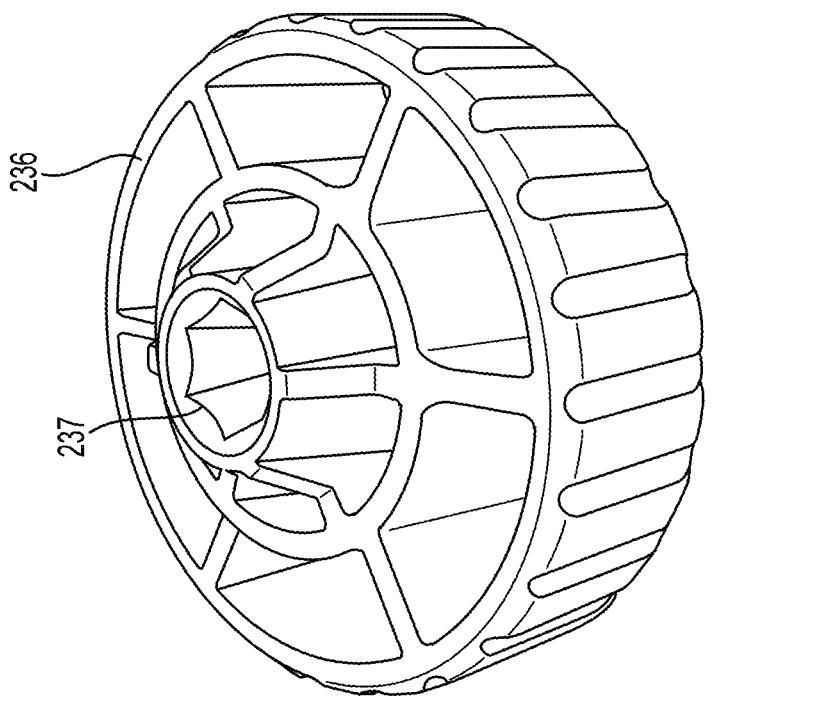
FIG. 7D is a detail view of a manual closure handle grip, according to aspects of the present disclosure.
Figure 7F:
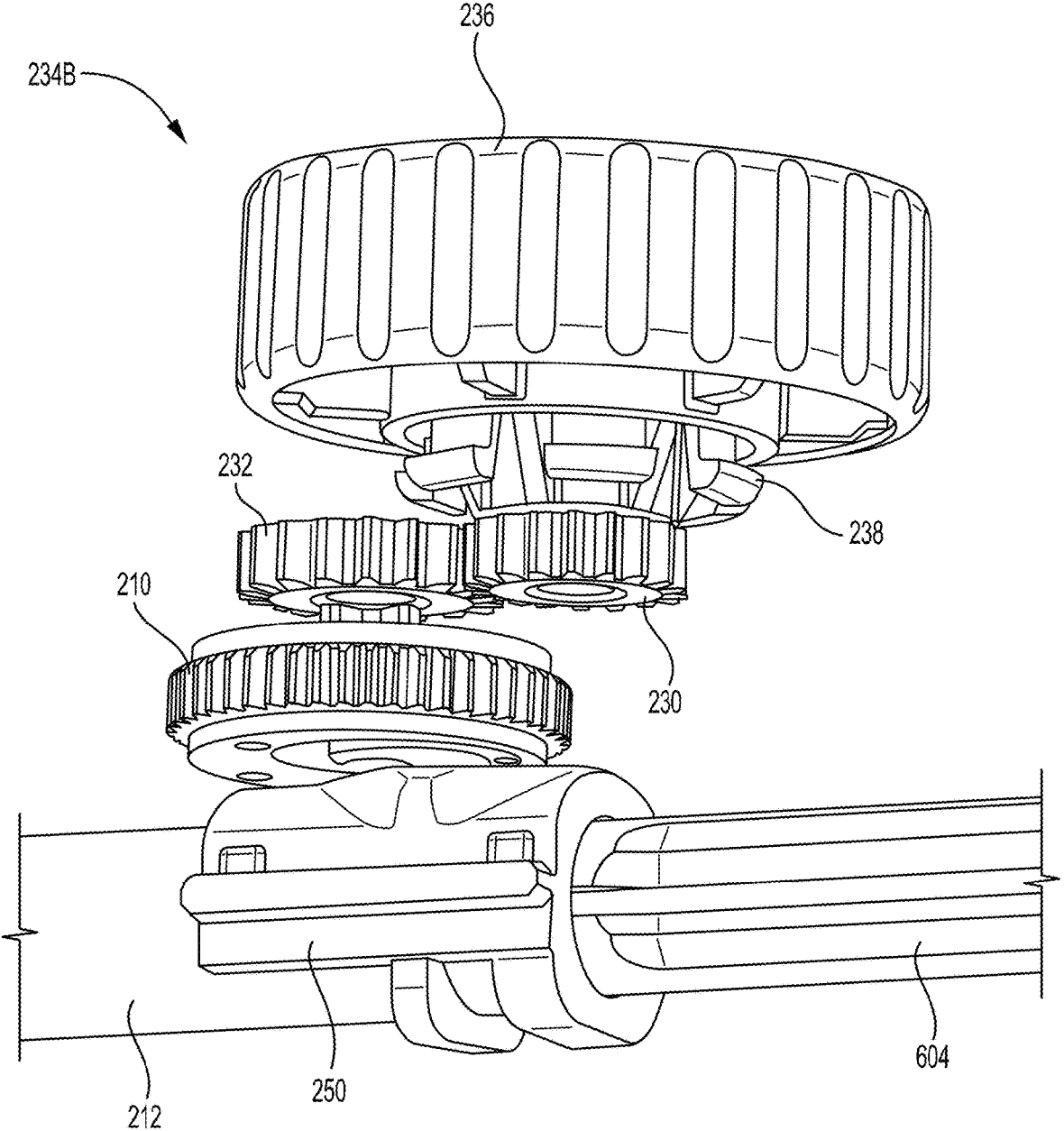
FIG. 7F is a detail view of the closure subsystem with manual closure handle, according to aspects of the present disclosure.

The manual closure handle grip 236 can attach to the manual closure spur gear 230 by, for example but not limitation, receiving a protrusion of the manual closure spur gear 230 into a recess formed into the manual closure handle grip 236 (as shown in FIGS. 7E and 7F). The manual closure handle grip 236 can include engagement surfaces 237 that can align with corresponding engagement surfaces of the manual closure spur gear 230 to transfer forces from the manual closure handle grip 236 to the manual closure spur gear 230 when rotated. For example, the protrusions of the manual closure spur gear 230 and the recess of the manual closure handle grip 236 can be a hex head or other similar features.

Although not shown, in some examples, the manual closure handle grip 236 could include geometry that limits the travel, or provides some resistance to the travel, of the manual closure handle grip 236 at predetermined locations such that the manual closure handle grip 236 is stopped or at least slowed at positions corresponding to desired positions of the opening and closing of the anvil 152. Alternatively, or in addition, the manual closure handle grip 236 or the manual closure handle clip 238 can include markings, colors, protrusions, recesses, etc. that indicate the position of the anvil 152. In some examples. The manual closure handle grip 236 or the manual closure handle clip 238 can include transparent features that reveal indicators at certain positions of rotation to indicate the status. Furthermore, the manual closure handle 230 and/or the closure subsystem 200 can include torque limiting features to prevent over torquing of the closure subsystem 200.

Articulation Subsystem

Figure 11:
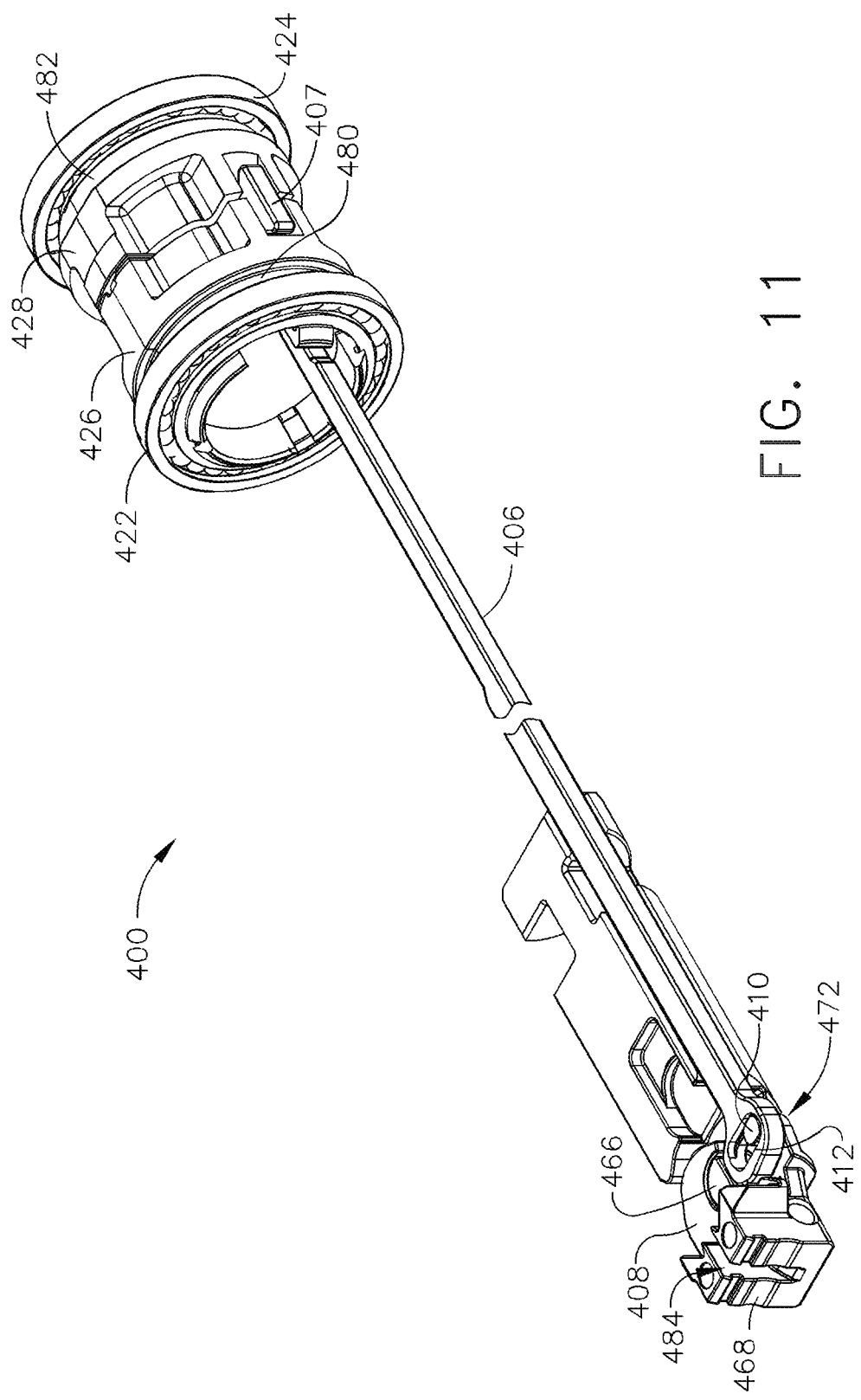
FIG. 11 shows components of an articulation subsystem, according to aspects of the present disclosure.
Figure 23:
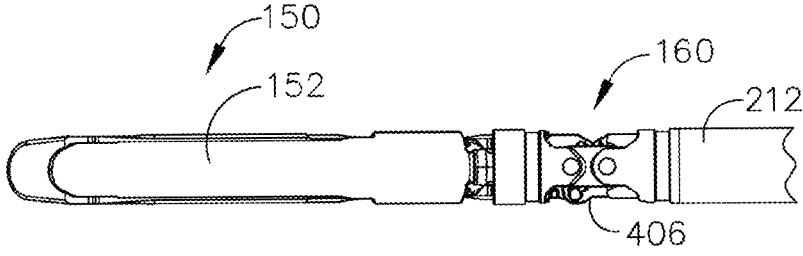
Figure 24:
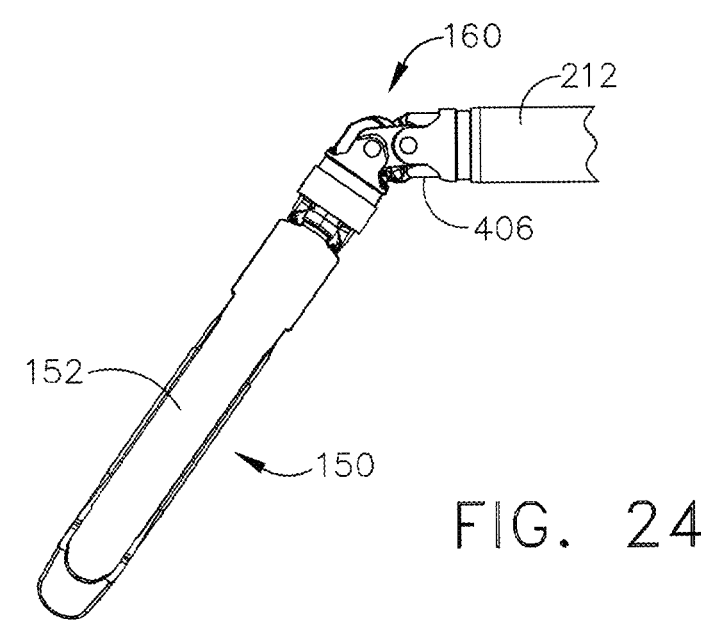
Figure 25:
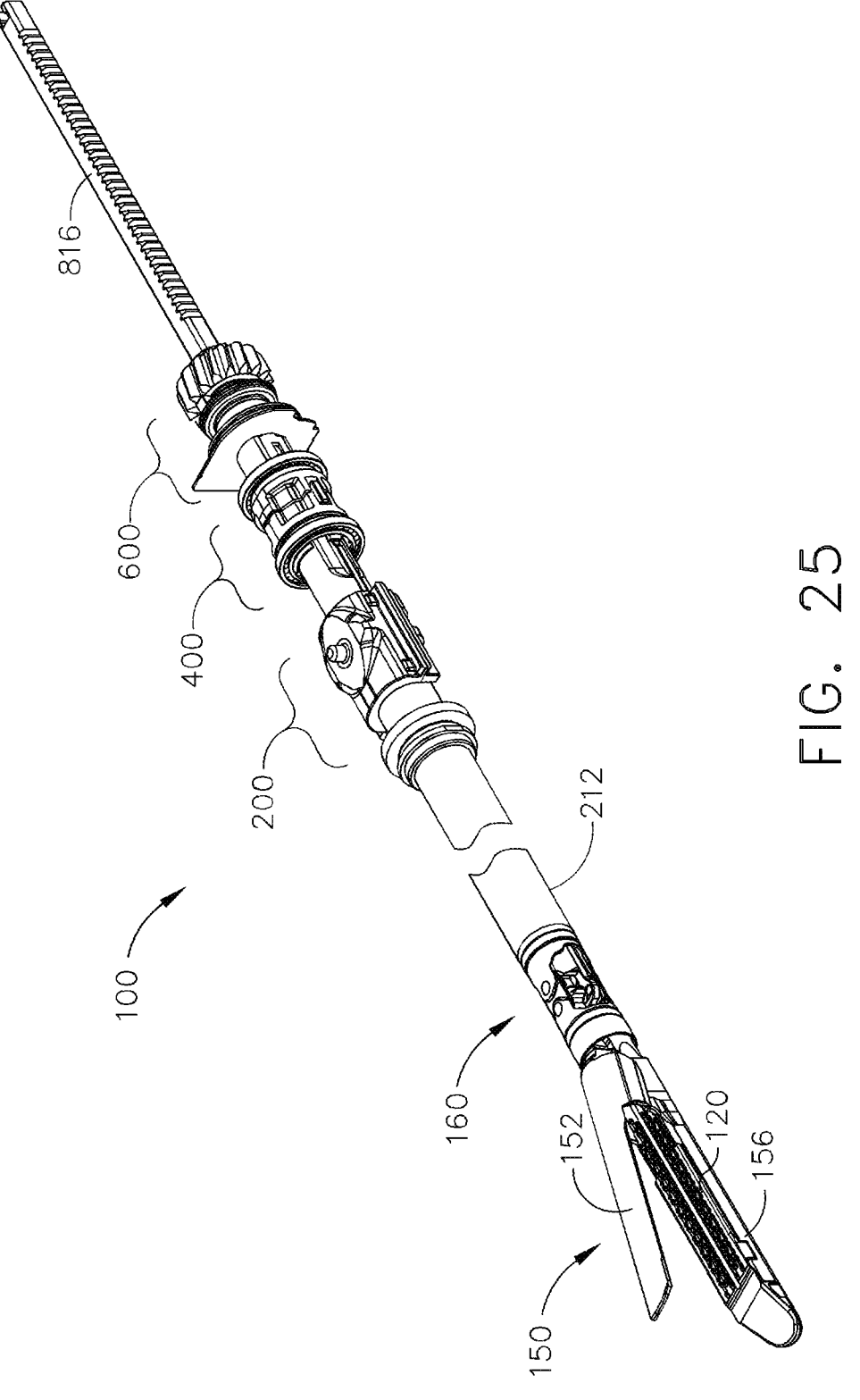
FIG. 25 shows components of a surgical instrument with an anvil of an end effector being open, according to aspects of the present disclosure.

The surgical instrument 100 includes an articulation subsystem 400. Detailed views of the proximal portions of an example articulation subsystem 400 are provided in FIGS. 11-19. Views of the articulation of the distal end of the surgical instrument 100 are shown in FIGS. 20-24. FIGS. 25 and 39 provide perspective views of the articulating portion of the distal end of the surgical instrument 100. Referring specifically to FIG. 11, the articulation subsystem 400 includes an articulation rod 406 extending distally to a distal channel retainer 408. The proximal end 470 of the articulation rod 406 can include an attachment 407 that constrains the articulation rod proximally (e.g., to a first articulation bushing 426 and a second articulation bushing 428). The attachment can be a hook, as shown in FIG. 11, or it can be a loop with pin 507 as shown in FIG. 16. The distal end 472 of the articulation rod 406 can be connected to a distal channel retainer 408 that can pivot back and forth (e.g., left and right) to move, or articulate, an end effector 150 of the surgical instrument 100. An attachment end 468 of the distal channel retainer 408 can, for example, be attached to a channel 156 of the end effector 150 to articulate the end effector 150. The attachment end 468 can also include a band slot 484 for a series of bands 826 to pass through, which are described in greater detail herein with respect to the transection subsystem 800.

Figure 38:
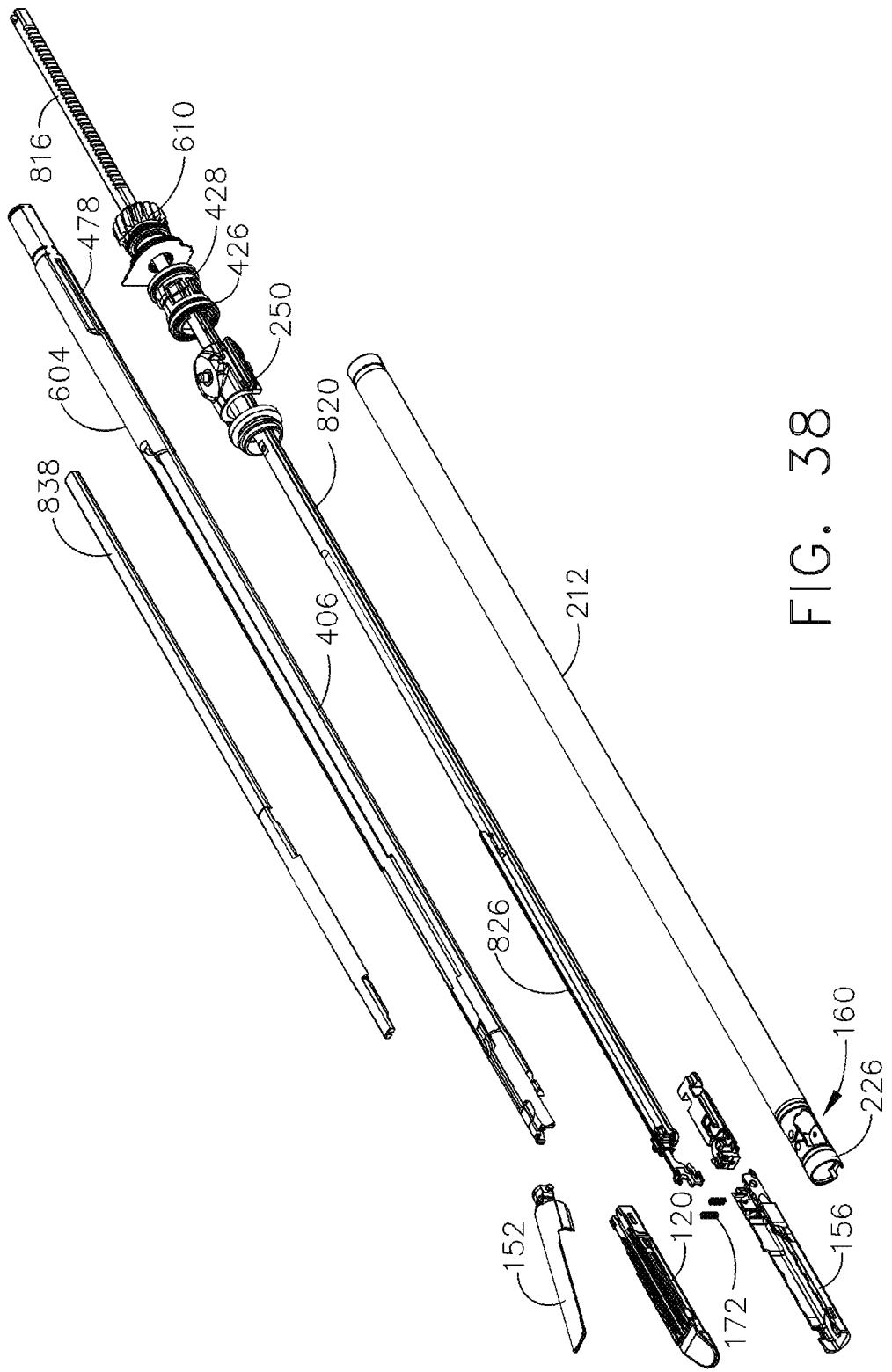
FIG. 38 shows shaft closure and firing components of a surgical instrument, according to aspects of the present disclosure.
Figure 40:
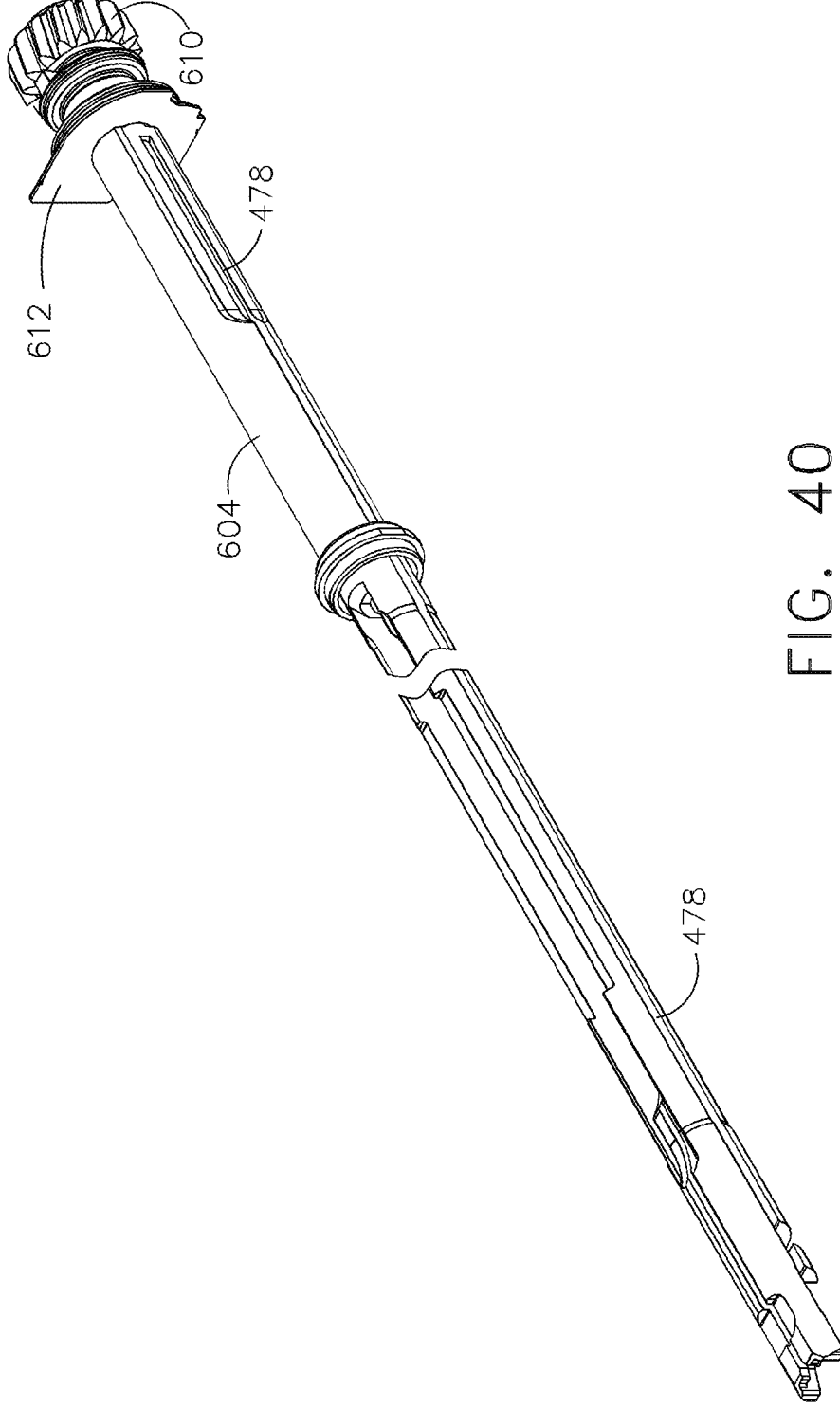
FIG. 40 shows shaft components of a surgical instrument, according to aspects of the present disclosure.

Referring again to the distal channel retainer 408 shown in FIG. 11, the articulation rod 406 can articulate the distal channel retainer 408 back and forth about an articulation joint 466 by pushing and pulling one side of the distal channel retainer 408. To do so, the distal channel retainer 408 can include a retainer pin 410, and the articulation rod 406 can have a rod aperture 412 distally that engages the retainer pin 410. As the articulation rod 406 translates distally, the articulation rod 406 pushes the retainer pin 410 distally and thus articulates the distal channel retainer 408 about the articulation joint 466 in one direction, and as the articulation rod 406 translates proximally, the articulation rod 406 pulls the retainer pin 410 proximally and thus articulates the distal channel retainer 408 about the articulation joint 466 in the opposite direction. The rod aperture 412 can be oblong, as shown in FIG. 11, to account for the translation of the retainer pin 410 laterally as the distal channel retainer 408 rotates, since the articulation rod 406 moves only axially and is constrained to the shaft 604 within a rod groove 478. FIGS. 38 and 40 show a view of the rod groove 478 along the length of the shaft 604.

Figure 12:
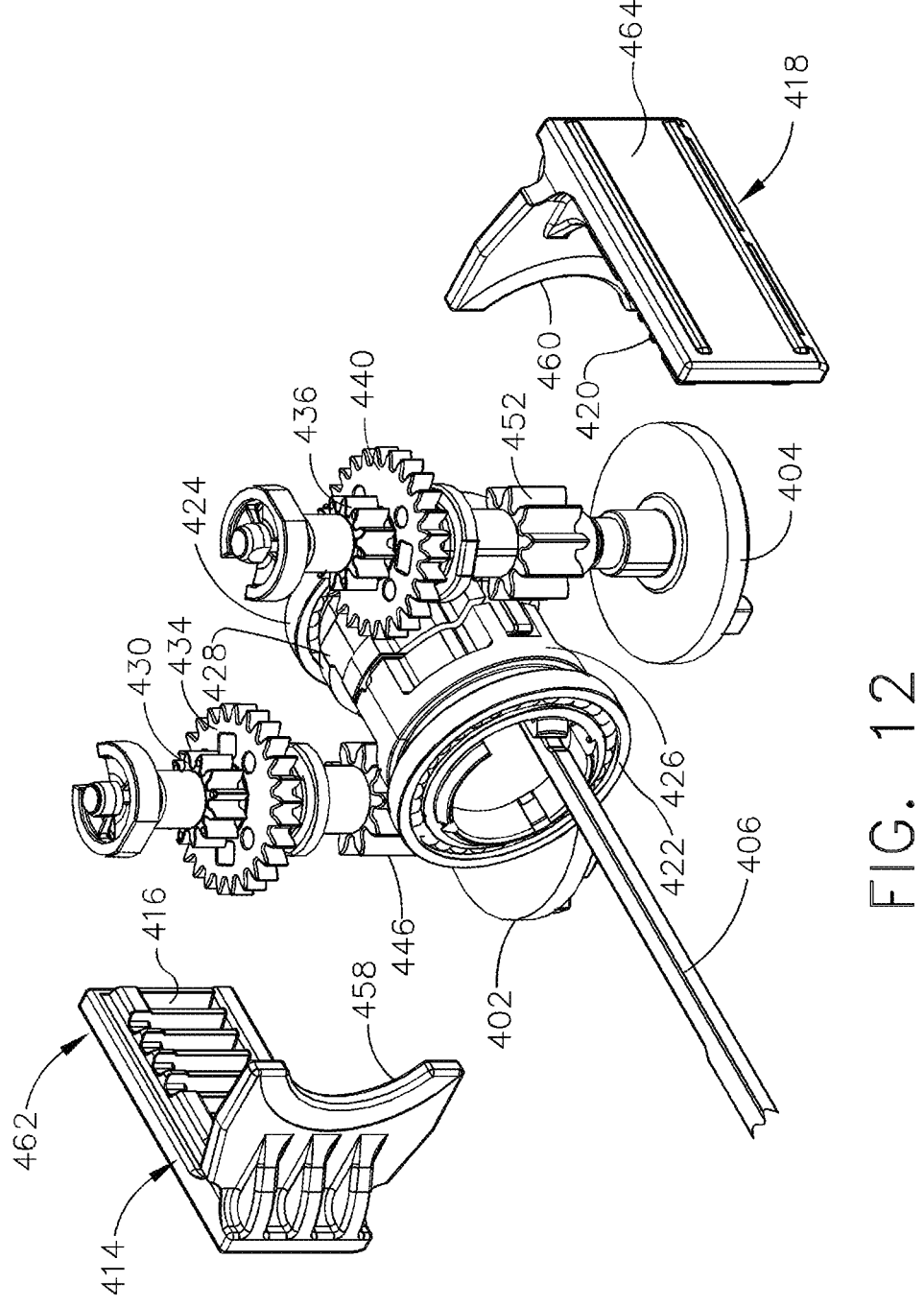
FIG. 12 is a partially exploded view of an articulation subsystem having an "outboard" configuration, according to aspects of the present disclosure.

Referring now to FIG. 12, which is a partially exploded view of the proximal portions of the articulation subsystem 400, the articulation subsystem 400 includes features that accommodate the roll functions of the surgical instrument 100. As will be described in greater detail below with respect to the roll subsystem 600, the surgical instrument 100 includes a shaft 604 that can roll, i.e., rotate back and forth, to improve the access to a transection site. To elaborate, the shaft 604 can be directly connected to the end effector 150, and therefore the combination of rolling of the shaft 604 (via the roll subsystem 600) and articulating the end effector 150 (via the articulation subsystem 400) enables the end effector 150 to articulate with more degrees of freedom than simply left to right by pivoting the distal channel retainer 408. The articulation rod 406 extends along the rotatable shaft 604, for example within the rod groove 478. To account for the ability of the articulation rod 406 to rotate with the shaft 604, the articulation subsystem 400 includes one or more bushings (compare FIG. 12 and FIG. 16) that allow the rotatable robotic outputs to move the articulation subsystem 400 proximally and distally (for example to move the articulation rod 406) along the shaft 604, while also allowing the shaft 604 to rotate within the articulation subsystem 400. The articulation subsystem 400 of FIGS. 12-15 includes a first rack 414 that can be moved via a series of gearing by rotation of the first articulation input puck 402, the puck 402 being engageable with a corresponding rotatable robotic output (e.g., first articulation robotic output 906 in FIG. 2). The inside of the first rack 414 includes rack gearing 416 that facilitates axial translation of the first rack 414 (e.g., distal and proximal within the outer housing 102). The articulation subsystem 400 includes a second rack 418 that can be moved via a series of gearing by rotation of the second articulation input puck 404, the puck 404 being engageable with a corresponding rotatable robotic output (e.g., second articulation robotic output 908 in FIG. 2). The inside of the second rack 418 includes rack gearing 420 that enables axial translation of the second rack 418 (e.g., distal and proximal within the outer housing 102).

To account for the rotation of the shaft 604, the articulation subsystem 400 of FIGS. 12-15 can include a first articulation bushing 426 that is rotatable with the shaft 604, and is rotatably independent of the first rack 414. In other words, the rolling of the shaft 604 will also roll the first articulation bushing 426, all while the first rack 414 remains rotationally stable within the outer housing 102. The first articulation bushing 426 can slide from a first position to a second position along a longitudinal axis 474 of the rotatable shaft 604, thereby moving the articulation rod 406 proximally and distally. The first rack 414 can have a first housing track surface 462 that moves axially within a corresponding track in the outer housing 102, thereby enabling the first rack 414 to slide axially but not rotationally. The first housing track surface 462 and the first bearing surface 458 can be at 90° with respect to each other. The articulation subsystem 400 of FIGS. 12-15 includes a second articulation bushing 428 that is rotatable with the shaft 604, and is rotatably independent of the second rack 418. In other words, the rolling of the shaft 604 will also roll the second articulation bushing 428, all while the second rack 418 remains rotationally stable within the outer housing 102. The second articulation bushing 428 can slide from a first position to a second position along the longitudinal axis 474 of the rotatable shaft 604, thereby moving the articulation rod 406 proximally and distally. The second rack 418 can have a second housing track surface 464 that moves axially within a corresponding track in the outer housing 102, thereby enabling the second rack 418 to slide axially but not rotationally. The second housing track surface 464 and the second bearing surface 460 can be at 90° with respect to each other.

Figure 13:
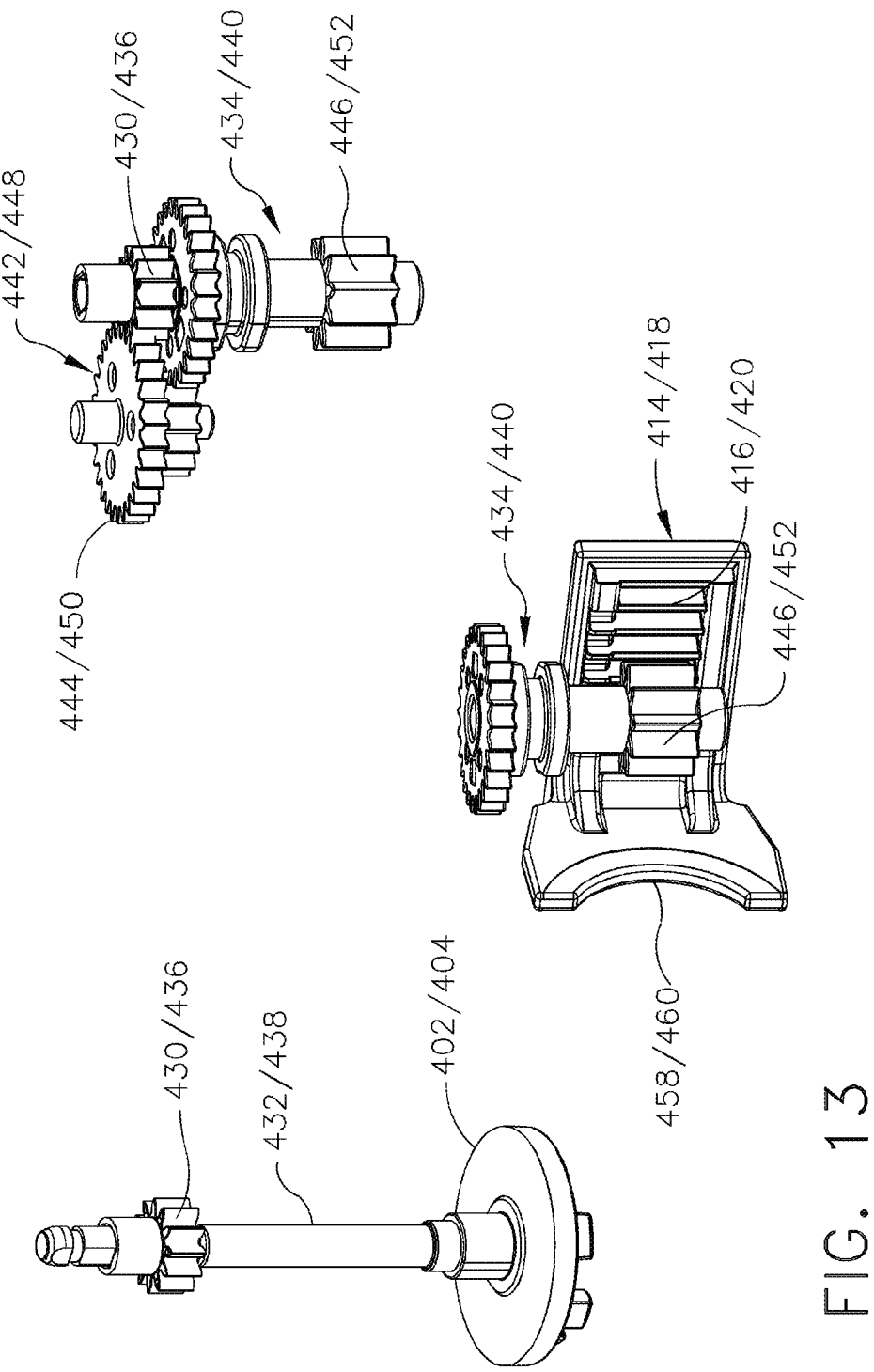
FIG. 13 is an exploded view of gears of an articulation subsystem having an "outboard" configuration, according to aspects of the present disclosure.

Turning now to FIGS. 12 and 13 to describe the gearing of the example articulation subsystem 400, the subsystem includes a first articulation drive shaft 432 extending from the first articulation input puck 402 and including a first drive gear 430. Rotation of the first articulation input puck 402 by the corresponding robotic output can therefore rotate the first drive gear 430. The articulation subsystem 400 includes a first rack gear 434, which can in some instances be a hollow tube gear that slides over the first articulation drive shaft 432, thereby providing a mechanical advantage to the system while also conserving space within the outer housing 102. The first rack gear 434 can be rotatably coupled to the first articulation drive shaft 432 by means of a first compound gear 442 (see FIGS. 5 and 13) that has stepped teeth 444, one portion of the stepped teeth 444 being engaged with the first drive gear 430, and the other portion of the stepped teeth 444 being engaged with the first rack gear 434. As such, rotation of the first articulation drive shaft 432 rotates the first drive gear 430, rotation of the first drive gear 430 rotates the first compound gear 442, and rotation of the first compound gear 442 rotates the first rack gear 434 that is surrounding the first articulation drive shaft 432. Further, the first rack gear 434 includes first rack gear teeth 446 that engage with the rack gearing 416 of the first rack 414. Rotation of the first rack gear 434 therefore causes the first rack 414 to translate proximally and distally to move the first articulation bushing 426.

Similarly, the subsystem can include a second articulation drive shaft 438 extending from the second articulation input puck 404 and including a second drive gear 436. Rotation of the second articulation input puck 404 by the corresponding robotic output can therefore rotate the second drive gear 436. The articulation subsystem 400 can include a second rack gear 440, which can in some instances be hollow a tube gear that slides over the second articulation drive shaft 438. The second rack gear 440 can be rotatably coupled to the second articulation drive shaft 438 by means of a second compound gear 448 that has stepped teeth 450 (see FIGS. 5 and 13), one portion of the stepped teeth 450 being engaged with the second drive gear 436, and the other portion of the stepped teeth 450 being engaged with the second rack gear 440. As such, rotation of the second articulation drive shaft 438 rotates the second drive gear 436, rotation of the second drive gear 436 rotates the second compound gear 448, and rotation of the second compound gear 448 rotates the second rack gear 440 that is surrounding the second articulation drive shaft 438. Further, the second rack gear 440 includes second rack gear teeth 452 that engage with the rack gearing 420 of the second rack 418. Rotation of the second rack gear

440 therefore causes the second rack 418 to translate proximally and distally to move the second articulation bushing 428.

Referring again to the articulation bushings and racks of FIGS. 12-15, the first rack 414 can engage with the first articulation bushing 426 in a manner that enables proximal or distal movement of the first articulation bushing 426, while the first articulation bushing 426 remains able to rotate with the shaft 604. The first rack 414 includes a first bearing surface 458 that abuts the first articulation bushing 426. The first articulation bushing 426 can include a first rack groove 480 around the perimeter of the bushing into which the first bearing surface 458 extends. As the first articulation bushing 426 rotates, the first bearing surface 458 can track through the first rack groove 480. As such, the first bearing surface 458 can be semicircular. Similarly, the second rack 418 can engage with the second articulation bushing 428 in a manner that enables proximal or distal movement of the second articulation bushing 428, while the second articulation bushing 428 remains able to rotate with the shaft 604. The second rack 418 can include a second bearing surface 460 that abuts the second articulation bushing 428. The second articulation bushing 428 can include a second rack groove 482 around the perimeter of the bushing into which the second bearing surface 460 extends. As the second articulation bushing 428 rotates, the second bearing surface 460 can track through the second rack groove 482. As such, the second bearing surface 460 can be semicircular. To enable the bushings to rotate freely while remaining stable within the outer housing 102, the articulation subsystem 400 can include a first articulation bearing 422 around the first articulation bushing 426, and the articulation subsystem 400 can include a second articulation bearing 424 around the second articulation bushing 428.

Figures 14, 15:
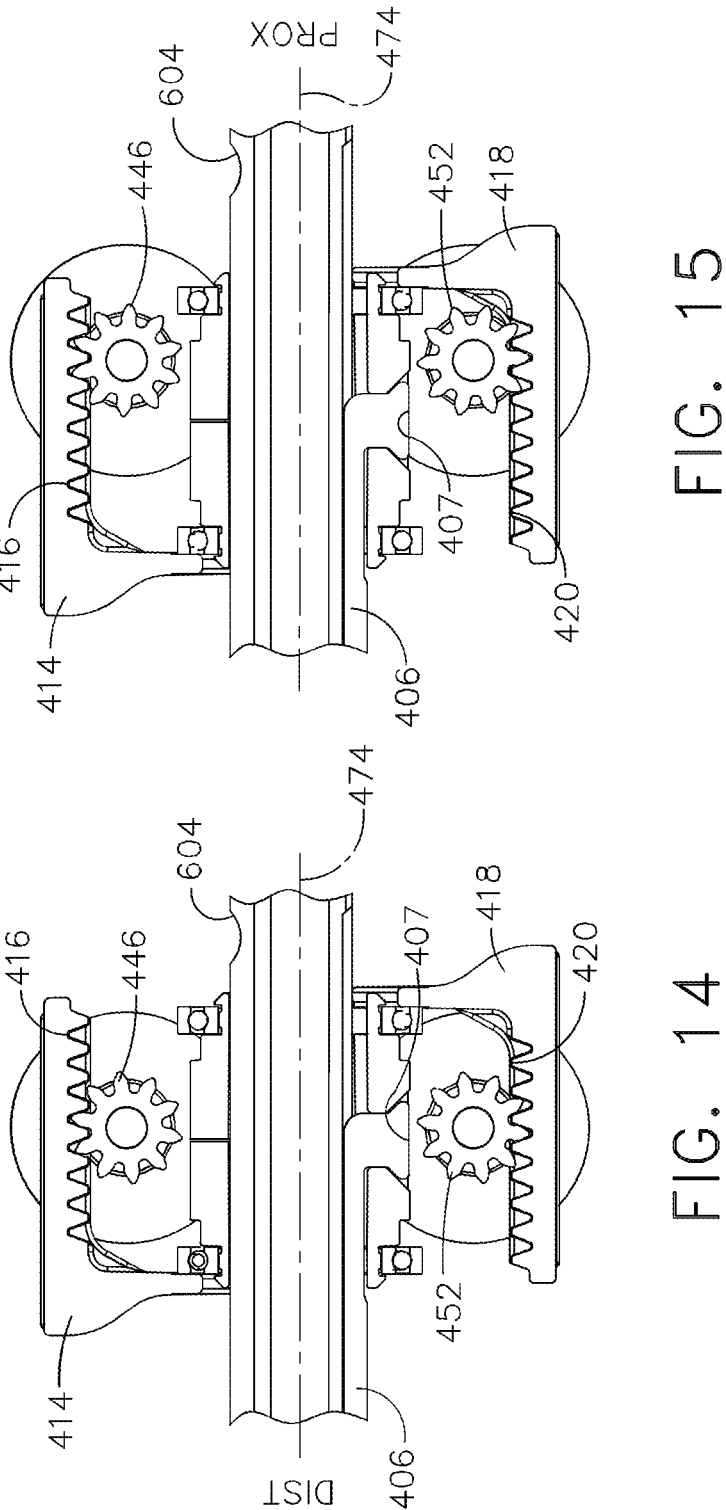
FIGS. 14 and 15 are top views of components of an articulation subsystem having an "outboard" configuration, according to aspects of the present disclosure.
Figure 16:
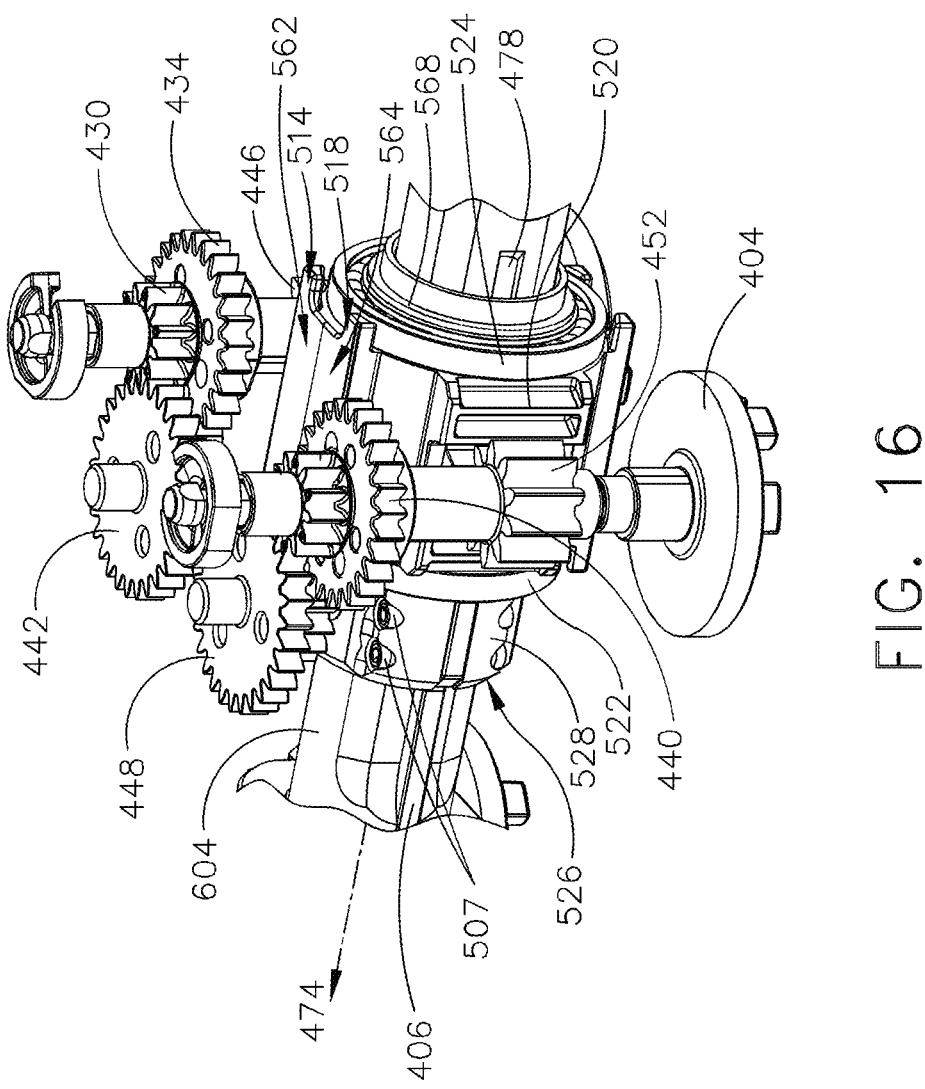
FIG. 16 is a perspective view of an articulation subsystem in an "inboard" configuration, according to aspects of the present disclosure.
Figure 17:
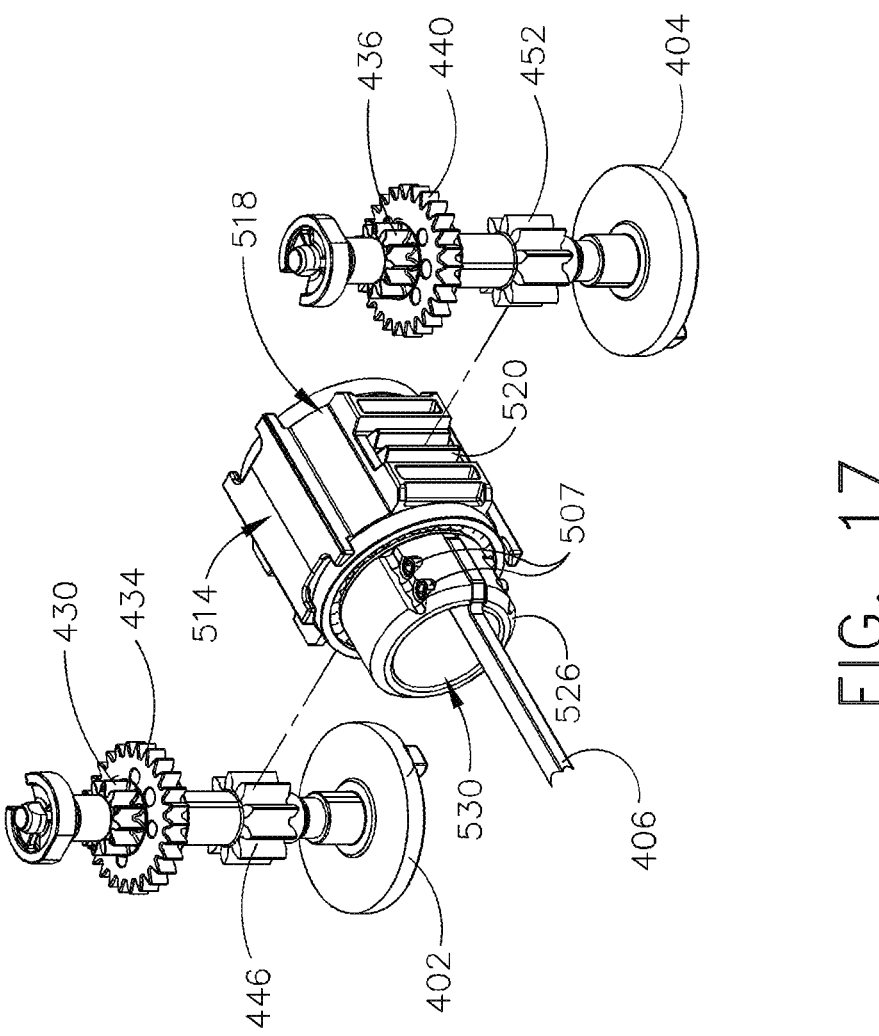
FIG. 17 is a partially exploded view of an articulation subsystem having an "inboard" configuration, according to aspects of the present disclosure.

Referring now to FIGS. 14 and 15 specifically, the two figures show the actuation of the articulation subsystem 400 by movement of the first rack 414 and the second rack 418. FIG. 14 shows an articulation subsystem 400 at a neutral, e.g., 0° state, of articulation. To move the first articulation bushing 426, the first rack gear 434 can rotate in a first angular direction, and the first rack gear teeth 446 move through the first rack gearing 416 of the first rack 414. FIG. 15 shows where the first rack gear 434 (i.e., the first rack gear teeth 446) has rotated in counterclockwise direction to move the first rack 414 distally. Movement of the first rack 414 distally causes the first articulation bushing 426 to translate distally along the longitudinal axis 474 of the shaft 604. In turn, the articulation rod 406 will translate distally, thereby pivoting the distal channel retainer 408 such that the end effector 150 pivots, in this example to the right. In the same example shown in FIG. 15, the second rack gear 440 (i.e., the second rack gear teeth 452) has rotated in clockwise direction to move the second rack 418 distally. Movement of the second rack 418 distally causes the second articulation bushing 428 to translate distally along the longitudinal axis 474 of the shaft 604. If the rack gears 434, 440 are rotated in the opposite directions, the articulation bushings 426, 428 will move proximally along the longitudinal axis 474 of the shaft 604, thereby pulling the articulation rod 406 and causing the end effector to pivot, or articulate, in the other direction.

The example articulation subsystem 400 shown with respect to FIGS. 12-15 could be called an "outboard" configuration, wherein in the racks 414, 418 are external to the gearing mechanisms that move the racks 414, 418 along longitudinal axis 474 of the rotatable shaft 604. To illustrate further, in FIG. 12, the first rack gear 434 is positioned between the first rack 414 and the rotatable shaft 604 (see shaft in FIG. 14); the second rack gear 440 is positioned between the second rack 418 and the rotatable shaft 604. FIGS. 16-19 show an alternative design that could be called an "inboard" configuration. Here, the one or more racks 514, 518 are positioned internal to the respective rack gears 434, 440. Referring now to the design shown in FIG. 16 specifically, the articulation subsystem 400 shown therein includes a first rack 514 that can be moved, via a series of gearing, by rotation of the first articulation input puck 402, the puck 402 being engageable with a corresponding rotatable robotic output (e.g., first articulation robotic output 906 in FIG. 2). The outside surface of the first rack 514 includes rack gearing 516 (see in FIG. 18) that facilitates axial translation of the first rack 514 (e.g., distal and proximal along the shaft 604). The articulation subsystem 400 can include a second rack 518 that can be moved, via a series of gearing, by rotation of the second articulation input puck 404, the puck 404 being engageable with a corresponding rotatable robotic output (e.g., second articulation robotic output 908 in FIG. 2). The outside surface of the second rack 518 includes rack gearing 520 that enables axial translation of the second rack 518 (e.g., distal and proximal along the shaft 604). When two separate racks, i.e., the first rack 514 and the second rack 518, are present, the two racks abut lengthwise to form a hollow cylinder with the lumen 530 extending therethrough.

Figure 48A:
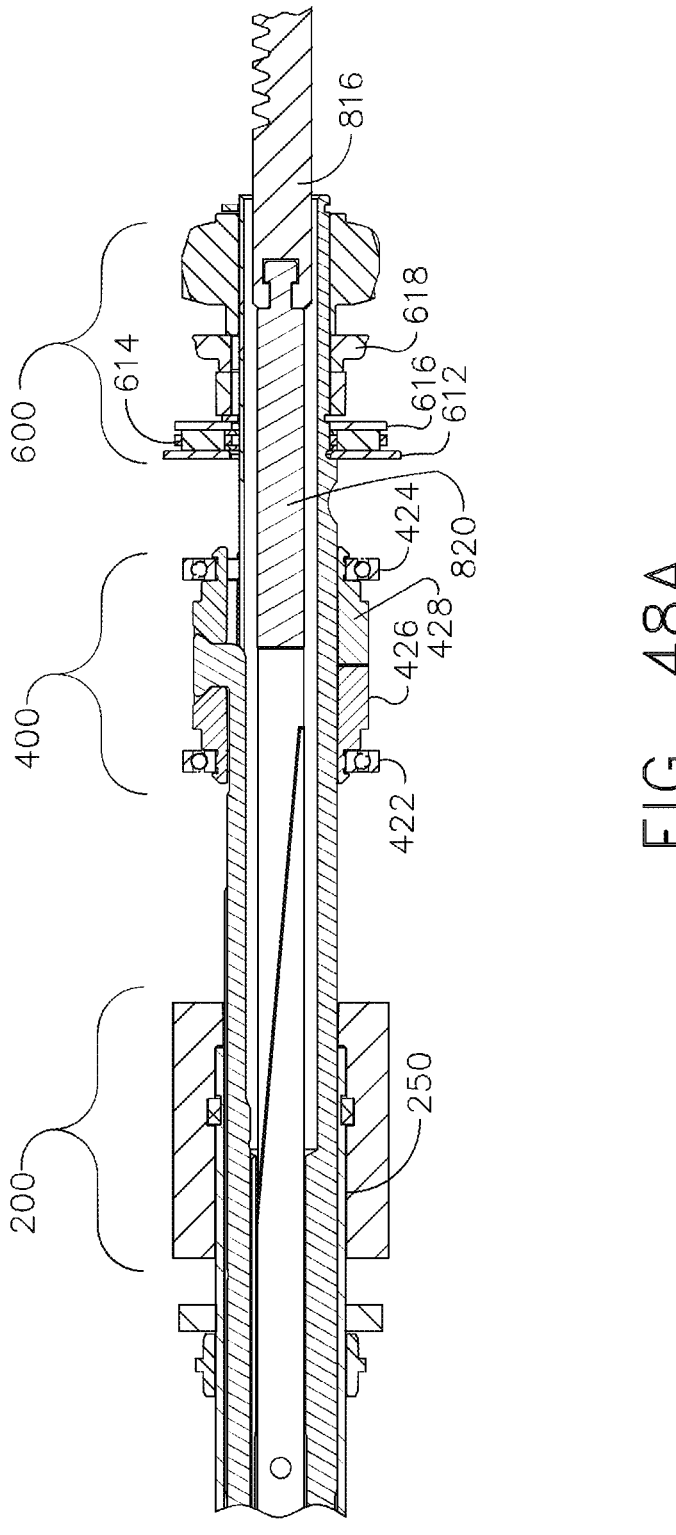
FIG. 48A is a top cross-sectional view of a closure subsystem, an articulation subsystem (outboard), a roll subsystem, and portions of a transection subsystem for a surgical instrument, according to aspects of the present disclosure.
Figure 49A:
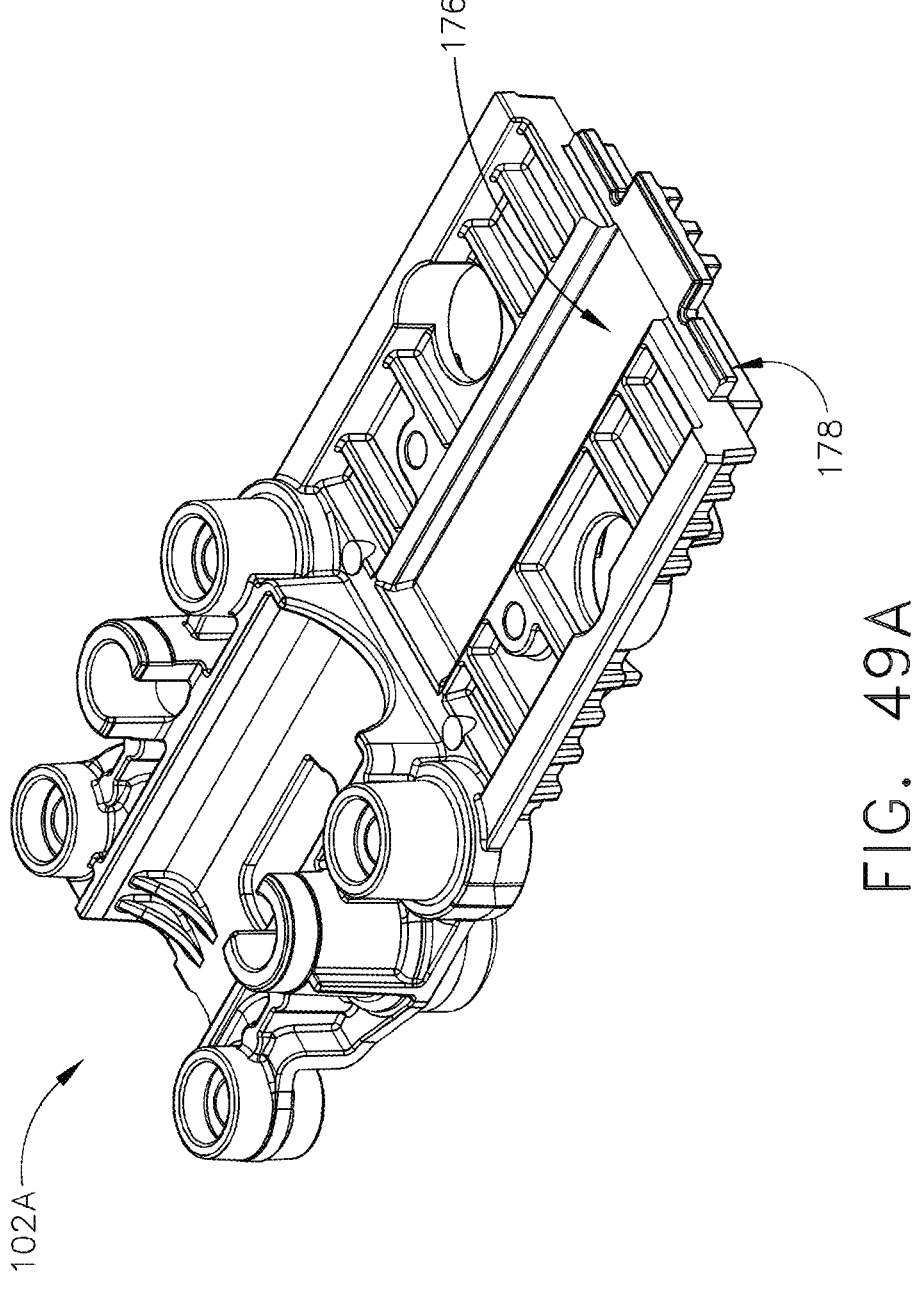
FIG. 49A shows components and features of a housing or an intermediate housing, according to aspects of the present disclosure.
Figure 49B:
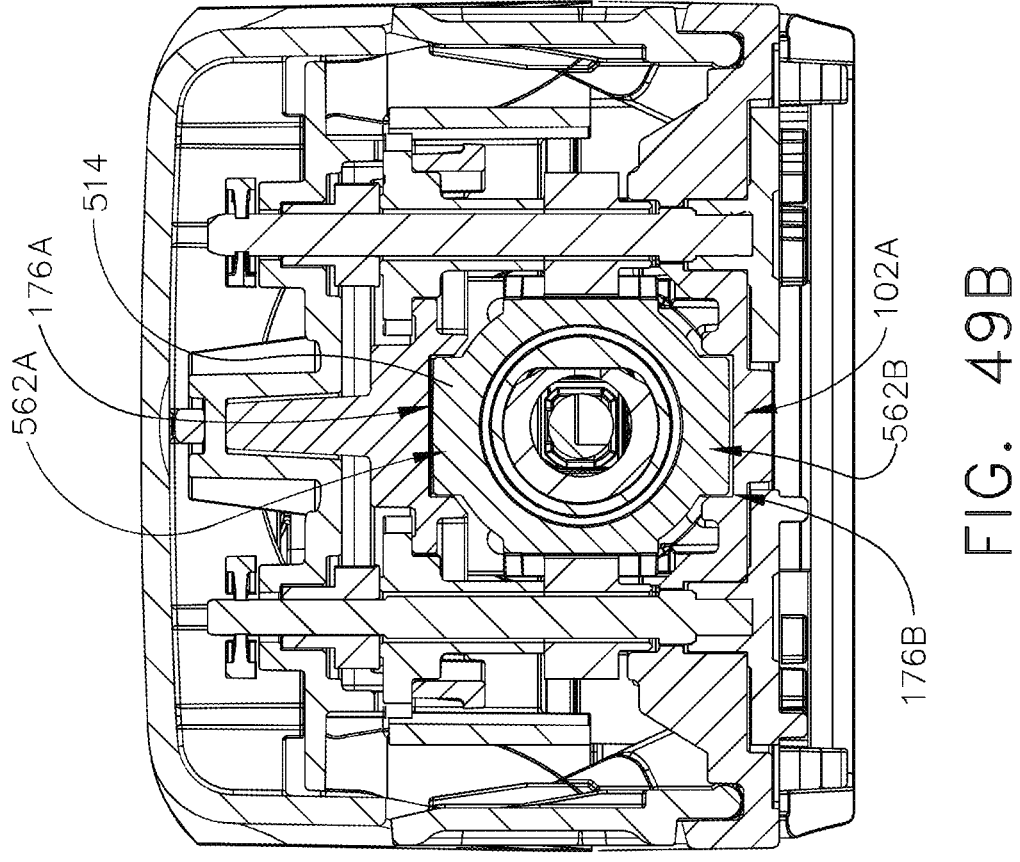
FIG. 49B shows components and features of a housing, according to aspects of the present disclosure.

FIGS. 48A and 49B show how the one or more racks 514, 518 can interact with the housing and/or intermediate housings. As mentioned above, the rack system in the "inboard" implementation can have two racks 514, 518 abutting each other, or in a preferred embodiment can include a single rack 514 with a lumen extending therethrough, the articulation bushing 526 being positioned within the bushing. FIG. 49B shows the example of a single rack 514 with a first housing track surface 562A at the top and a first housing track surface 562B at the bottom. Referring now to the feature shown in FIG. 49A, the figure depicts an intermediate housing 102A, which can be an insert positioned without an outer shell of the housing 102 (see e.g., the exploded view in FIG. 50. The intermediate housing 102A can add additional structural support to the components of the subsystems of the surgical instrument 100. FIG. 49A shows a position of a buttress 178 that can provide structural support for transection and/or roll subsections of the surgical instrument 100. FIG. 49A in particular highlights a track 176 that will accept portions of the racks 514 (e.g., first housing track surface 562 and/or second housing track surface 564 discussed with respect to FIG. 18) such that the one or more racks 514, 518 can translate proximally and distally with respect to the housing 102. FIG. 49B is a cross sectional view showing the interaction of the rack 514 and the track 176. FIG. 49B shows two tracks, an upper track 176A and a lower track 176B corresponding to the with an upper housing track surface 562A and lower housing track surface 562B.

Although FIG. 16 shows two separate racks (i.e., the first rack 514 and the second rack 518, as noted by the line shown lengthwise), it is contemplated and, in most instances, preferred that the entire rack system could be a singular 'bushing that is slid onto a first articulation bushing (described below as first articulation bushing 526). In this case, there would only be a "first rack" (e.g., first rack 514) in the embodiment, with a lumen 530 (see FIG. 17) extending therethrough to engage with the first articulation bushing 526. In this implementation, the outside surface of the first rack 514 includes rack gearing 520 that enables axial translation of the first rack 514 (e.g., distal and proximal along the shaft 604); the rack gearing 520 being positioned opposite the first rack gearing 516. An example of this implementation with a single rack 518 is shown in the cross-sectional view of FIG. 49B.

Figures 18, 19:
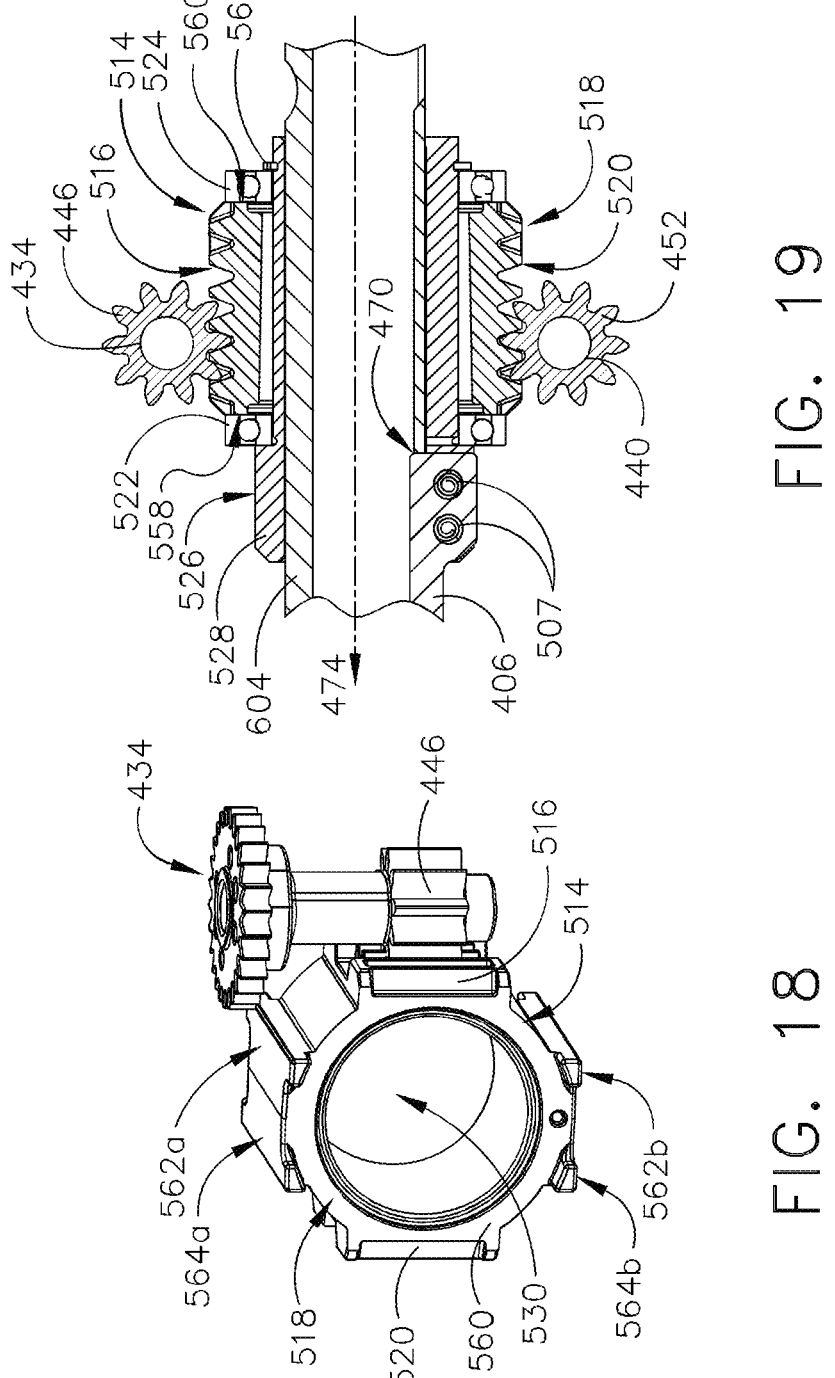
FIG. 18 is a perspective view of a portion of an "inboard" articulation subsystem, according to aspects of the present disclosure.
FIG. 19 is a top cross-sectional view of an "inboard" articulation subsystem, according to aspects of the present disclosure.

To account for the rotation of the shaft 604, the articulation subsystem 400 shown in FIG. 16 includes a first articulation bushing 526 that is rotatable with the shaft 604, and is rotatably independent of the first rack 514 (and second rack 518 if present). In other words, the rolling of the shaft 604 will also roll the first articulation bushing 526, all while the first rack 514 remains rotationally stable within the outer housing 102. The first articulation bushing 526 can slide from a first position to a second position along a longitudinal axis 474 of the rotatable shaft 604, thereby moving the articulation rod 406 proximally and distally. The first rack 514 can have a first housing track surface 562 that moves axially within a corresponding track in the outer housing 102, thereby enabling the first rack 514 to slide axially but not rotationally. If a second rack 518 is present, the second rack 518 can have a first housing track surface 564 adjacent the first housing rack surface 562 that moves axially within a corresponding track in the outer housing 102, thereby enabling the second rack 518 to slide axially but not rotationally. FIGS. 49A and 49B show the tracks 176A, 176B through which the rack 514 can track. As shown, both tops and bottoms of the first rack 514 can have a first housing track surface 562, which are shown in FIG. 18 labeled as first housing track surfaces 562a and 562b. If a second rack 518 is present, both tops and bottoms of the second rack 518 can have a second housing track surface 564, which are shown in FIG. 18 labeled as second housing track surfaces 564a and 564b. Again, these track surfaces 562 and/or 564 can travel within the housing 102 (see again FIGS. 49A and 49B).

Unlike in the "outboard" design shown in FIGS. 12-15, the example shown in FIGS. 16-19 show only a single first articulation bushing 526. The shape of this first articulation bushing 526 is best shown in the cross section of FIG. 19. The first articulation bushing 526 is slid onto the shaft 604. The first rack 514 (and the second rack 518 if present) is secured with respect to the first articulation bushing 526 via a first articulation bearing 522 and a second articulation bearing 524. The first articulation bearing 522 is constrained distally by a flange 528, and the second articulation bearing 524 is constrained proximally by a locking ring 568. Constrained as such, movement of the first rack 514 and/or the second rack 518 can cause the first articulation bushing 526 to move axially, as described herein. The distal end of the first rack 514 (and the second rack 518) has a first bearing surface 558 that abuts the flange 528, and the proximal end of the first rack 514 (and the second rack 518) has a second bearing surface 560. As can be seen in FIG. 19, the one or more racks 514, 518 themselves do not need to touch the first articulation bushing 526, and decoupling the one or more racks 514, 518 from the first articulation bushing 526 can reduce wear on those parts. Instead, the one or more racks 514, 518 can contact the respective bearings 522, 524, and the bearings 522, 524 contact the first articulation bushing 526.

Regarding the relative movement of the rack gears 434, 440 and the respective racks for each design, the movement of the rack gears 434, 440 (or initially the movement of the first articulation input puck 402 and/or second articulation input puck 404 that results in the movement of the rack gears) can be used to share load and/or create antagonistic compression at the bushings. To illustrate using the views in FIGS. 14 and 15, or the "outboard" configuration, the surgical instrument 100 can create antagonistic compression of the articulation bushings 426, 428. For example, the rack gears 434, 440 can maintain a force that causes compression of the articulation bushings 426, 428 towards each other. Maintaining this antagonistic compression can reduce lash between the rack gear teeth 446, 452 and the respective rack gearing 416, 420. In FIGS. 16-19, or the "inboard" configuration, the first rack 514 and the second rack 518 share loads and do not act antagonistically. However, that does not preclude the example shown in FIGS. 16-19 from using antagonistic options to reduce lash or, in some examples, allow one of the two pucks to act as an articulation brake by counteracting the torque of the other puck.

The proximal end 470 of the articulation rod 406 can include a hook 407 or other attachment that constrains the articulation rod 406 proximally between the articulation bushings 426, 428, as shown in FIGS. 12-15. In other examples, the proximal end 470 of the articulation rod 406 can be coupled to the first articulation bushing 526 via one or more pins 507 (see FIG. 19). The pins 507 can attach the articulation rod 406 to the flange 528. As mentioned above with respect to the outboard configuration, the inboard configuration is designed such that movement of the first articulation bushing 526 effects articulation of the end effector 150 (see FIGS. 22-24). FIG. 19 shows how articulation of the rack gears 434, 440 can impart a force onto the individual racks 514, 518 to move the first articulation bushing 526. To move the first articulation bushing 526, the first rack gear 434 can rotate in a first angular direction, and the first rack gear teeth 446 move through the first rack gearing 516 of the first rack 514. Movement of the first rack 514 distally (by first rack gear 434 turning clockwise in FIG. 19) causes the first articulation bushing 426 to translate distally along the longitudinal axis 474 of the shaft 604. In turn, the articulation rod 406 will translate distally, thereby pivoting the distal channel retainer 408 such that the end effector 150 pivots, in this example to the right. The first rack gear 434 can rotate in a second angular direction (opposite the first angular direction described above), and the first rack gear teeth 446 move through the first rack gearing 516 of the first rack 514. In turn, the articulation rod 406 will translate proximally, thereby pivoting the distal channel retainer 408 such that the end effector 150 pivots, in this example to the left. When the second rack 518 and second rack gear 440 are employed, rotation will be opposite of the first rack 514 and first rack gear 434. For example, if the first rack gear 434 rotates clockwise to move the first rack 514 distally, the second rack gear 440 rotates counterclockwise to move the second rack 518 distally. In this example, therefore, the first rack gear 434 and the second rack gear 440 act to share the load, providing a greater articulation force for the end effector 150.

Figure 20:
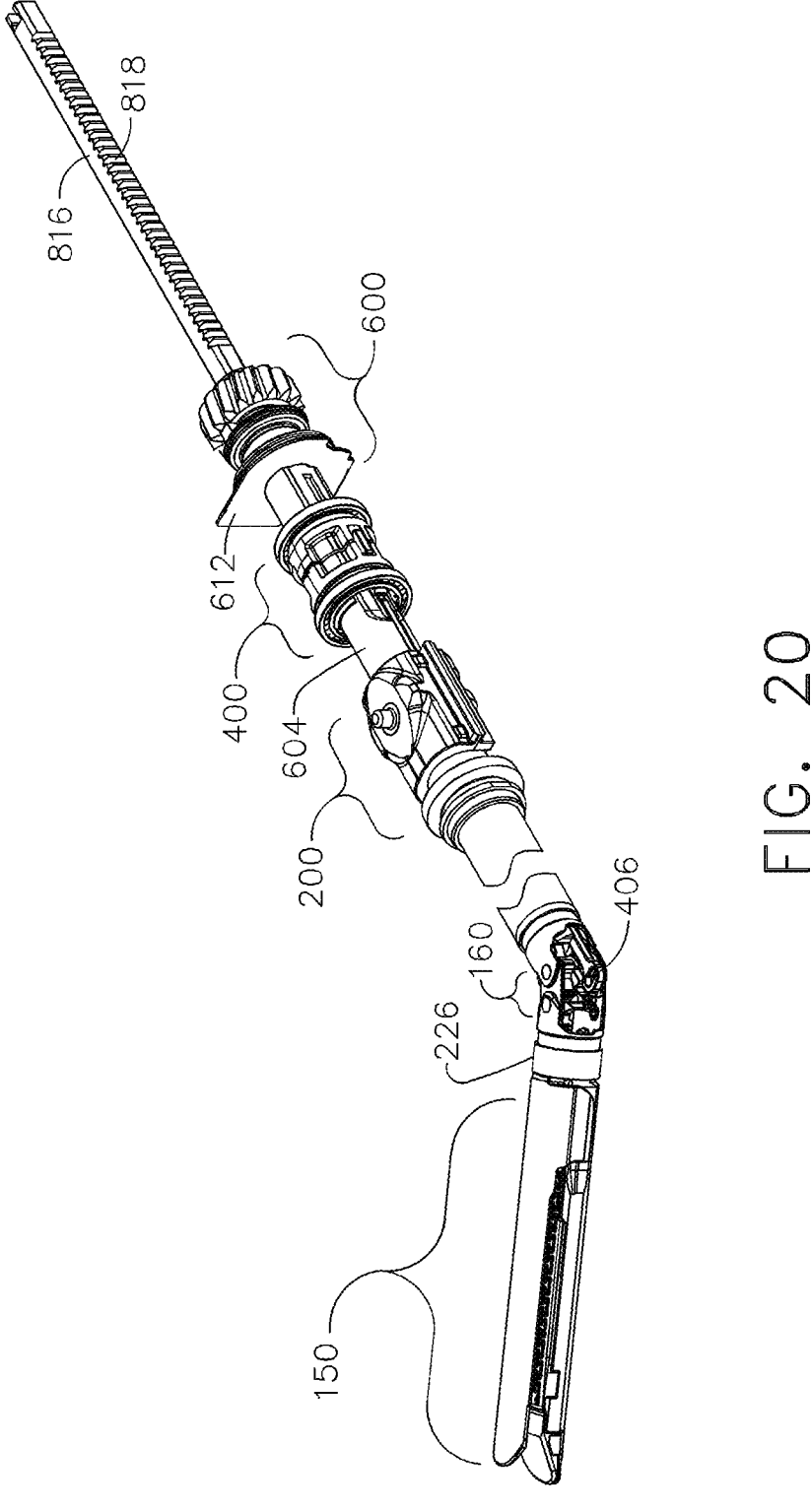
FIG. 20 shows components of a surgical instrument with an end effector being articulated, according to aspects of the present disclosure.
Figure 21:
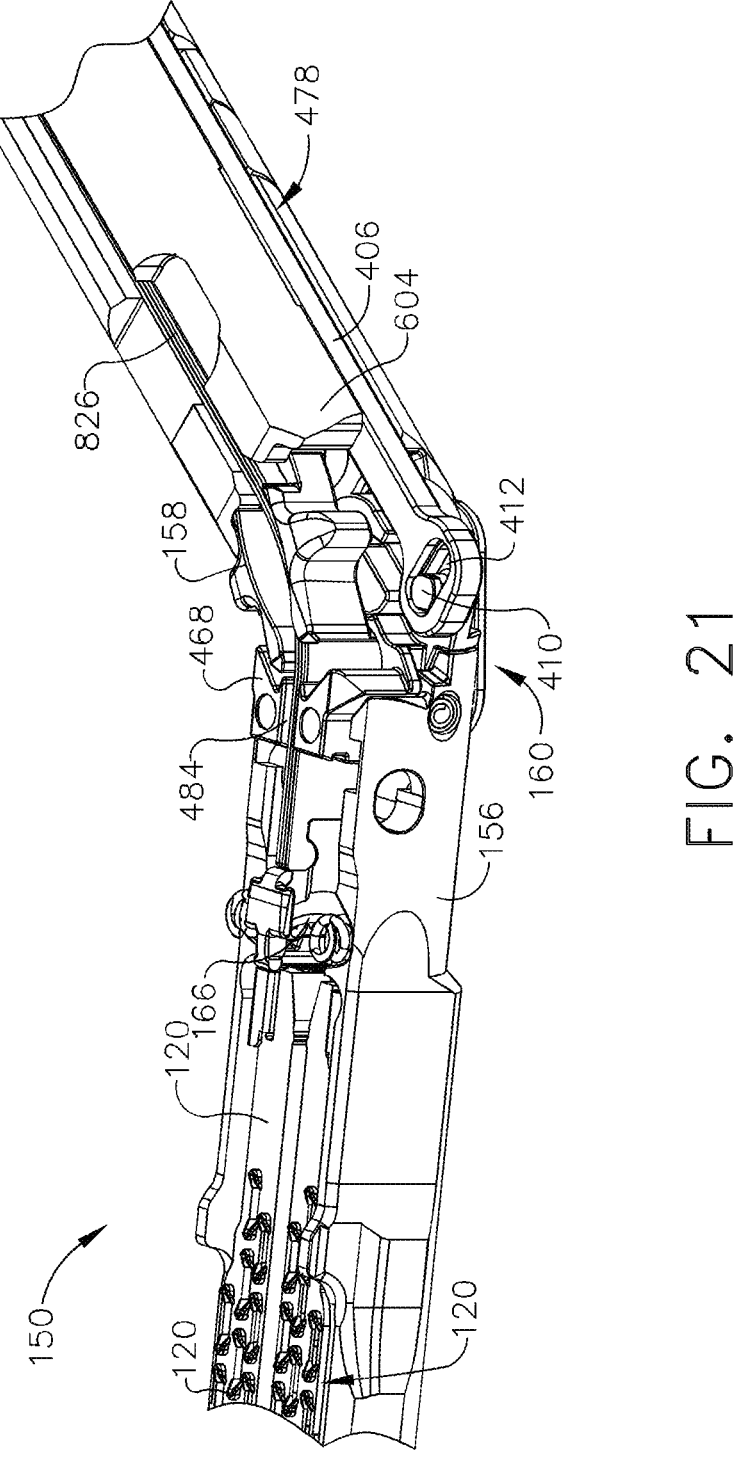
FIG. 21 shows articulation of an end effector relative to a shaft, according to aspects of the present disclosure.
Figure 22:
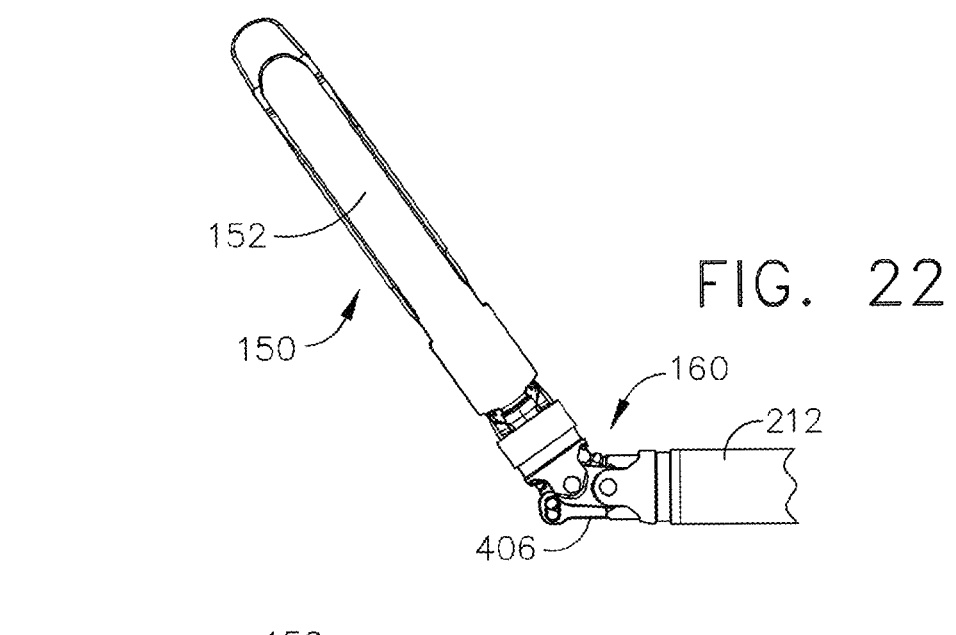
FIGS. 22-24 show articulation of an end effector relative to a shaft, according to aspects of the present disclosure

FIG. 20 shows the surgical instrument articulated to the right. FIG. 21 provides a detailed view of the articulating components of the surgical instrument 100. FIG. 22 shows the end effector 150 articulated to the right, FIG. 23 shows the end effector 150 without being articulated, and FIG. 24 shows the end effector 150 articulated to the left. In some examples, the articulation subsystem 400 described herein can achieve at least 60° of articulation in either direction, for example ±5°, ±10°, ±15°, ±20°, ±25°, ±30°, ±35°, ±40°, ±45°, ±50°, ±55°, ±60°, or any intervening degree of articulation back and forth. It will be noted that the joint 160 shown in FIGS. 22-24 that holds the end effector 150 to the shaft 604 is exposed for visualization. The joint 160 can be concealed by a flexible sheath 174 (see FIG. 1) to alleviate pinch points. The joint 160 described herein can include multiple articulation links that connect the closure tube 212 to the closure ring 226. This linking system can be a boss/hole configuration that provides a pinned joint. The exterior closure system can consist of the closure tube 212 pushing distally forward on the two articulation links of the joint 160, which in turn push on the closure ring 226.

Roll Subsystem

Figure 26:
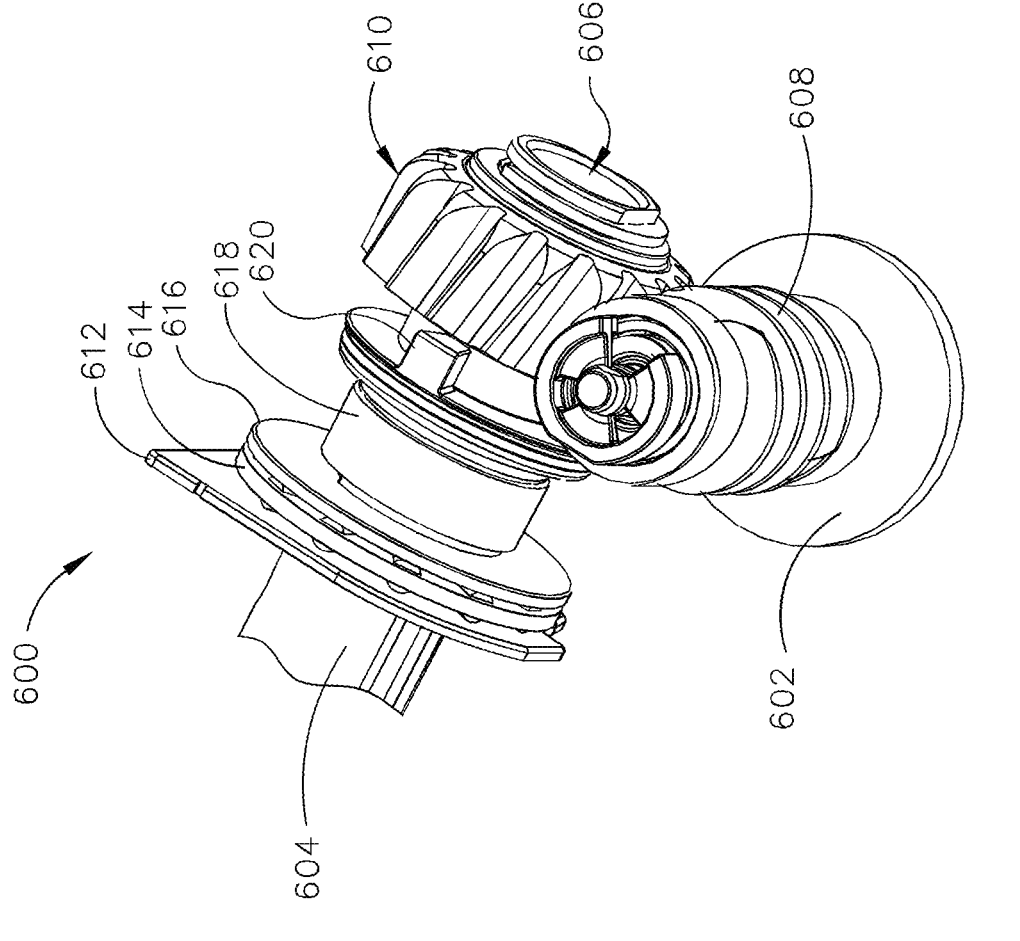
FIGS. 26-27 show components of a roll subsystem, according to aspects of the present disclosure.
Figure 48B:
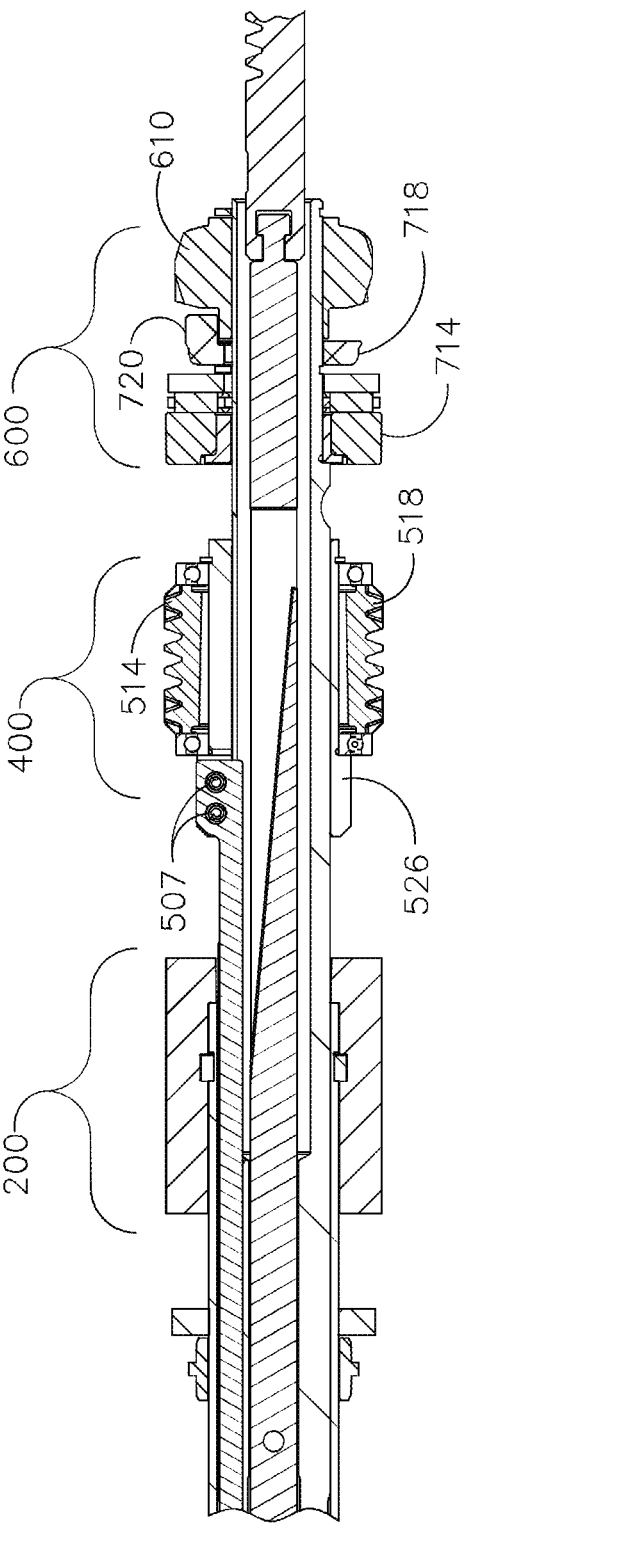
FIG. 48B is a top cross-sectional view of a closure subsystem, an articulation subsystem (inboard), a roll subsystem, and portions of a transection subsystem for a surgical instrument, according to aspects of the present disclosure.

The surgical instrument 100 includes a roll subsystem 600. Detailed views of the proximal portions of an example roll subsystems 600 are provided in FIGS. 26-32D, whereas more distal portions of the example roll subsystem 600 are shown in FIG. 40. Referring specifically to FIG. 26, the roll subsystem 600 includes a series of gears that allow the shaft 604 to rotate around its longitudinal axis 474. The shaft 604 can be directly connected to the end effector 150, and therefore rolling of the shaft 604 enables the end effector 150 to roll the single articulation plane to any orthogonal position. The shaft 604 includes a shaft lumen 606 extending therethrough, and distal portions of a transection subsystem 800 extend through the shaft lumen 606 (see FIG. 48A for outboard example, FIG. 48B for inboard example). The transection subsystem 800 is described in greater detail below.

The roll subsystem 600 includes a roll input puck 602 that is engageable with a corresponding rotatable robotic output (e.g., roll robotic output 910 in FIG. 2). The roll input puck 602 can be rotationally engaged with a worm gear 608 extending therefrom, such that rotation of the roll input puck 602 turns the worm gear 608. Since the roll input puck 602 is positioned perpendicular to the length of the surgical instrument 100, and therefore perpendicular to the shaft 604, the roll subsystem 600 includes a worm follower 610 that is engaged with the worm gear 608. The worm follower 610 can be coupled to the shaft 604, allowing rotation of the shaft 604. To keep the worm follower 610 positioned at the correct location relative to the worm gear 608, the roll subsystem 600 can include a stabilization plate 612 that surrounds the shaft 604 distal to the worm follower 610. The stabilization plate 612 can be positioned within a corresponding slot within the outer housing 102 to prevent the stabilization plate 612 from sliding axially along the shaft 604, while also providing the shaft 604 lateral alignment within the housing 102. The roll subsystem 600 can also include a roll bearing 614 and a roll bearing plate 616, the roll bearing 614 being positioned between the stabilization plate 612 and the roll bearing plate 616.

In some examples, the roll subsystem 600 includes a roll stop bushing 618 engaged with the rotatable shaft 604. The roll stop bushing 618 can be coupled to the worm follower 610 and/or shaft 604 and provide feedback on positioning of the rotatable shaft 604. For example, the roll stop bushing 618 can include a stop 620 positioned thereon that can contact a housing tab 626 positioned on the outer housing 102. The roll subsystem 600 can roll the shaft 604 to a first position where the roll stop bushing 618 contacts the housing tab 626 at a first side, and then roll the roll the shaft 604 to a second position where the roll stop bushing 618 contacts the housing tab 626 at a second, opposite side. The robotic output that actuates the roll subsystem 600 can use the hard stops at the housing tab 626 to determine a baseline, or 0°, rotation for the shaft 604. This example can provide the shaft 604 greater than 300° of rotation, for example greater than 305°, greater than 310°, greater than 315°, greater than 320°, greater than 325°, greater than 330°, greater than 335°, greater than 340°, greater than 345°, greater than 350°, greater than 355° of rotation, or more.

Figure 27:
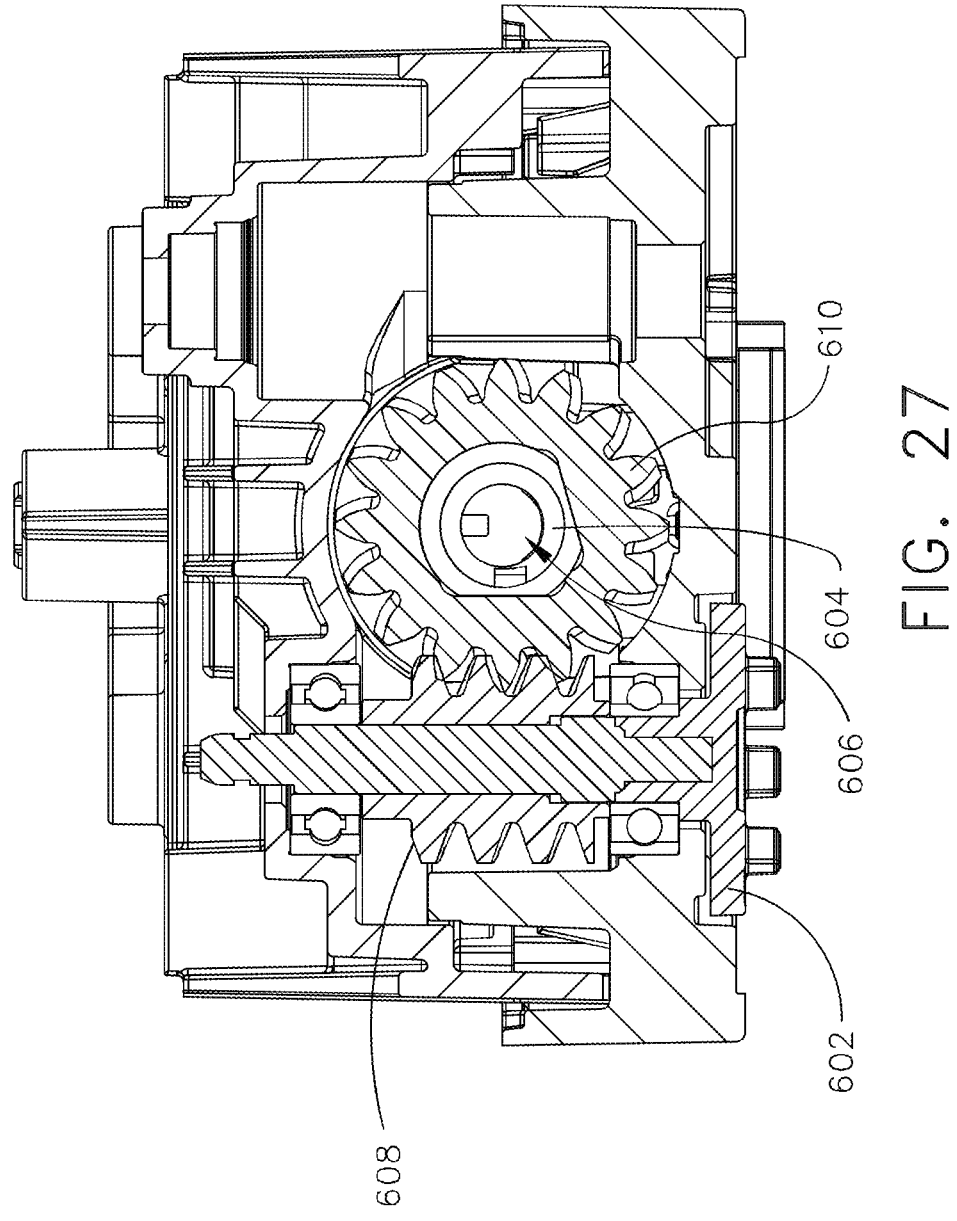
Figure 29:
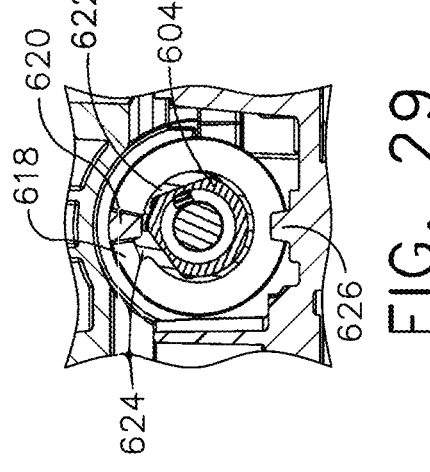
FIGS. 28-30 are end views of bushings for a roll subsystem, according to aspects of the present disclosure.
Figure 30:
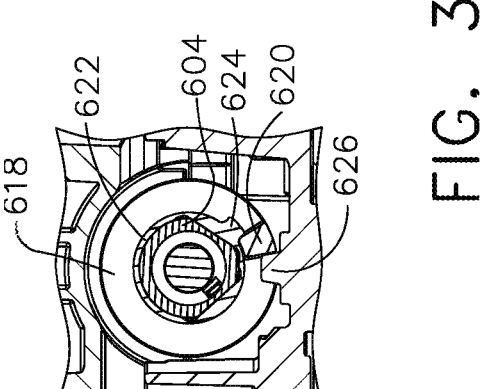
Figure 28:
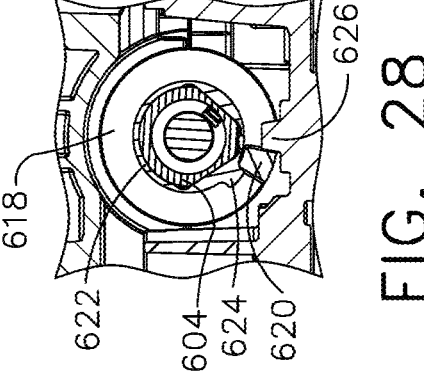

In some examples, and as shown in FIG. 27, the roll subsystem 600 can also include a follower bushing 622 having a follower bushing stop 624 extending therefrom. In this example, the follower bushing 622 can be positioned between the shaft 604 and the roll stop bushing 618. The shaft 604 and follower bushing 622 can be directly coupled to each other, and the roll stop bushing 618 and the follower bushing 622 can rotate relative to each other. The roll subsystem 600 can roll the shaft 604 to a first position where the roll stop bushing 618 contacts the housing tab 626, and the follower bushing 622 contacts the roll stop bushing 618 at a first side (see FIG. 28). The roll subsystem 600 can then rotate the shaft 604 until the follower bushing 622 contacts the roll stop bushing 618 at the other side, and then continue rotating by pushing the roll stop bushing 618 circumferentially (see FIG. 29) until the roll stop bushing 618 contacts the housing tab 626 and the follower bushing 622 contacts the roll stop bushing 618 at a second, opposite side (see FIG. 30). This example using the follower bushing 622 can provide a greater degree of rotation, for example greater than 360° of rotation, or in some instances about 320° of rotation in either direction (e.g., 640° in total). Referring briefly to FIG. 40, which shows distal portions of the roll subsystem 600, the view shows how the rod groove 478 of the shaft 604 can extend along the length of the shaft 604. The articulation rod 406 can extend through the rod groove 478 of the shaft 604, and rotation of the shaft 604 by the roll subsystem 600 can therefore rotate the articulation rod 406.

Figure 31B:
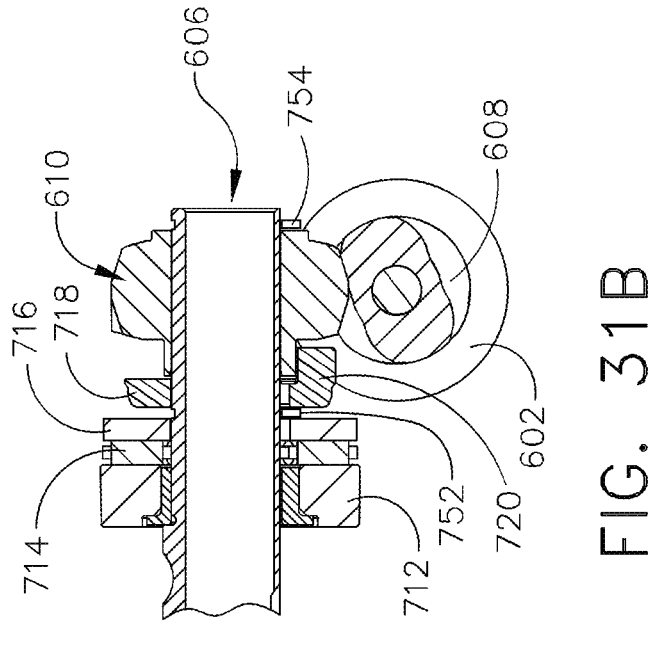
FIGS. 31A and 31B show alternative components of a roll subsystem, according to aspects of the present disclosure.
Figure 31A:
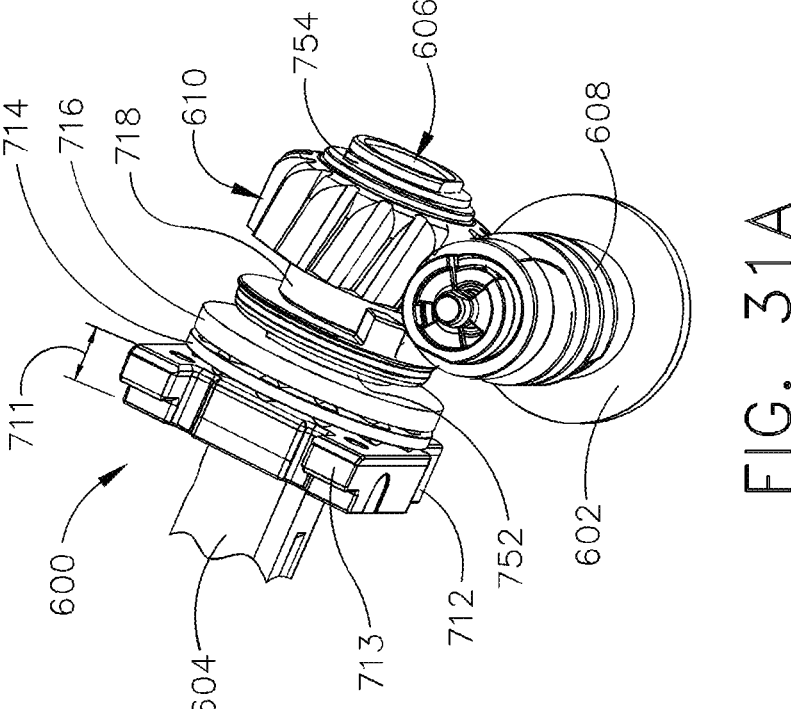
Figure 49C:
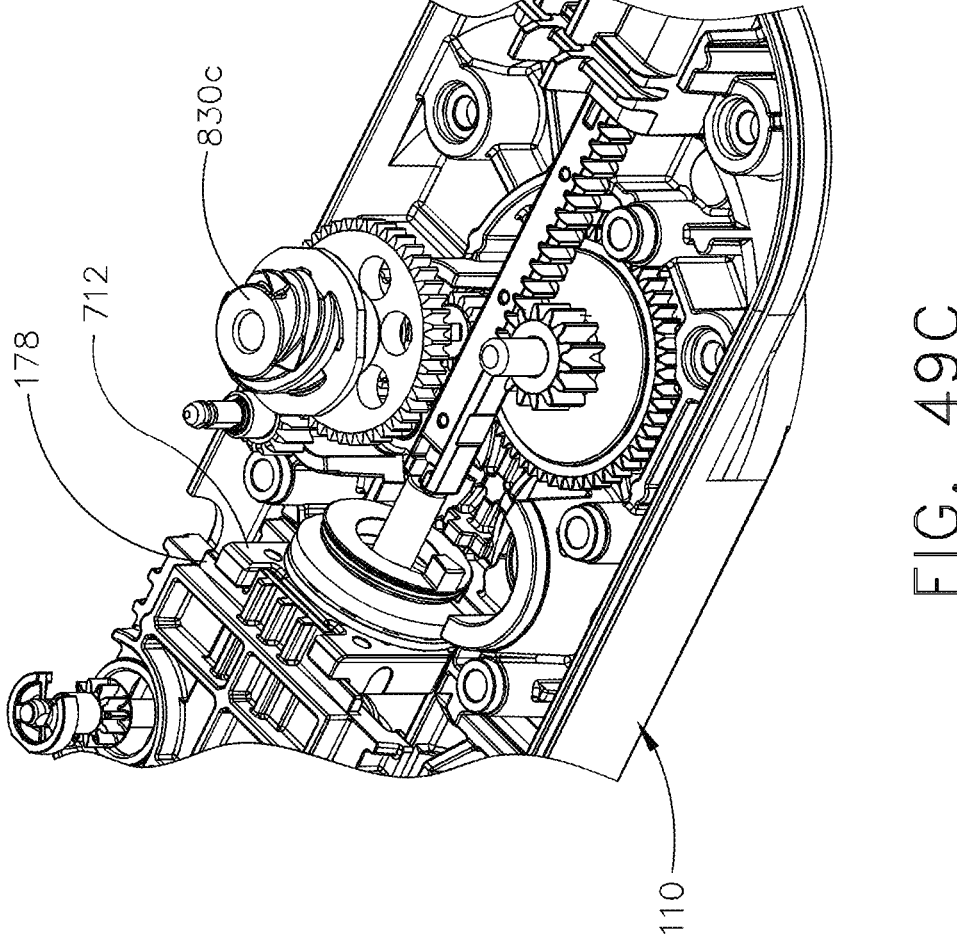
FIG. 49C is a perspective view of a portion of a transection subsystem and roll subsystem, with a thrust block engaged with a buttress portion of the housing, according to aspects of the present disclosure.

FIGS. 31A and 31B show alternative components of a roll subsystem 600 to the one shown in FIGS. 26 and 27, according to aspects of the present disclosure. FIG. 31A is a perspective view of the components of the roll subsystem 600. In the embodiment shown, the stabilization plate 612 shown in FIG. 26 has been replaced with a thicker thrust block 712. The thrust block 712 is positioned near the proximal end of the shaft 604 so as to counteract axial forces on the shaft 604 caused by distal movement of the closure tube 212 (see FIG. 1). Providing a more robust thrust block 712, including a thickness 711 greater than 1.0 cm, or greater than 1.5 cm, can provide better loading scenarios (to stop deflection) and can better share the load with the housing 102. The thrust block 712 can engage with a buttress 178, such as the buttress 178 shown in FIG. 49C. FIG. 31A shows additional components that can be included in the alternative design, including a roll bearing 714, which can be substantially similar to the roll bearing 614 in FIG. 26, and a roll bearing plate 716, which can be substantially similar to the roll bearing plate 616 in FIG. 26 (in FIG. 31A, the bearing plate 716 is thicker than the roll bearing plate 616 to further add to the robustness and load sharing at this component). FIG. 31A also shows a roll stop bushing 718, which can be substantially similar to roll stop bushing 618. FIG. 31B is a top, cross-sectional view of the components of the roll subsystem 600. The subsystem can include a first locking ring 752 and a second locking ring 754. The locking rings 752, 754 can be positioned such that they secure the worm follower 610 and the roll stop bushing 718 together. The stop 720 of the roll stop bushing 718 is also shown; the stop 720 can be substantially similar to stop 620 described above.

Figures 32A, 32B, 32C, 32D:
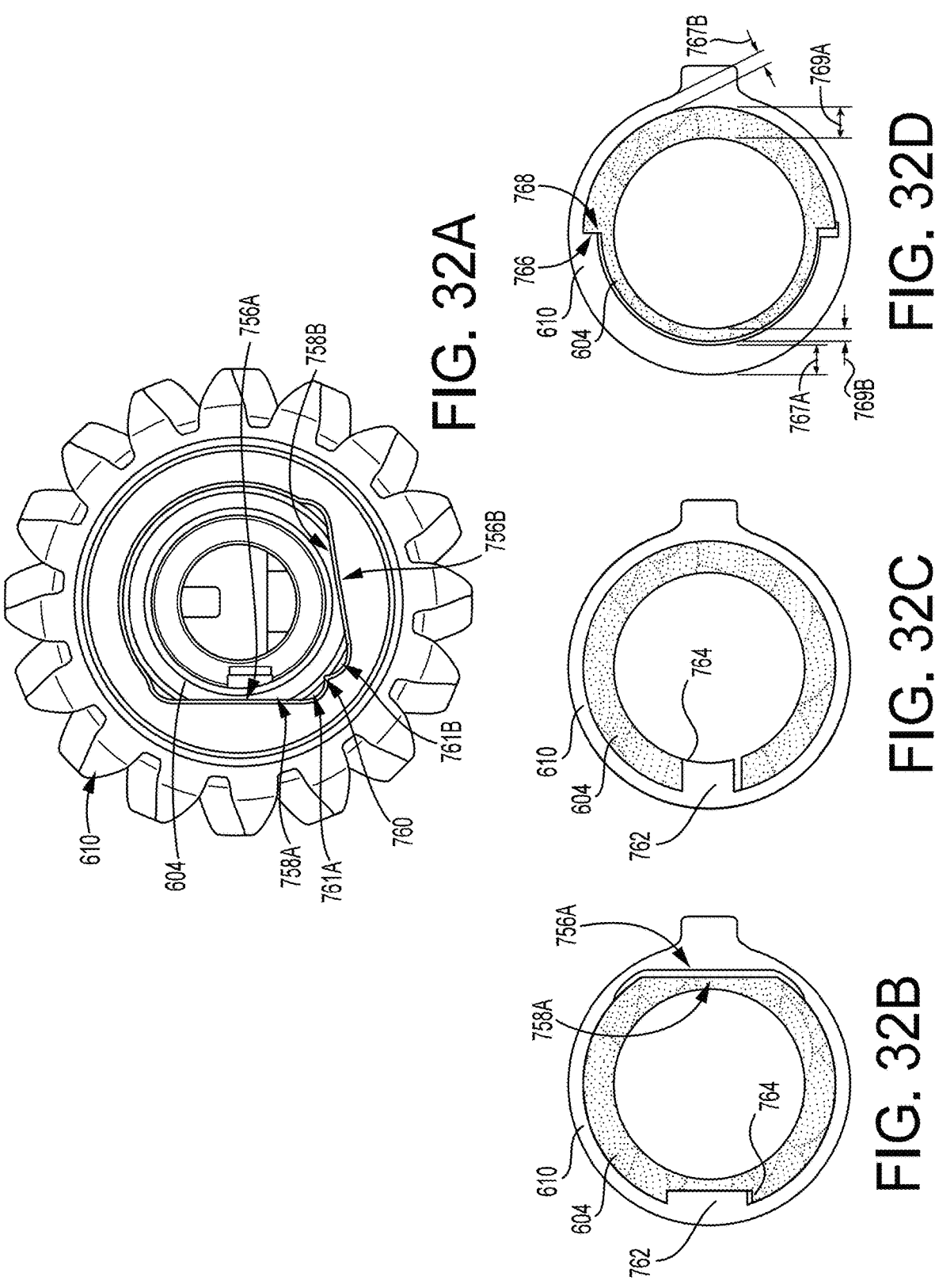
FIGS. 32A-32D provide examples of anti-backlash features for a worm follower engaged with a rotatable shaft, according to aspects of the present disclosure.

Referring to FIG. 27 for reference, as shown, the inside of the worm follower 610 may not be entirely round and, similarly, the outside surface of the shaft 604 may not be entirely round. Instead, the worm follower 610 and the shaft 604 can have corresponding anti-backlash features. It is desirable to reduce backlash in the gearing of a surgical instrument 100 to improve accuracy and to ensure proper calibration. For instance, a robot can home and/or calibrate roll by rolling the shaft 604 from one mechanical calibration position to another mechanical calibration position (see FIGS. 28-30 for a discussion of rotational constraints for the roll subsystem 600). Therefore, backlash reduction can help to ensure accurate calibration. The implementations shown in FIGS. 32A-32D provide examples of such anti-backlash features. FIG. 32A is a detailed view of the system also shown in FIG. 27. Here, the inside area of the worm follower 610 (i.e., the portion engaged with the shaft 604) includes one or more gear flats 756. A gear flat 756 can be used to ensure that the worm follower 610 constrains the shaft 604 so that they rotate together. The one or more gear flats 756 are positioned to abut and/or contact one or more corresponding shaft flats 758 on the exterior surface of shaft 604. In the example shown, the worm follower 610 comprises a first gear flat 756A and a second gear flat 756B, and the rotatable shaft 604 comprises (i) a first shaft flat 758A positioned to correspond to the first gear flat 756A and (ii) a second shaft flat 758B positioned to correspond to the second gear flat 756B. Having more than one flat can further limit backlash between the two components. In certain implementation, the first gear flat 756A can coincide with the portion of the shaft 604 that houses the rod groove 478 (see, e.g., FIG. 7A).

The one or more gear flats 756 may be milled, broached, or otherwise formed into the worm follower 610 and, as such, tight corners between the flat and curved section may not be possible or may not be desired, for instance because abrupt corners could be a location for stress fractures. Accordingly, the transitions between the one or more gear flats 756 and the curved section so as to provide gaps between the worm follower 610 and the shaft 604 at certain positions. Two such gaps are shown in FIG. 32A and are labeled as first gap 761A and second gap 761B. A first end of the first gear flat 756A is rounded and inwardly turned so as to come to a singular point 760. A first end of the second gear flat 756B is rounded and inwardly turned so as to come to the singular point 760. A portion of the worm follower 610 between the first gear flat 756A and the singular point 760 is separated from the rotatable shaft 604 by the aforementioned first gap 761A. A portion of the worm follower 610 between the second gear flat 756B and the singular point 760 is separated from the rotatable shaft 604 by the second gap 761B. The singular point 760 contacts the rotatable shaft 604 to provide the circumferential control of the shaft 604 within the worm follower 610.

FIGS. 32B-32D show additional or alternative anti-backlash features for the worm follower 610 and shaft 604. In FIG. 32B, the worm follower 610 includes a key 762 that engages with a keyway 734 in the shaft 604. Alternatively, the shaft 604 could include the key and the worm follower 610 the keyway. In some examples, the key/keyway could be combined with one of the other anti-backlash features, such as first shaft flat 758A and first gear flat 756A, as shown. In FIG. 32C, the example shown also includes a key 762 and a keyway 734, but the keyway 734 extends entirely through the wall of the shaft 604. In FIG. 32D, the worm follower 610 has different wall thickness, as measured to the inside surface of the worm follower 610 that contacts the shaft 604. The worm follower 610 has a first portion with a first wall thickness 767A and a second portion with a second wall thickness 767B, the first wall thickness 767A being thicker than the second wall thickness 767B. This change in the interior wall geometry thereby forms a gear step 766. Similarly, the rotatable shaft 604 has a first portion with a first wall thickness 769A and a second portion with a second wall thickness 769B, the first wall thickness 769A being thicker than the second wall thickness 769B. This change in the interior wall geometry of the shaft 604 thereby forms a shaft step 768. The gear step 766 is sized and positioned to engage with the shaft step 768 to reduce backlash as the worm gear 608 actuates the worm follower 610. It is also contemplated that the worm follower 610 and shaft 604 are inseparably connected, such as with a weld or adhesive, though manufacturing a connected embodiment may take additional steps in manufacturing.

Figures 33A, 33B:
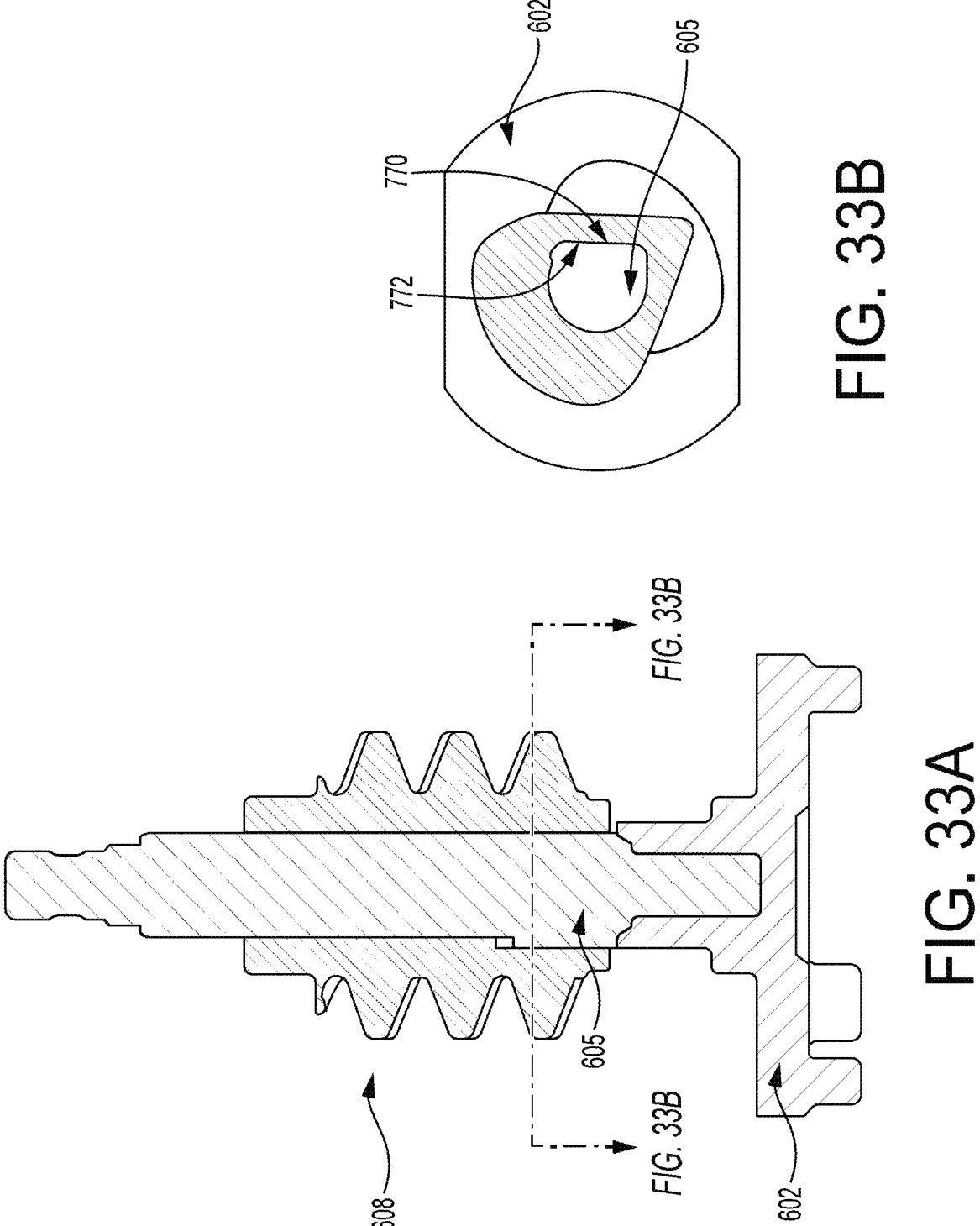
FIGS. 33A and 33B show example anti-backlash features for a worm gear, according to aspects of the present disclosure.

FIGS. 33A and 33B show example anti-backlash features for a worm gear 608, according to aspects of the present disclosure. The disclosure above discussed reducing backlash at the connection between the shaft 604 and worm follower 610, but another point of potential backlash in the roll subsystem 600 is where the roll input puck 602 and its respective input shaft 605 engages with the worm gear 608. FIG. 33A shows the placement of the input puck 602, input shaft 605, and worm gear 608, whereas the top FIG. 33B cross sectional view shows the example anti-backlash features. The input shaft 605 extends at least partially through the worm gear 608. The input shaft 605 includes a flat section 772 positioned to correspond to a worm drive flat 770 of the worm gear 608. This flat-on-flat feature is similar to the gear flats 756 and shaft flats 758 discussed with respect to FIG. 32A.

Transection Subsystem

Figure 34:
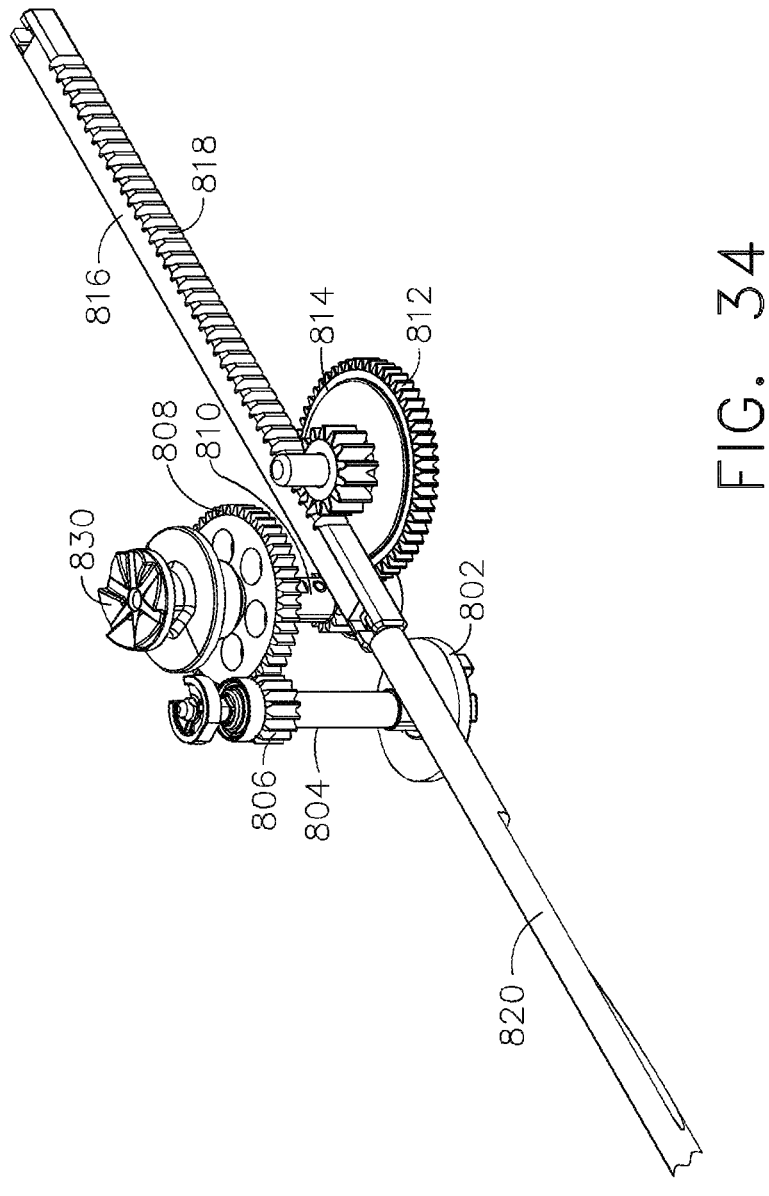
FIG. 34 shows components of a transection subsystem, according to aspects of the present disclosure.

The surgical instrument 100 includes a transection subsystem 800. This subsystem can be referred to as a transection subsystem since actuation of the system results in a cutting of tissue via cutting mechanisms of the end effector 150, mechanisms of which are described in more detail below. The transection subsystem 800 includes a series of gears proximally that allow the system to fire a firing rack 816 distally. Because the surgical instrument 100 can have a roll feature, e.g., via the roll subsystem 600, the proximal portion of the transection subsystem 800 (e.g., with the gearing and firing rack 816, see FIGS. 34-37) is not rotatable, but the distal end (e.g., firing rod 820, bands 826, etc., see FIGS. 38 and 41) can rotate along with the roll of the shaft 604. Referring specifically now to FIG. 34, the transection subsystem 800 includes a transection input puck 802 that is engageable with a corresponding rotatable robotic output (e.g., transection robotic output 912 in FIG. 2). The transection input puck 802 can be rotationally engaged with a transection drive shaft 804 extending therefrom, such that rotation of the transection input puck 802 turns the transection drive shaft 804. Rotation of the transection drive shaft 804 causes, either directly or indirectly via gearing, distal translation of the firing rack 816, which results in firing of the staples 126 and/or knife 166 in the end effector. Although not visible in the figure because they are inside of the cartridge 120, staples 126 are located as indicated in FIG. 44.

Since the distal translation of the firing rack 816 is used to translate a distal knife 166, a higher degree of force is desired for the distal translation. The force needed to push the knife 166 forward can be great, as it can include the accumulation of forces required to cut tissue, drive staples, and interact with any friction. As such, the present disclosure provides a series of gearing to increase the transection, or cutting, force by providing a mechanical advantage past the transection input puck 802. The transection subsystem 800 includes a transection spur gear 806 that is coupled to the transection drive shaft 804 such that rotation of the transection drive shaft 804 also turns the transection spur gear 806. The transection subsystem 800 can include a transection ramp gear 808 that is rotatably engaged with the transection spur gear 806, meaning that rotation of the transection spur gear 806 in a first direction causes a corresponding rotation of the transection ramp gear 808 in the opposite direction.

The transection ramp gear 808 can have a larger diameter than the transection spur gear 806. A ramp gear shaft 810 can be coupled to and extend from the transection ramp gear 808, such that the ramp gear shaft 810 rotates with the rotation of the transection ramp gear 808. A transection ramp spur gear 811 can be coupled to the ramp gear shaft 810 such that the transection ramp spur gear 811 can be caused to rotate when the ramp gear shaft 810 rotates.

The transection subsystem 800 can include a speed gear 812 that is rotatably engaged with the transection ramp spur gear 811, meaning that rotation of the ramp gear shaft 810 in a first direction causes a corresponding rotation of the speed gear 812 in the opposite direction. The speed gear 812 can have a larger diameter than the ramp gear shaft 810 and the transection ramp gear 808. The transection spur gear 806, transection ramp gear 808, transection ramp spur gear 811, and speed gear 812 shown in FIG. 34 are all spur gears.

The transection subsystem 800 includes a firing gear 814 that is rotationally dependent on the gearing, for example rotation of the firing gear 814 is ultimately dependent on rotation of the transection input puck 802. In the examples with a speed gear 812, the firing gear 814 can be rotatable with rotation of the speed gear 812. The firing gear 814 is engaged with teeth 818 of the firing rack 816, such that rotation of the firing gear 814 causes a distal translation of the firing rack 816. As will be appreciated, the differences in gear sizes of the transection subsystem 800 can increase the linear velocity of the firing rack 816.

Figure 41:
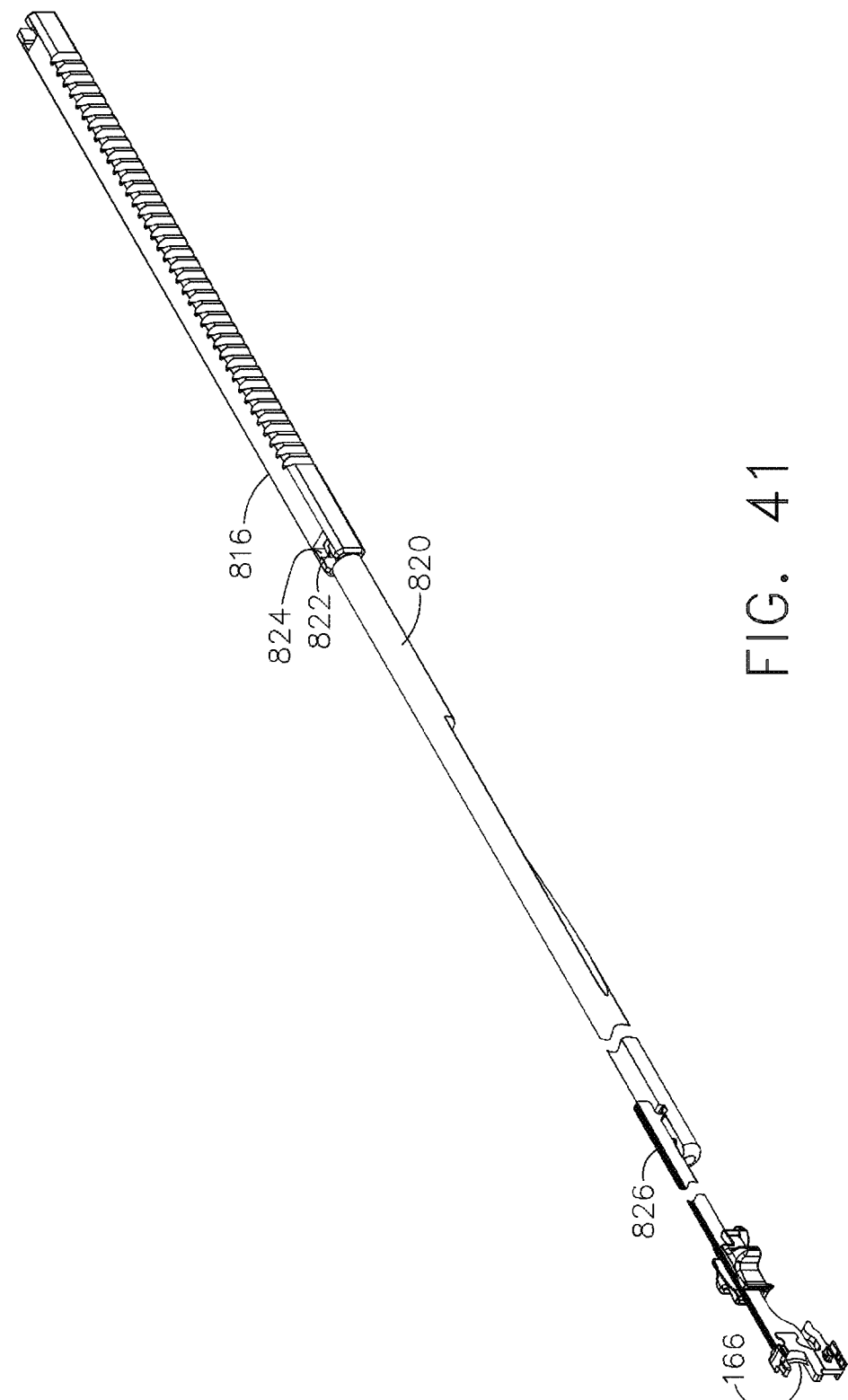
FIG. 41 shows shaft transection (e.g., firing) components of a surgical instrument, according to aspects of the present disclosure.
Figure 52:
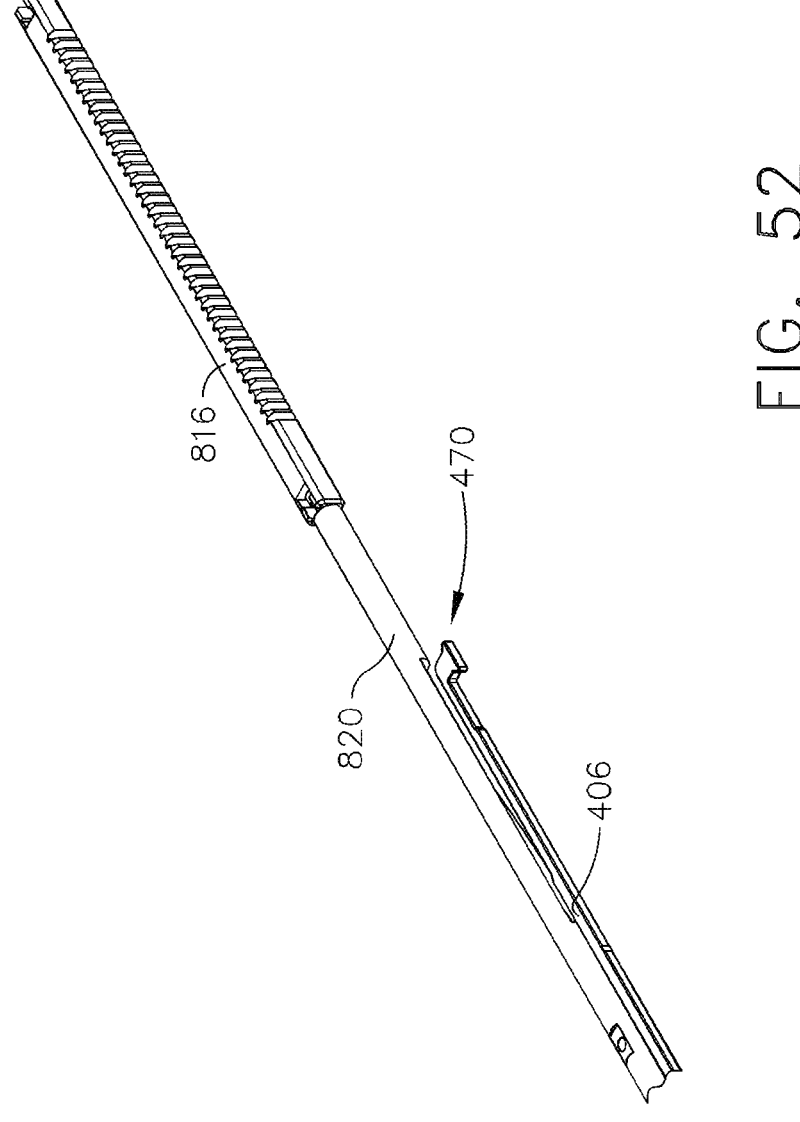
FIG. 52 shows an articulation rod, a firing rack, and a firing rod of a surgical instrument, according to aspects of the present disclosure.

As described above, the firing rack 816 can be rotationally stable within the outer housing 102, but because the more distal end of the transection subsystem 800 must rotate with the roll features of the roll subsystem 600, the distal portion of the transection subsystem 800 can rotate independent of the firing rack 816. The transection subsystem 800 can have a firing rod 820 rotatably coupled to the distal end of the firing rack 816, such that the firing rod 820 can rotate independent of the firing rack 816. The rotatable connector between the firing rod 820 and the firing rack 816 can include a T-shaped tab 822 on the proximal end of the firing rod 820 that engages with a slot 824 on the firing rack 816. The tab/slot connection allows free rotation of the firing rod 820 but also constrains the firing rod 820 to the firing rack 816 axially. An example of this connection between the firing rod 820 and the firing rack 816 is shown in FIGS. 38 and 41. FIG. 52 shows the firing rack 816, firing rod 820, and articulation rod 406. It will be understood that the T-shaped tab 822 could alternatively be on the firing rack 816 and the slot could be on the firing rod 820.

Referring to FIGS. 38 and 41, which provide a detailed view of certain distal components of the transection subsystem 800, the distal end of the firing rod 820 can be coupled to a series of bands 826 that extend distally toward the end effector 150. These bands provide a degree of flexibility to the firing mechanism, while also providing axial stiffness to push the knife 166 through tissue. The surgical instrument 100 can include a knife insert retainer 838 that protects the bands 826 (see FIG. 38). FIG. 21 further shows the bands 826 distally. The surgical instrument 100 can include knife guide 158 at a joint 160 that allows the end effector 150 to articulate as described herein. The bands 826 can pass through the knife guide 158, and the knife guide 158 provides lateral support to guide the laminates through any articulation angle. The bands 826 can also pass through the band slot 484 of the attachment end 468 of the distal channel retainer 408.

Figures 35, 36, 37:
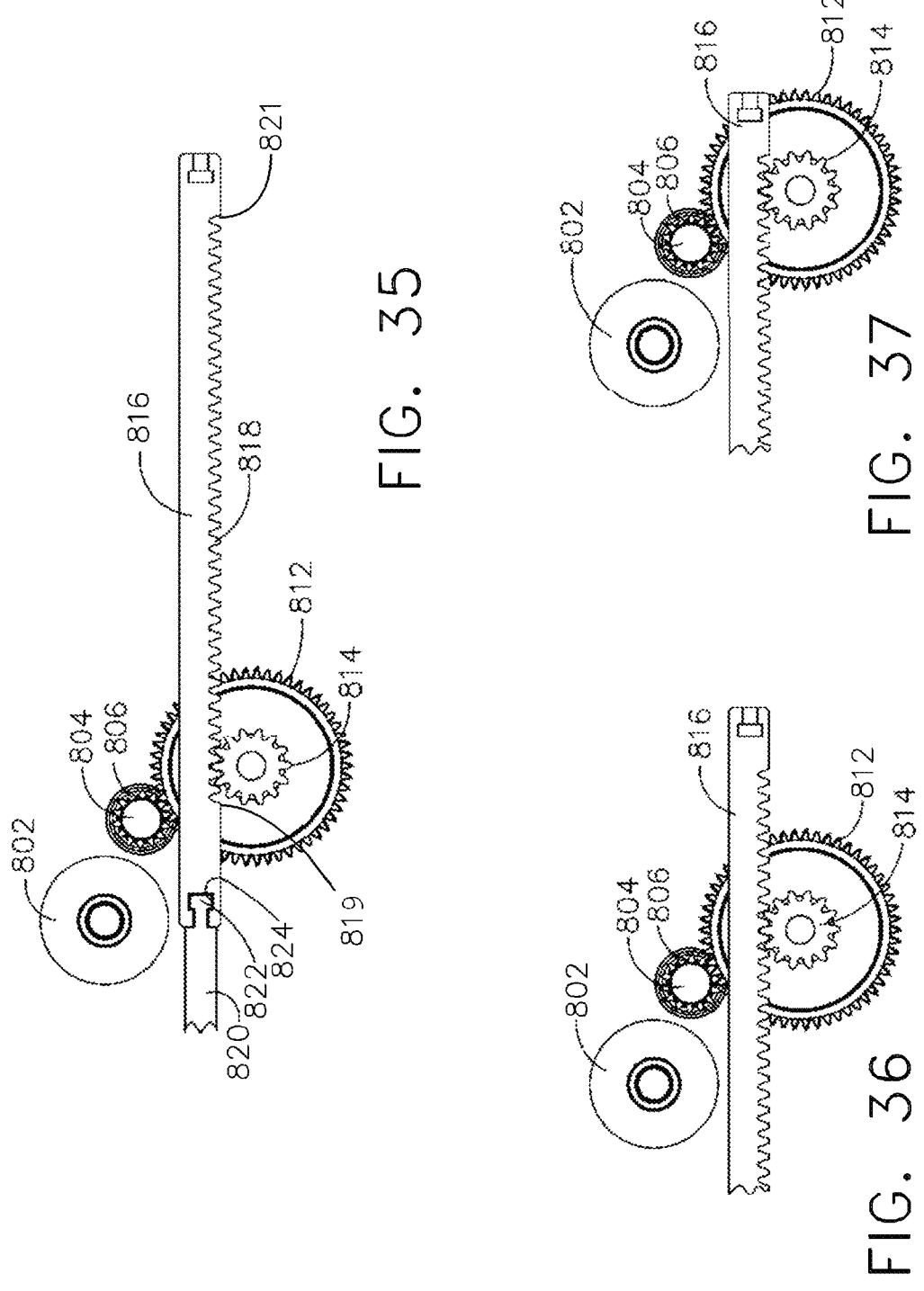
FIGS. 35-37 show components of a transection subsystem during a progressive firing stroke, according to aspects of the present disclosure.
Figure 53:
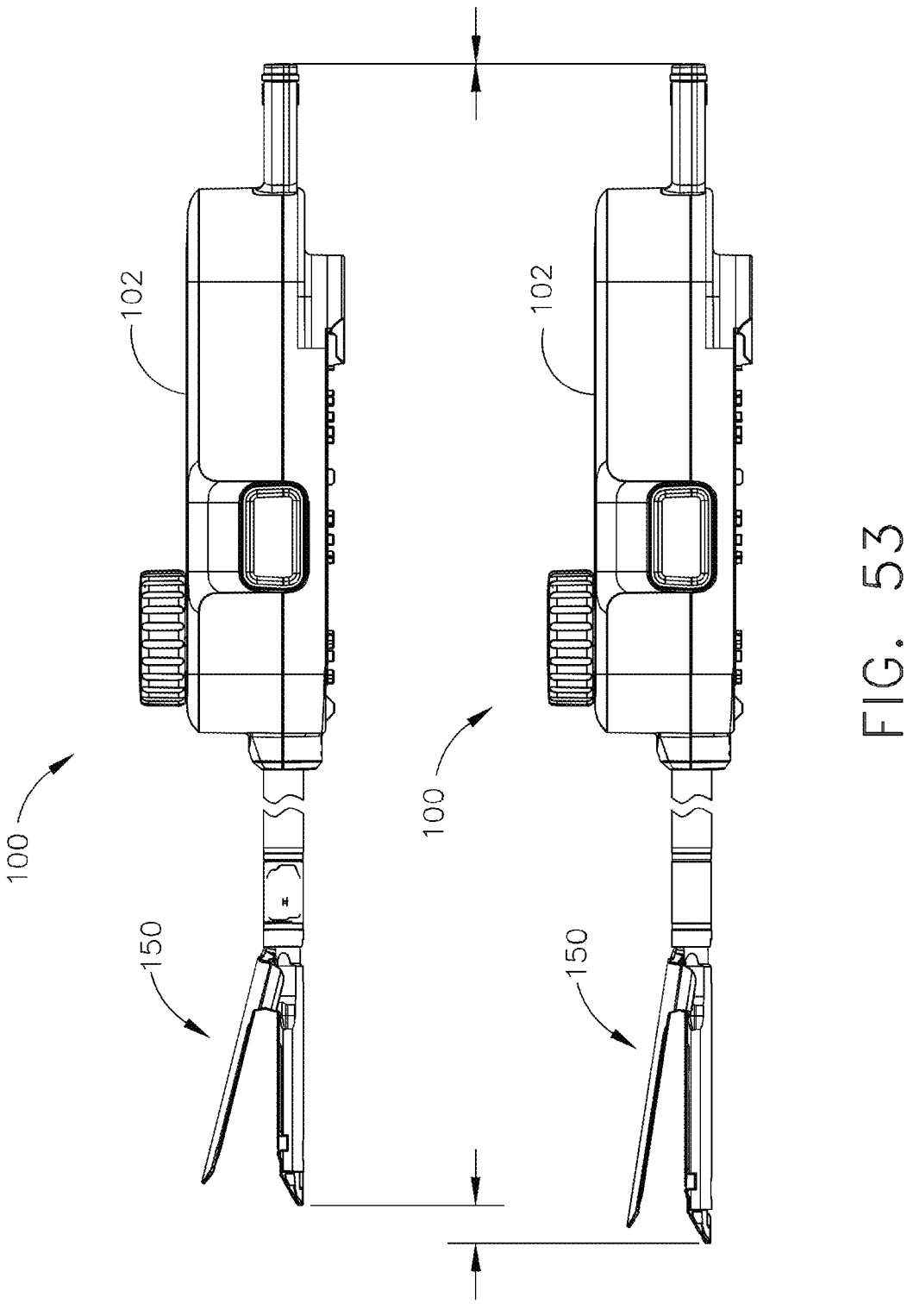
FIG. 53 is a side view of a surgical instruments showing different lengths of devices pursuant to having different length of end effectors or staple cartridges, according to aspects of the present disclosure.

Referring to FIGS. 35-37, the transection subsystem 800 can have a final firing length that is dependent on a length of a staple cartridge 120 within the end effector 150. For example, if a staple cartridge 120 provides 45 mm of cutting/stapling, then the transection subsystem 800 can be configured to translate the firing rack 816 a maximum of 45 mm, as shown in FIG. 36. It will be understood that certain degrees of tolerance can be built in depending on how long the staple cartridge 120 is to deliver 45 mm of staples. If a staple cartridge 120 provides 60 mm of cutting/stapling, then the transection subsystem 800 can be configured to translate the firing rack 816 a maximum of 60 mm, as shown in FIG. 37. FIG. 53 provides a side view of the surgical instrument 100, and shows how the end effectors 150 of different lengths can be used with the same internal components. For example, the top surgical instrument 100 in the figure could be a 45 mm end effector 150, and the bottom surgical instrument 100 in the figure could be a 60 mm end effector 150. FIG. 35 shows the firing rack 816 at a home (e.g., unfired) position. FIG. 35 also highlights two hard stop features of the firing rack 816. More distally is a distal hard stop 819, and more proximally is a proximal hard stop 821. These hard stops 819, 821 exist where the teeth 818 of the firing rack 816 end, thereby providing a mechanical backup to stop the firing rack 816 from either over firing (i.e., the proximal hard stop 821 prevents the firing rack 816 from overextending) or from over retracting (i.e., the distal hard stop 819 prevents the firing rack 816 from over retracting).

Figure 54A:
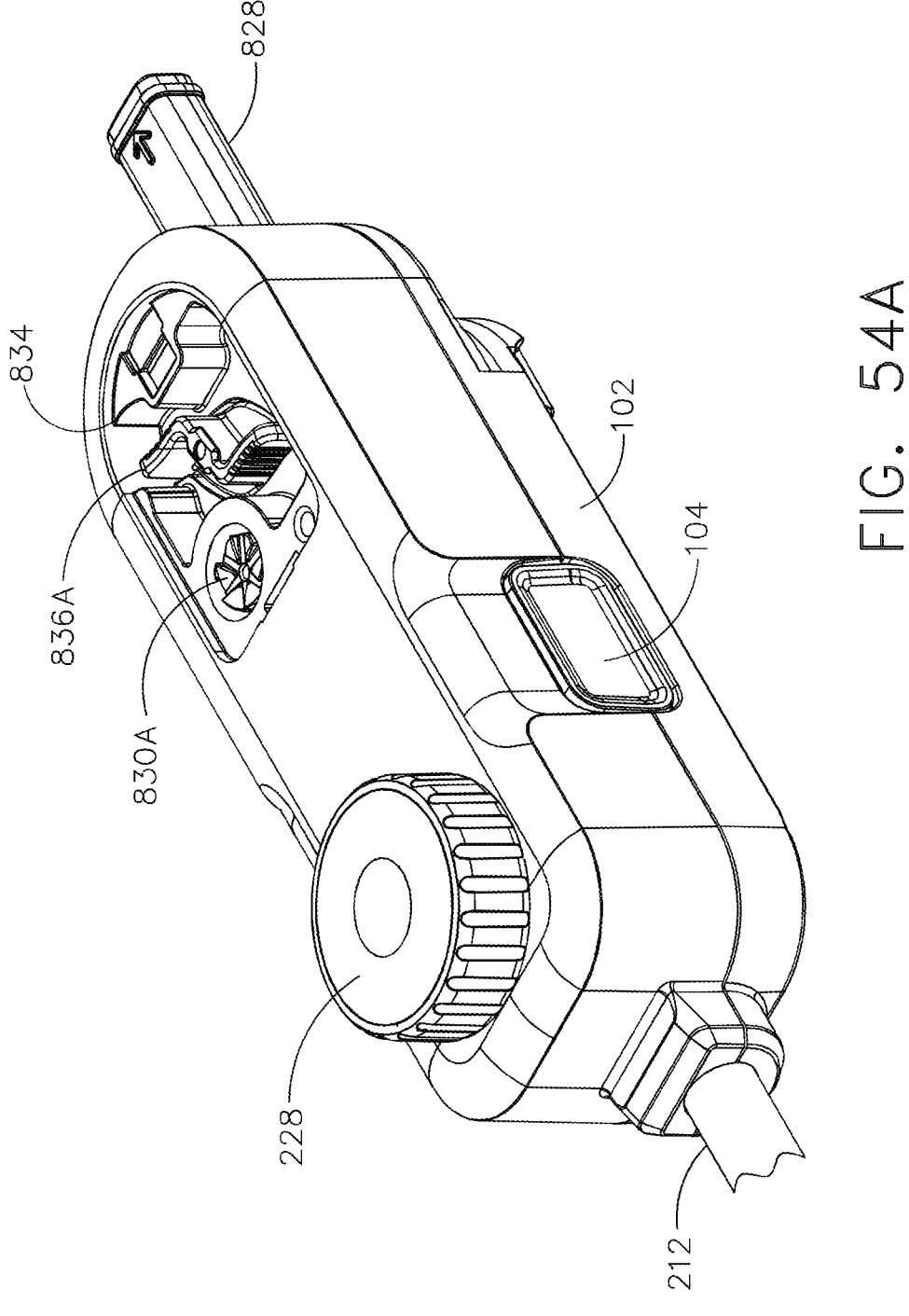
FIGS. 54A-54C show a compartment for a knife return mechanism, according to aspects of the present disclosure.
Figure 54B:
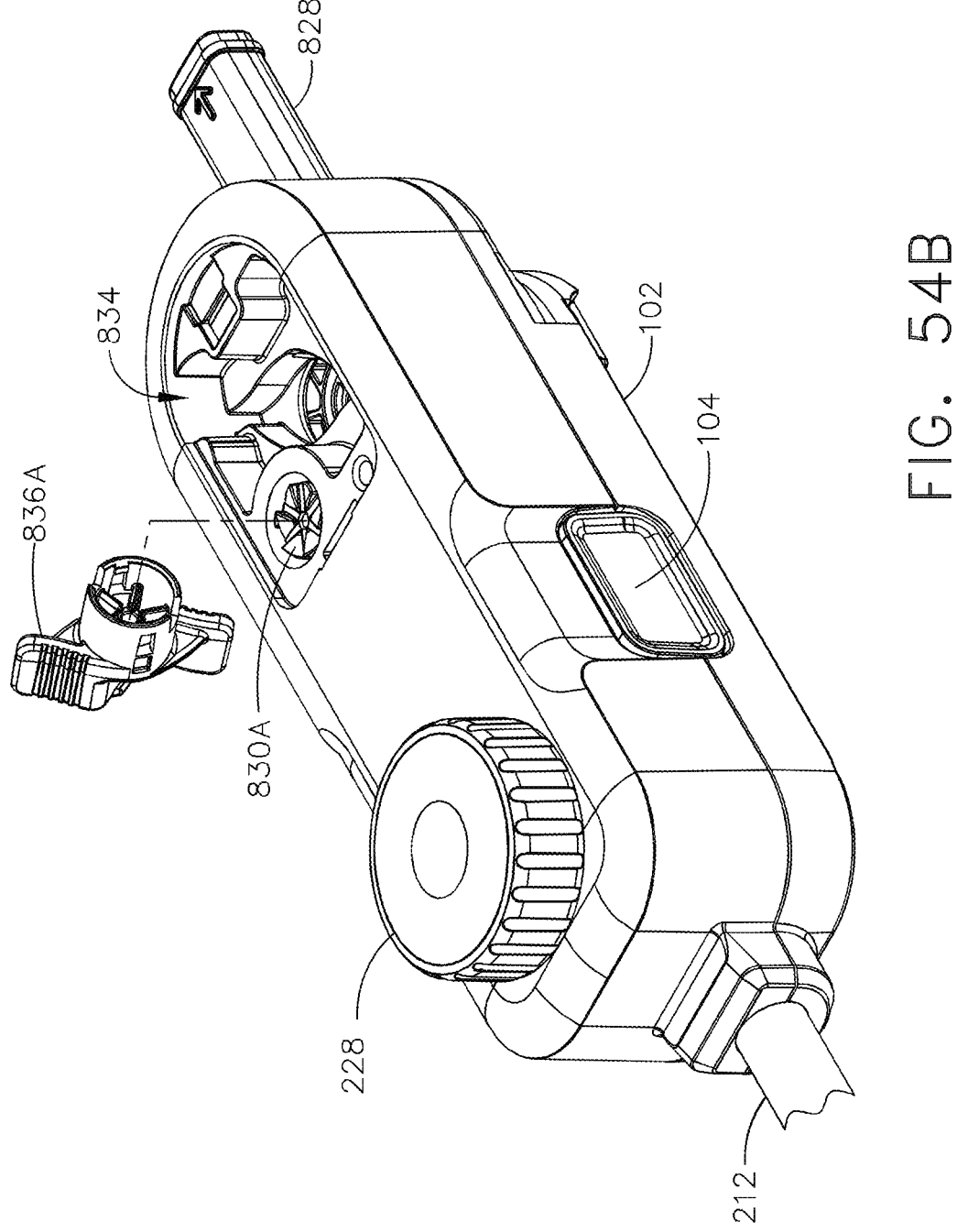
Figure 54C:
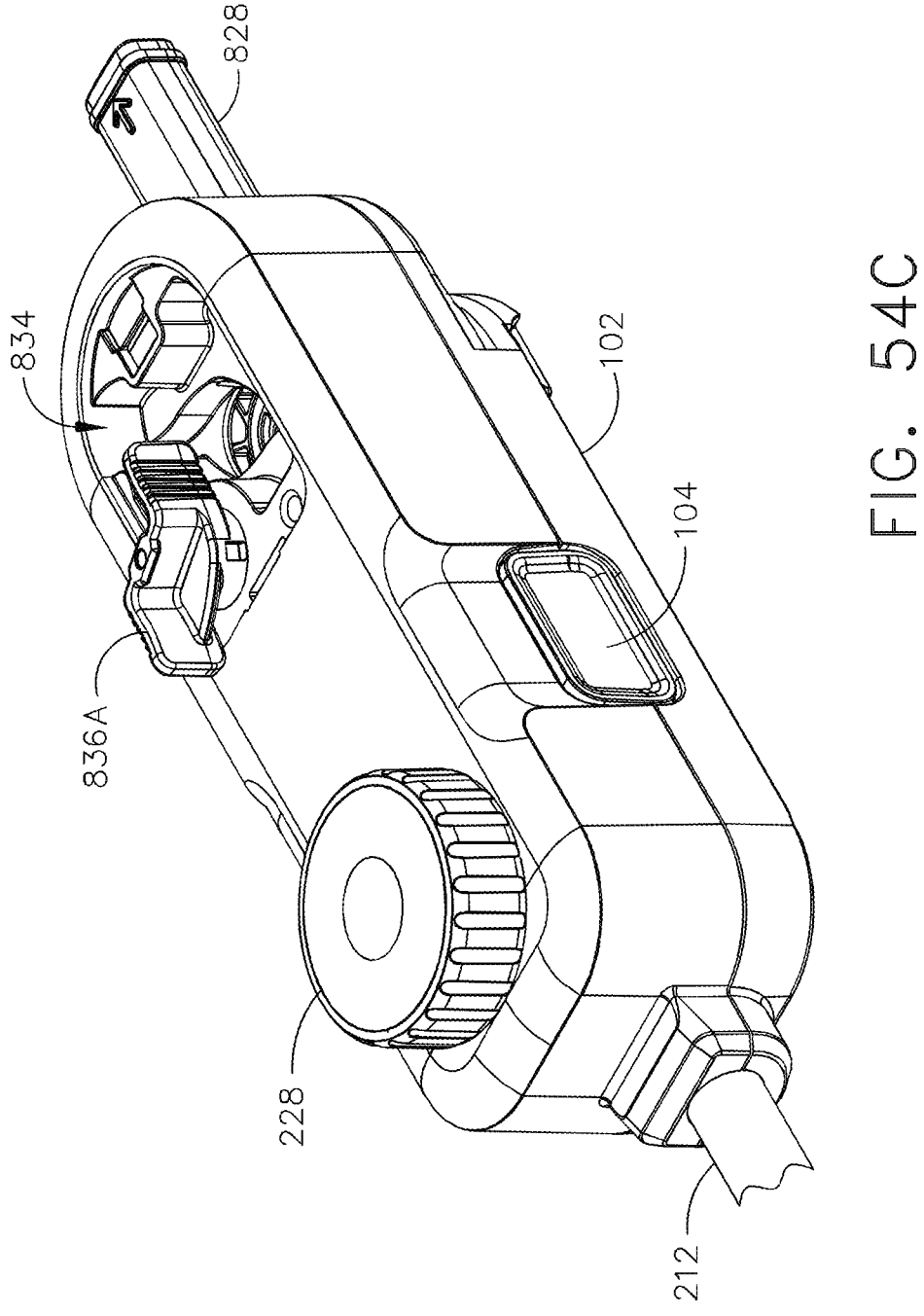

In some examples, the transection subsystem 800 can include a key receiver 830A that is rotationally coupled to the gearing of the transection subsystem 800 to manually retract the firing rack 816 and thus knife 166. The key receiver 830A can be rotationally coupled to the transection ramp gear 808 or the speed gear 812, whereas rotationally coupling the key receiver 830A to the transection ramp gear 808 provides a higher degree of gearing ratio such that rotation of the key receiver 830A moves the firing rack 816 proximally more quickly. This mechanical, manual retract can help in the scenario where the distal knife 166 has become stuck in tissue, and the robot is unable to turn the transection input puck 802 sufficiently to retract the knife 166. In some examples, as illustrated in FIG. 50, the outer housing 102 of the surgical instrument 100 can have a compartment 834 that is closed by the cover 832 that provides access to the key receiver 830A. The compartment 834 can also include a manual knife return key 836 that can be removed from the compartment 834, attached to the key receiver 830A, and rotated to translate the firing rack 816 proximally. The top of the key receiver 830A can have a unidirectional pattern that matches a unidirectional pattern on the manual knife return key 836 so that the firing rack 816 can only be retracted using this manual override, and not advanced. For example, the key receiver 830A can include ramps that allow unidirectional application of torque from the manual knife return key 836. In some examples, the firing rack 816 can extend proximally from the outer housing 102 and can be covered by a firing rack closure 828. The compartment 834, cover 832, manual knife return key 836, and firing rack closure 828 are shown in FIGS. 54A-54C.

Figure 54D:
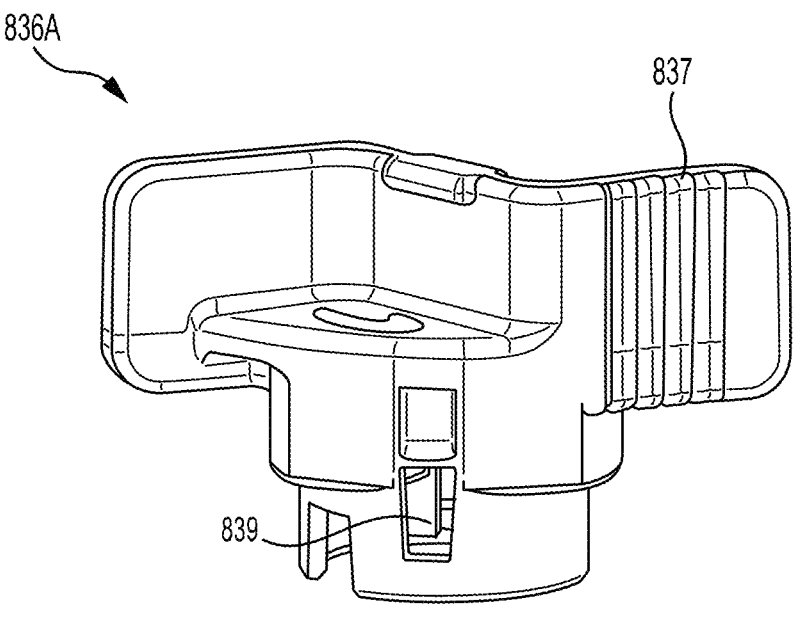
FIG. 54D is a perspective view of a manual knife return key, according to aspects of the present disclosure.
Figure 54E:
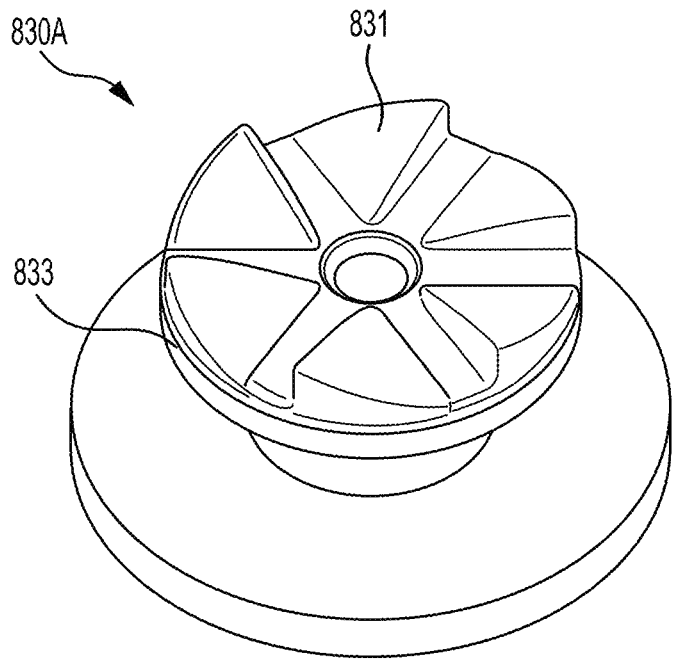
FIG. 54E is a perspective view of a key receiver, according to aspects of the present disclosure.

As shown in FIG. 54D, the manual knife return key 836A can include one or more locking tabs 839 configured to attach the manual knife return key 836A to the key receiver 830A. For example, as shown in FIG. 54E, the key receiver 830A can include a ledge 833 about which the locking tab 839 can extend to prevent the manual knife return key 836 from detaching from the key receiver 830A when attached. The locking tabs 839 can be positioned such that the manual knife return key 836A can move upwardly away from the key receiver 830A if the manual knife return key 836A is turned in the wrong direction but still be prevented from detaching from the key receiver 830A.

Figure 55A:
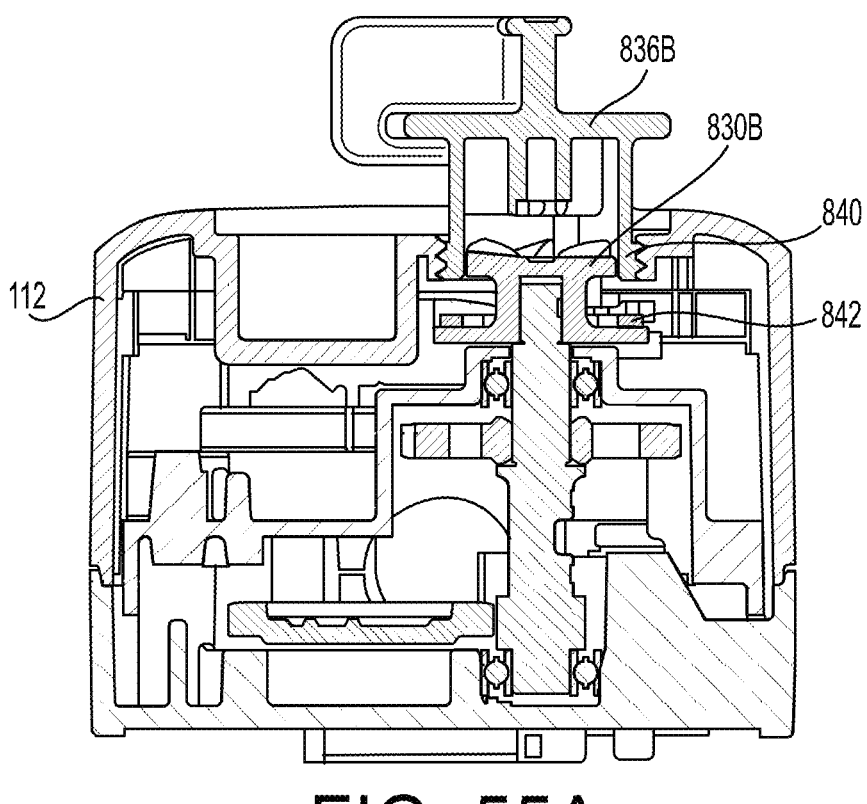
FIGS. 55A and 55B are section views of an alternative manual knife return system, according to aspects of the present disclosure.
Figure 55B:
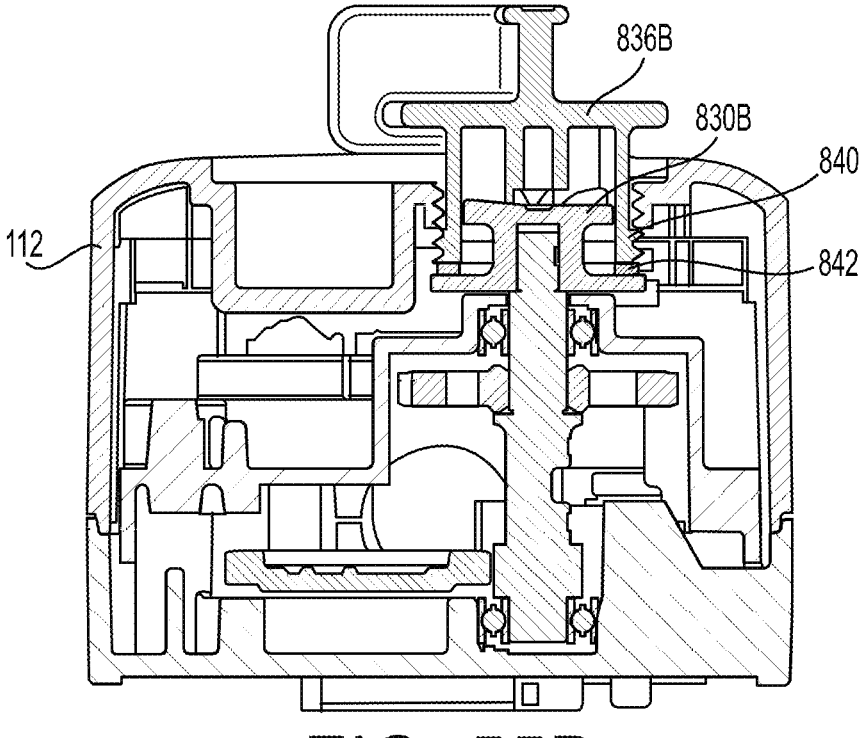

Several different examples of manual knife return configurations will now be described in relation FIGS. 55A-55Q. FIGS. 55A and 55B are cross-sectional views of alternate manual knife return key 836B and a key receiver 830B. The manual knife return key 836B in this example comprises exterior threads 840 that align with threads of the second portion 112 of the housing 102. The manual knife return key 836B can be threaded into the second portion 112 of the housing 102 and aligned with the key receiver 830B to manually retract the knife 166. The example shown in FIGS. 55A and 55B can include a gasket 842 that can bias the manual knife return key 836B outwardly such that the threads 840 of the manual knife return key 836B will engage the second portion 112 of the housing 102 to cause the manual knife return key 836B to remove from the housing 102 if the manual knife return key 836B is turned in the wrong direction. As will be appreciated, the threads 840 can help to retain the manual knife return key 836B in the housing 102 so that it won't be dropped or otherwise dislodged.

Figure 55C:
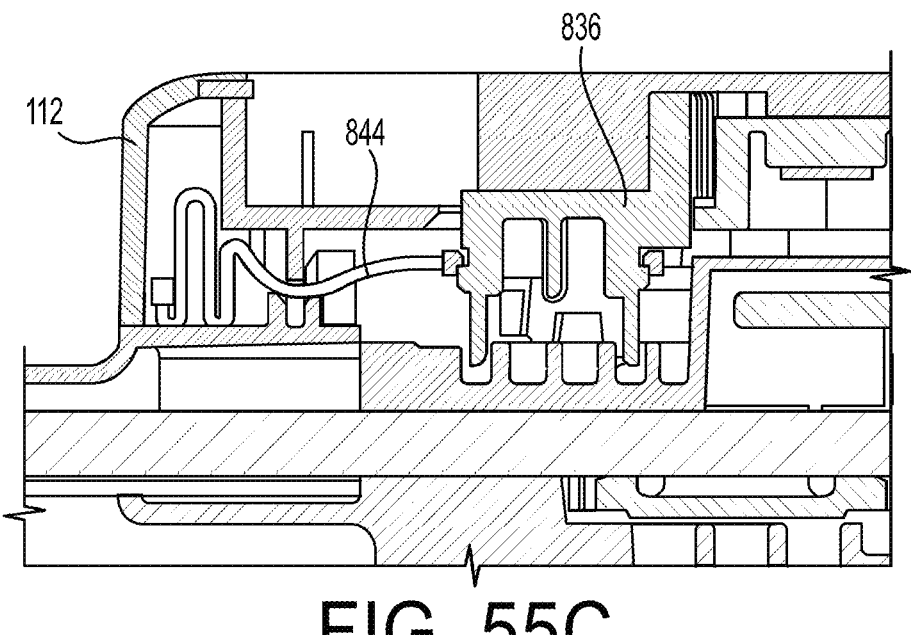
FIGS. 55C-55E are section and detail views showing a tether of the manual knife return system, according to aspects of the present disclosure.
Figure 55D:
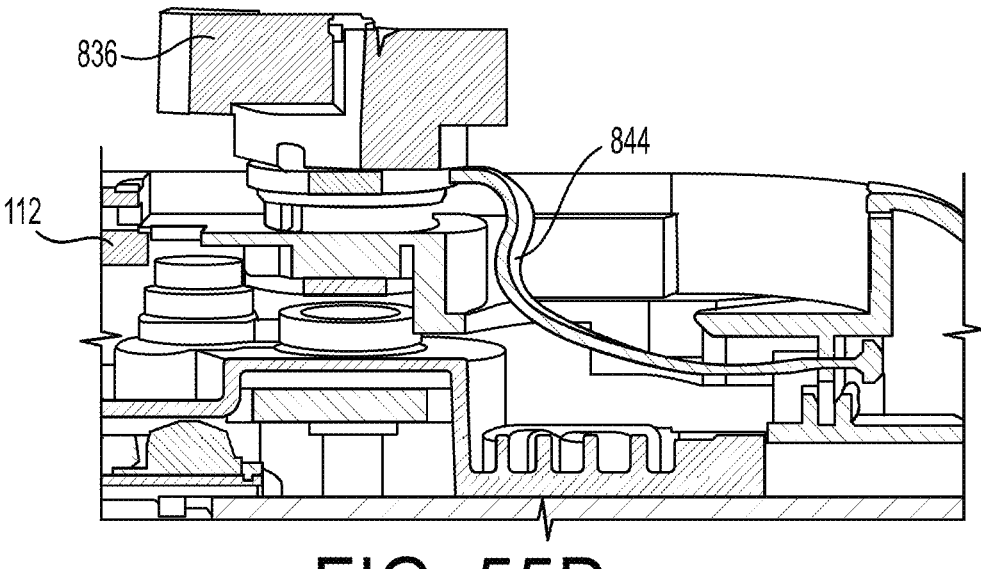
Figure 55E:
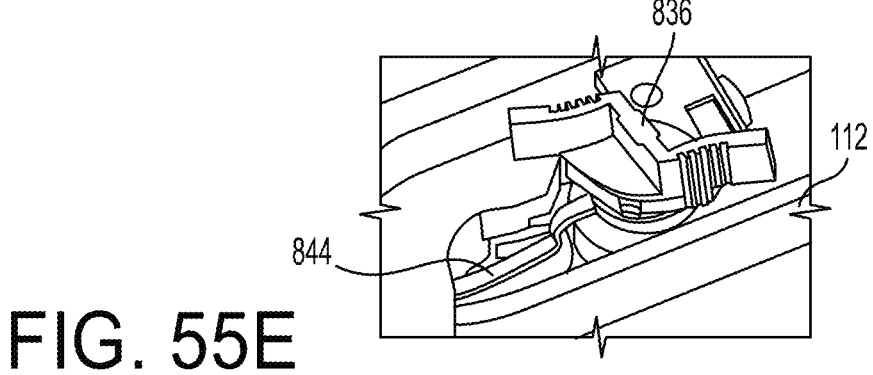

FIGS. 55C, 55D, and 55E illustrate a tether 844 that can be used with a manual knife return key 836 to help secure the manual knife return key 836 to the surgical instrument 100. The tether 844 can be attached around the manual knife return key 836 but allow for the manual knife return key 836 to turn freely. The tether 844 can be attached at the opposite end to the second portion 112 of the housing 102. In this way, the manual knife return key 836 can be prevented from being dropped or dislodged. As will be appreciated, dropping the manual knife return key 836 can lead to the manual knife return key 836 becoming unsterile and requiring either a replacement manual knife return key 836 or cleaning of the manual knife return key 836.

Figures 55F, 55G:
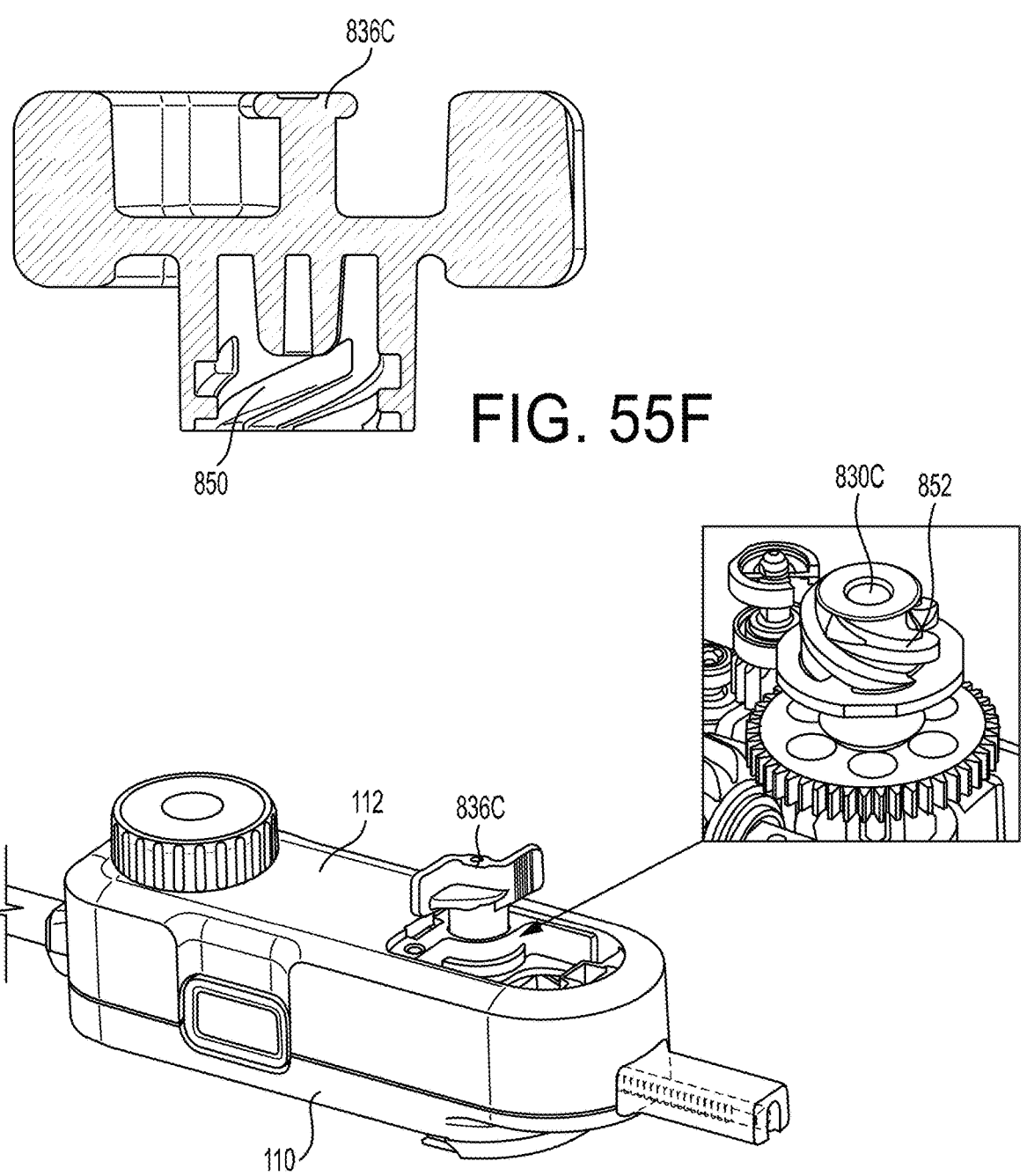
FIG. 55F is a section view of an alternative manual knife return key, according to aspects of the present disclosure.
FIG. 55G is a detail view of an alternative manual knife return key and key receiver, according to aspects of the present disclosure.

FIGS. 55F and 55G illustrate alternate examples of the manual knife return key 836C and the key receiver 830C. The manual knife return key 836C can include an internal cam 850 and the key receiver 830C can include a spline 852 that can correspond to the internal cam 850. In this example, the manual knife return key 836C can be threaded onto the key receiver 830C only in one direction to help prevent causing the knife 166 to extend distally (i.e., you only want the knife 166 to be retracted proximally when using the manual knife return key 836).

Figure 55J:
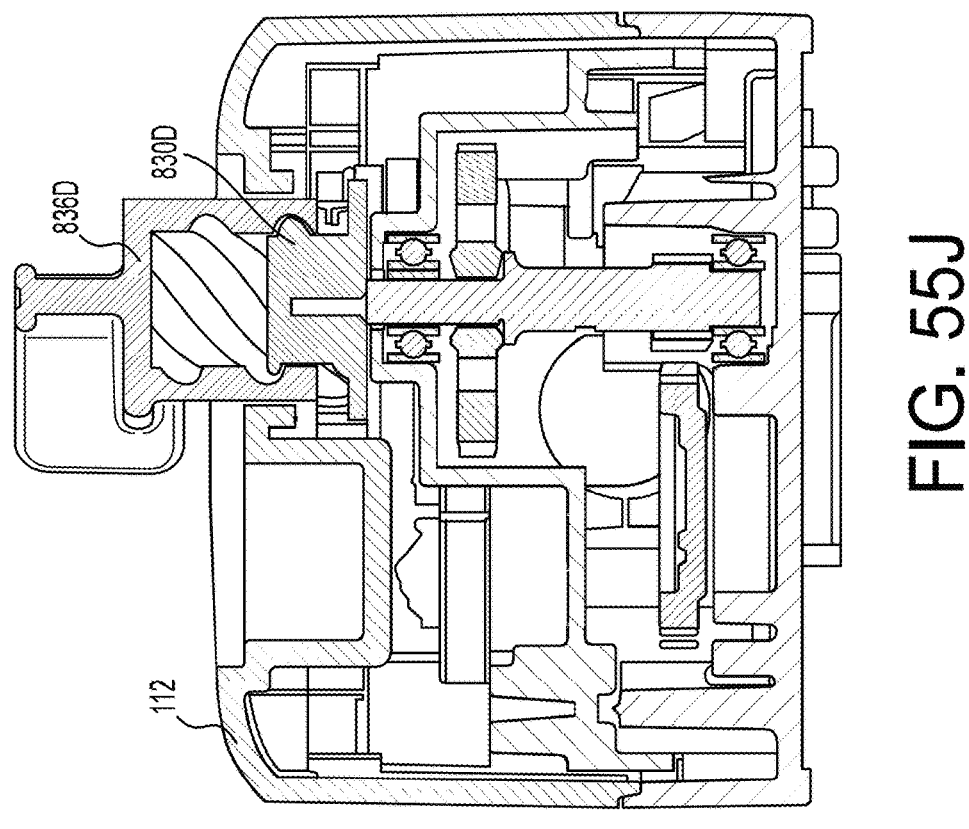
FIG. 55J is a section view of the other manual knife return system corresponding to FIGS. 55H and 55I, according to aspects of the present disclosure.
Figure 55H:
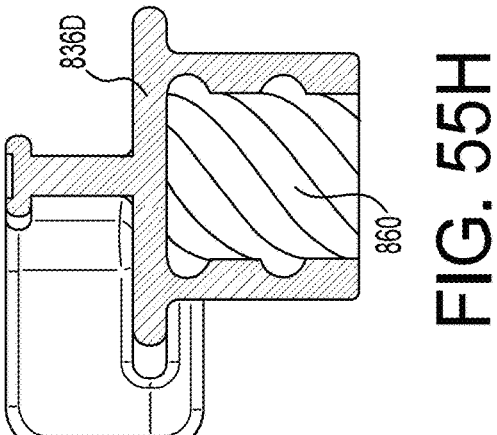
FIG. 55H is a section view of another example manual knife return key, according to aspects of the present disclosure.
Figure 55I:
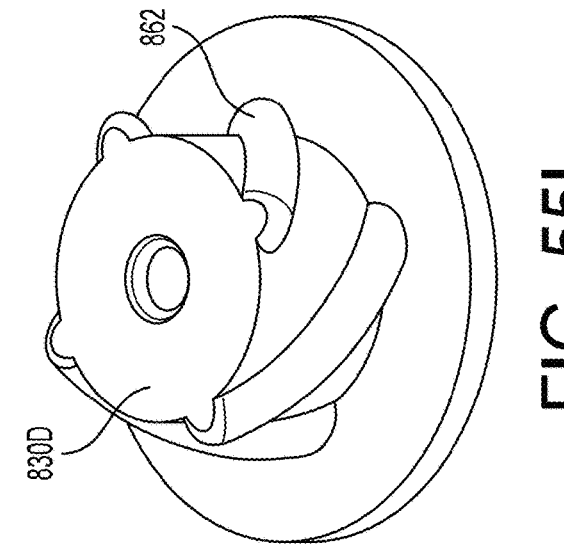
FIG. 55I is a perspective view of another example key receiver, according to aspects of the present disclosure.

FIGS. 55H-55J illustrate a similar manual knife return key 836D to the manual knife return key 836C and a similar key receiver 830D to the key receiver 830C. The manual knife return key 836D, however, can include a rounded internal cam 860 and the key receiver 830D can include a rounded spline 862. The rounded internal cam 860 can similarly engage the rounded spline 862 only in one direction to help ensure the manual knife return key 836D is rotated only in the direction of retracting the knife 166.

Figure 55K:
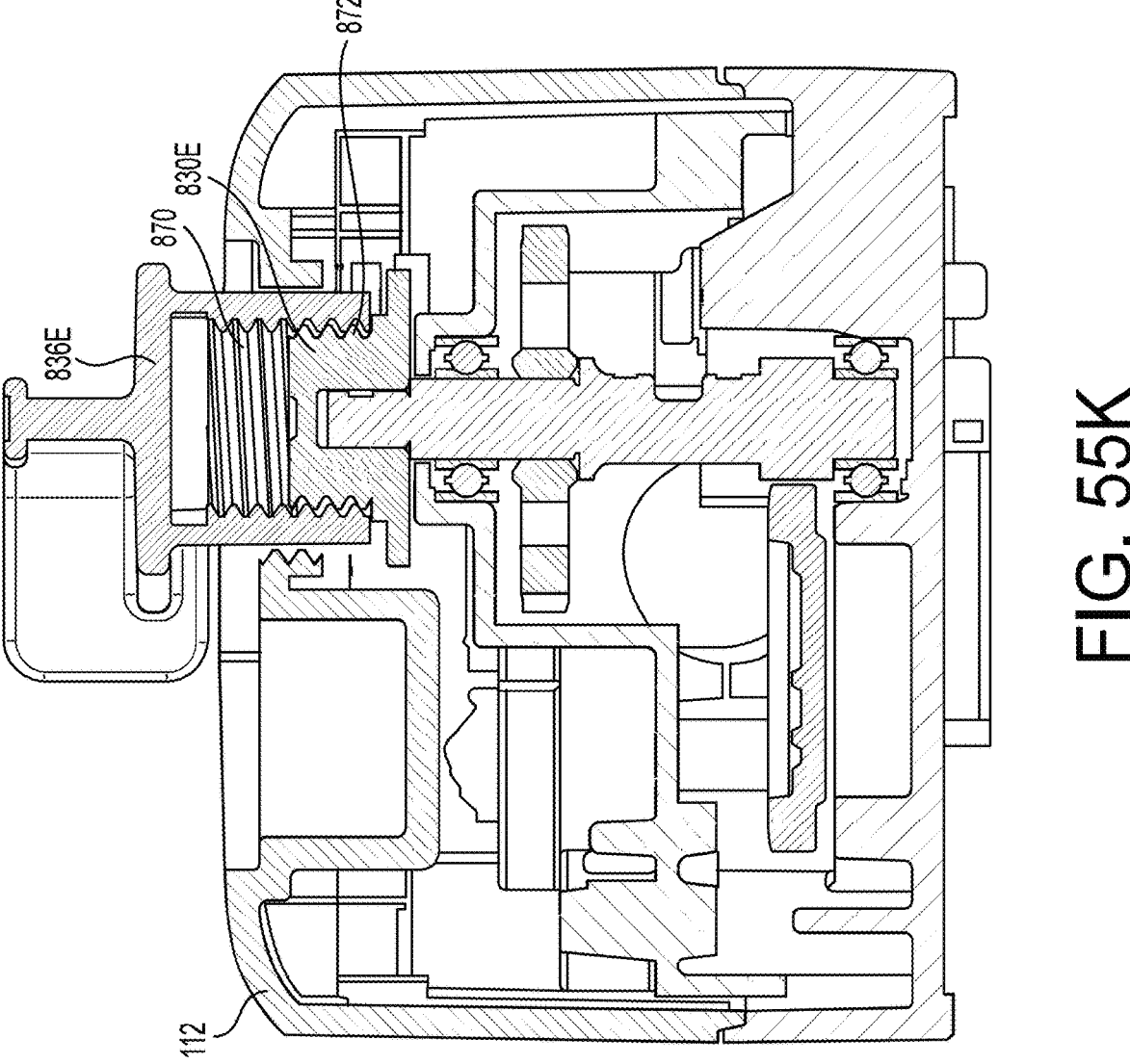
FIG. 55K is a section view of yet another example manual knife return system, according to aspects of the present disclosure.

FIG. 55K illustrates yet another manual knife return key 836E and key receiver 830E. The manual knife return key 836E can include internal threads 870 and the key receiver 830E can include external threads 872 that correspond to the internal threads 870. As before, the internal threads 870 are threaded in the direction of causing the knife 166 to retract. Thus, if a user were to turn the manual knife return key 836E in the wrong direction (i.e., cause the knife 166 to move distally), the internal threads 870 and the external threads 872 will cause the manual knife return key 836E to disengage from the key receiver 830E.

Figures 55L, 55M:
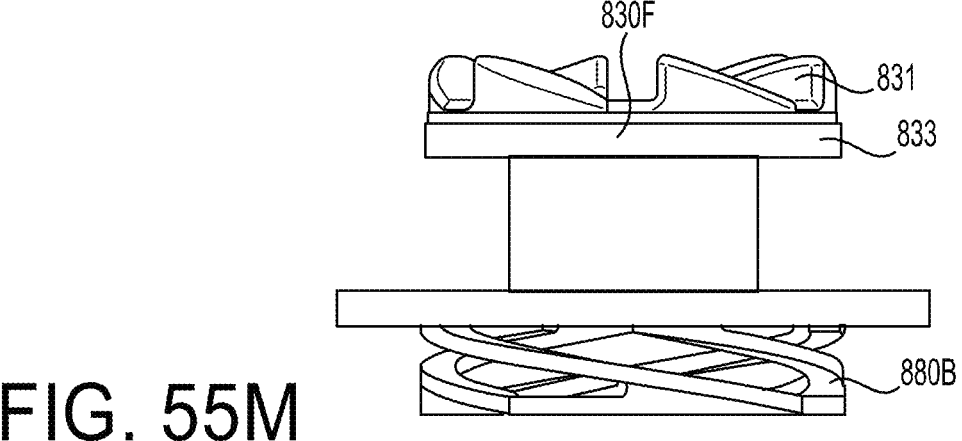
FIG. 55L is a section view of still another example manual knife return system, according to aspects of the present disclosure.
FIG. 55M is a side view of another example key receiver, according to aspects of the present disclosure.

FIG. 55L illustrates the manual knife return key 836B with the key receiver 830, but also includes a spring 880A that can permit the key receiver 830B to disengage from the manual knife return key 836B when the manual knife return key 836 is turned in the wrong direction. In this way, the key receiver 830B must be turned by the manual knife return key 836B in the correct direction to cause the knife 166 to retract. As shown in FIG. 55L, the manual knife return key 836B can be configured to contact the second portion 112 of the housing 102 to prevent a user from inserting the manual knife return key 836B into the key receiver 830B with sufficient force to overcome the ramps to cause the knife 166 to move distally. In other words, by including a spring 880A, a user can only turn the key receiver 830B in the correct direction (to cause the knife 166 to retract).

FIG. 55M illustrates another example of a key receiver 830F. The key receiver 830F can be similar to the key receiver 830B and spring 880A combination shown in FIG. 55L except the key receiver 830F includes an integrated spring 880B. The integrated spring 880B can perform the same function as the spring 880A described in relation to FIG. 55L. That is the integrated spring 880B permits the key receiver 830F to disengage from the manual knife return key 836B when turned in the wrong direction.

Figure 55N:
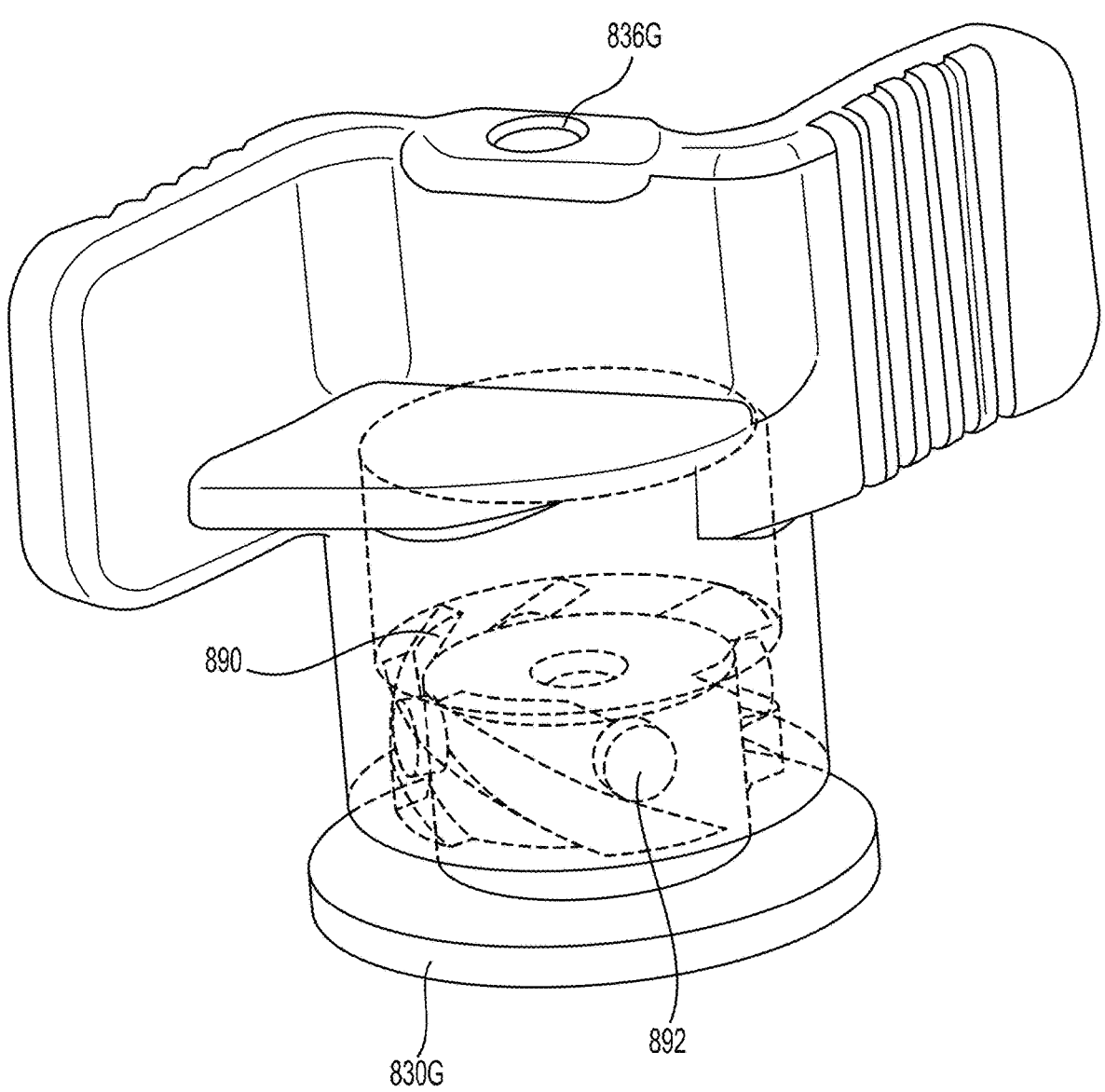
FIG. 55N is a transparent perspective view of another alternative manual knife return key and a key receiver, according to aspects of the present disclosure.

FIG. 55N illustrates another example manual knife return key 836G having an internal cam 890 design and the key receiver 830G can include a protrusion 892 that can extend into the internal cam 890. The manual knife return key 836G and key receiver 830G can be used similar to the manual knife return keys 836C and 836D previously described in that the manual knife return key 836G can only turn the key receiver 830G in one direction (i.e., the direction of retracting the knife 166).

Figure 55O:
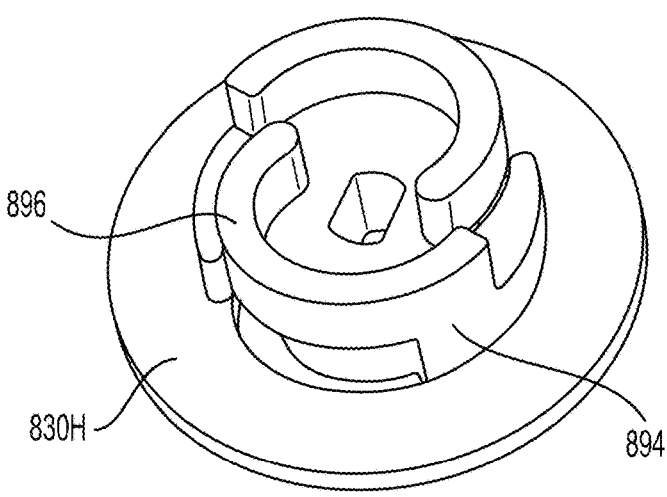
FIG. 55O is a perspective view of still another example key receiver, according to aspects of the present disclosure.
Figure 55P:
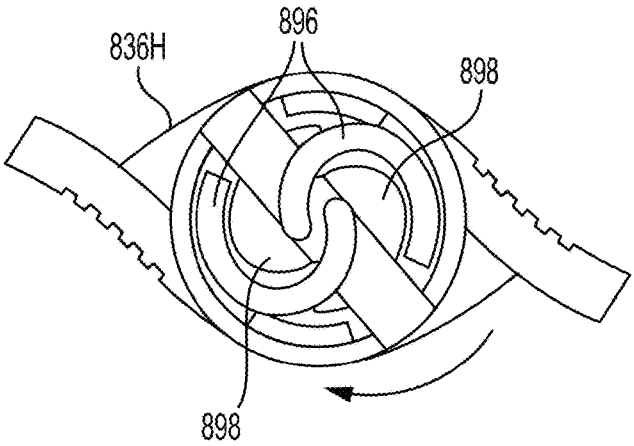
FIGS. 55P and 55Q illustrate interaction between a manual knife return key and the other example key receiver shown in FIG. 55O, according to aspects of the present disclosure.
Figure 55Q:
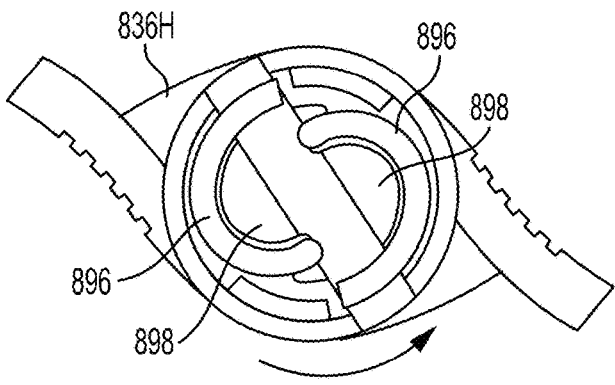

FIGS. 55O, 55P, and 55Q illustrate yet another example of a key receiver 830H and a manual knife return key 836H. The key receive 830H in this example can include supported walls 894 and cantilevered walls 896. The cantilevered walls 896 can be configured to bend out of the path of a key knobs 898 of the manual knife return key 836H when turned in the wrong direction (as shown in FIG. 55Q) but engage with the key knobs 898 when the manual knife return key 836H is turned in the correct direction (as shown in FIG. 55P). That is, the cantilevered walls 896 enable the key receiver 830H to only turn in the direction of the knife 166 retraction. If the user tried to turn the manual knife return key 836H in the wrong direction (i.e., causing the knife 166 to move distally), the cantilevered walls 896 will disengage from the manual knife return key 836H and the user cannot cause the knife 166 to move distally.

Referring again to FIGS. 37-40, the figures provide a view of the end effector 150 of the surgical instrument 100, i.e., the part of the end effector 150 distal to the joint 160. The end effector 150 includes an anvil 152 that is rotatably connected to a lower channel 156 via a hinge 164. The lower channel 156 can accept a staple cartridge 120 within a cartridge slot 162 therein. The staple cartridge 120 includes a plurality of staples 126 (not visible in FIG. 44 but inside of cartridge 120). A sled 122 can be driven distally through the cartridge 120 to drive the staples into the anvil 152. The sled 122 can be pushed distally via the knife 166 at the end of the bands 826 (see FIG. 46). The knife 166 can, therefore, can act both as a firing member to push the sled 122 distally and as a transection member to cut tissue. The knife 166 can be retained at a closed non-fired "home" position (see FIG. 45) by a leaf spring 168. The anvil 152 includes an anvil ramp 154 proximally. The closure subsystem 200 can close the anvil 152 by moving the closure ring 226 distally and over the anvil ramp 154, thereby hinging the anvil 152 closed. The anvil 152 can be biased in an open configuration (see FIG. 44) with a series of springs 172 (see FIG. 46) within the end effector 150.

Figure 47:
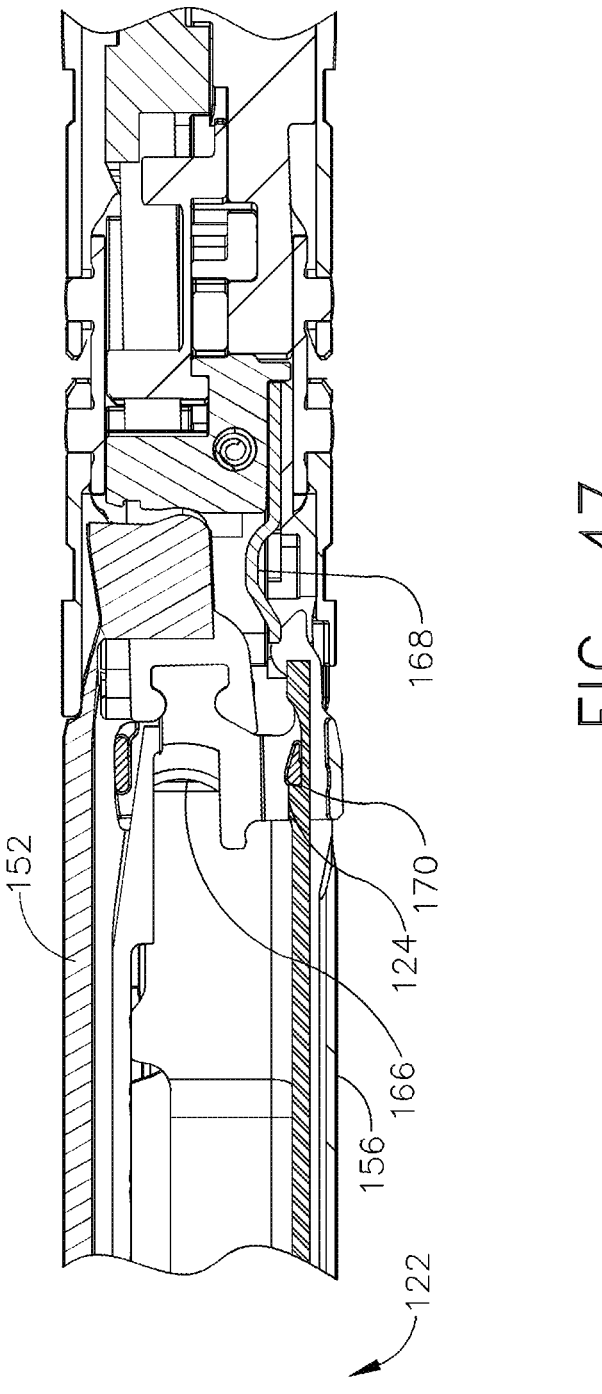
FIG. 47 is a cross-sectional view of an end effector portion of a surgical instrument, according to aspects of the present disclosure. The figure provides a detailed view of components of the end effector and cartridge.

In some examples, and as shown in the detail view in FIG. 47, the end effector 150 can have a safety mechanism in place to prevent attempts to fire a spent cartridge, or prevent firing the knife 166 when there is no cartridge 120 present within the cartridge slot 162. For example, the knife 166 can be biased toward the lower channel 156 (for example by the leaf spring 168), and the knife 166 requires a sled 122 to be present for the knife 166 to travel distally. If no sled 122 is present (indicating that the cartridge 120 is spent or there is no cartridge 120), the knife 166 will bias toward the lower channel 156, and then a lockout wing 170 on the knife 166 can contact a lockout wall 124 on the lower channel 156 to stop distal movement of the knife 166.

Fluid Management

Figures 56A, 56B:
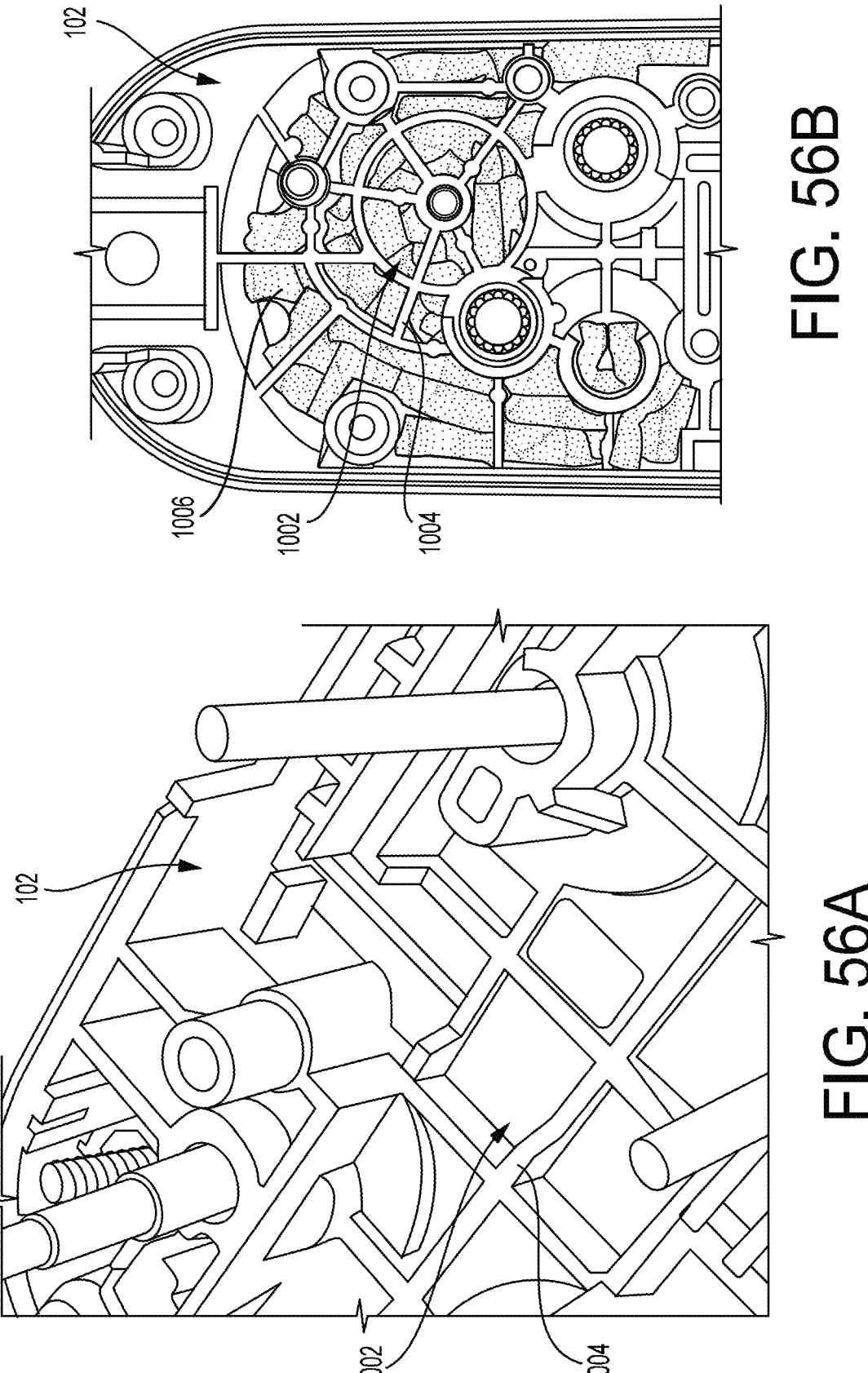

The surgical instrument 100 is intended to be subjected to bodily fluid and sterile saline swishes that travel on and through the shaft 604 and housing 102 of the instrument. For example, a primary source of fluid is from a swishing step that clears stray staples and tissue from the end effector 150. A scrub nurse can then hold the surgical instrument 100 to allow draining, but fluid flow should be controlled. The fluid's movement to areas sensitive to fluid, such as components inside the housing 102, can be accelerated by insufflation pressure and gravity. FIG. 56A-63B show example designs to slow fluid movement. FIG. 56A-63B show features to control fluid ingress into and egress from the housing 102 described herein, according to aspects of the present disclosure. For instance, a first goal is to prevent fluid from entering the housing 102 at all (i.e., prevent ingress; see FIGS. 61 and 62 for example solutions to ingress). If fluid does enter the housing 102, a secondary goal is to retain the fluid within the housing 102 (i.e., prevent egress; see FIGS. 56A-60B, and 63A-63B for example solutions to egress). Turning now to FIG. 56A, the example shows certain fluid management cavities 1002 surrounded by, or defined by, walls 1004. One way to prevent unintended fluid egress is to modify the housing 102 (one of or both of the first portion 110 or second portion 112) to have walls 1004 to minimize the overspill of liquid out of bottom of the housing 102. Those walls 1004, in addition to ribs that provide structure to the rest of the housing 102, can be used to create cavities 1002 of space to pool the liquid into predefined areas. The cavities 1002 can also accommodate a material capable of retaining any fluid entering the cavity 1002. FIG. 56B shows absorbents 1006 positioned in individual cavities 1002. The absorbent 1006 can be any type of material to hold the fluid. For example, the absorbent 1006 can be a hydrophilic fiber component that has a high wettability and does not expand greatly in size as it absorbs fluid—such materials can be suited to attract the fluid and hold it via surface tension within the fibrous volume. These materials can include polyethylene, polystyrene, polyvinylchloride, polytetrafluorethylene, polydimethylsiloxane, polyesters, and polyurethanes foams, meshes, fibers and the like.

Figures 57A, 57B, 57C, 57D, 57E:
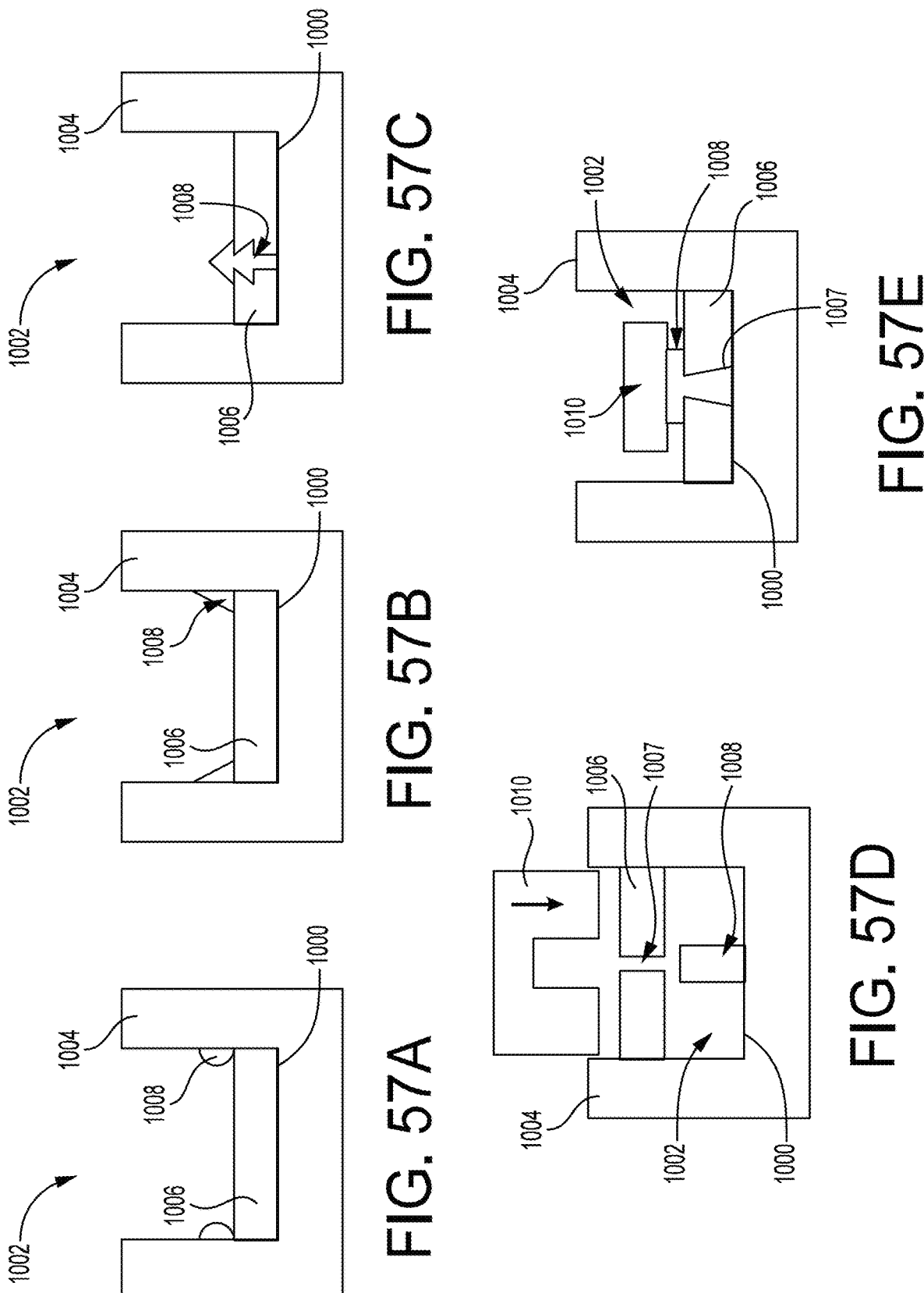
FIGS. 57A-57E show example designs for walls of the cavities described with respect to FIG. 56A, according to aspects of the present disclosure.

FIGS. 57A-57E show example designs for walls of the cavities 1002 described with respect to FIG. 56A, according to aspects of the present disclosure. In FIG. 57A, the walls 1004 that define each cavity 1002 include retention features 1008, and in the case of this example the retention features 1008 are rounded undercut features. The absorbent 1006 can be positioned in the cavity 1002 and be held in place to an interior surface 1000 of the housing 102 by the rounded retention features 1008 of the adjacent wall 1004. In FIG.

57B, the retention features 1008 are also undercut feature but in this example are one-way undercuts. When inserting the absorbent 1006 into the cavity 1002, the absorbent 1006 will slide down a ramp on one side of the retention features 1008 and be locked into place to an interior surface 1000 of the housing 102 by the flat underside of the undercut retention features 1008. In FIG. 57C, the retention features 1008 include a barb such that, once the absorbent 1006 is inserted into the cavity 1002, the barb will hold the absorbent 1006 in place to an interior surface 1000 of the housing 102. In FIG. 57D, the retention feature 1008 is a pin extending from the base of the cavity 1002. As can be seen an insertion tool 1010 can be used in this example to seat the absorbent 1006. The absorbent 1006 is pushed onto the pin, which is the retention feature 1008 in this example, allowing the pin to slide through an aperture 1007 in the absorbent 1006. Once seated, the insertion tool 1010 can be removed and the pin will hold the absorbent 1006 in place to an interior surface 1000 of the housing 102. In FIG. 57E, the retention feature 1008 is a rivet extending from the base of the cavity 1002. As can be seen, an insertion tool 1010 can be used in this example to actuate the rivet to hold the absorbent 1006 in place to an interior surface 1000 of the housing 102. As will be appreciated, any of the examples shown in FIGS. 57A-57E can be used in combination with any of the other examples.

Figures 58A, 58B:
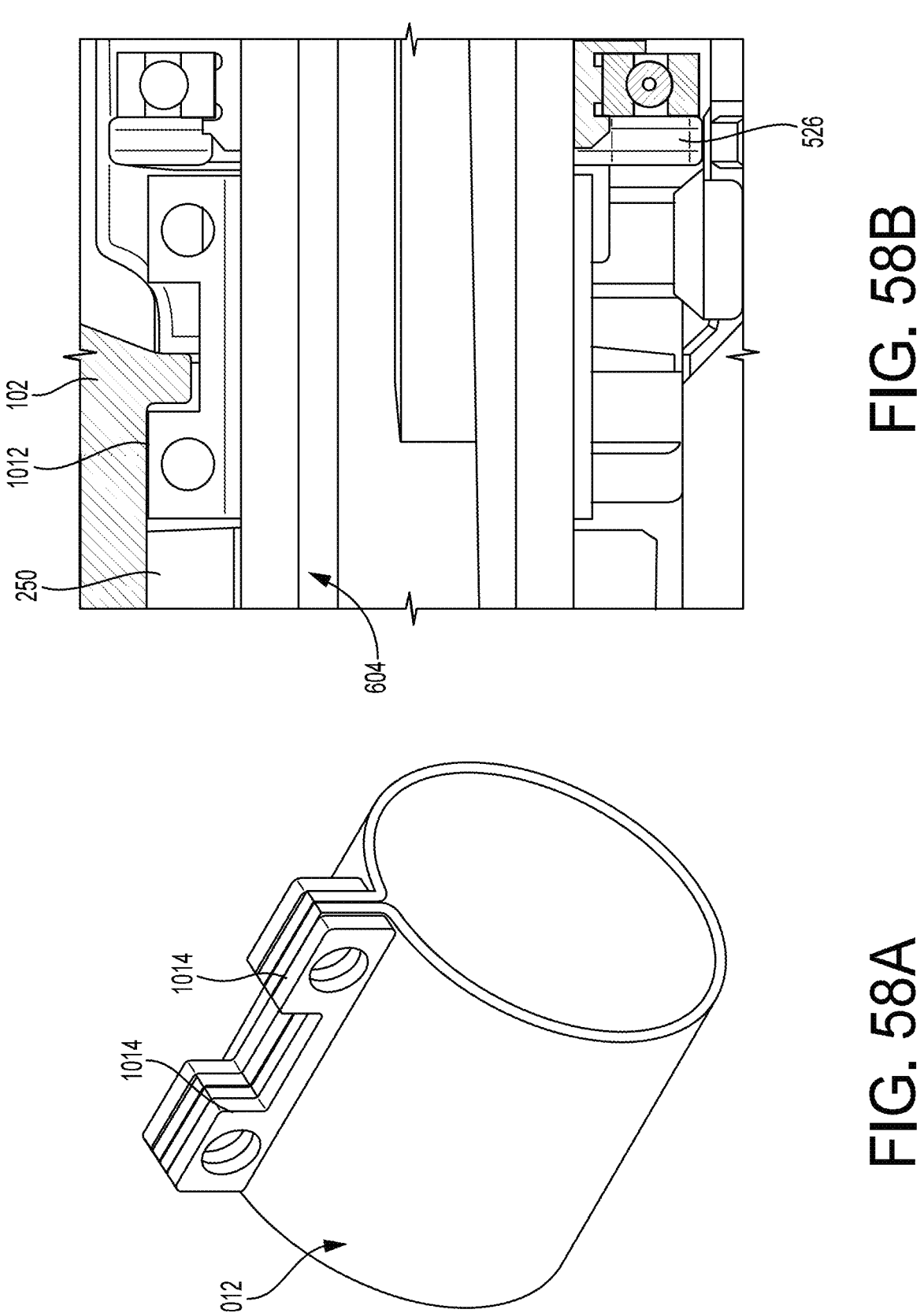
FIG. 58A shows an example fluid management sleeve, according to aspects of the present disclosure.
FIG. 58B shows a cross sectional view of the positioning of the sleeve, according to aspects of the present disclosure.

FIG. 58A shows an example fluid management sleeve 1012, according to aspects of the present disclosure. The sleeve 1012 can be positioned such that it is close to a known area for fluid ingress, which is where the nose 1034 of the housing 102 meets the closure tube 212 (see FIG. 3). The sleeve 1012 can be positioned on the shaft 604 between the closure yoke 250 and the articulation bushings (first articulation bushing 526 is shown in the cross section of FIG. 58B, but the sleeve 1012 could equally be applied to the examples shown with first articulation bushing 426 and second articulation bushing 428). FIG. 58B shows the positioning of the sleeve 1012. As will be appreciated, the respective articulation bushings described herein are designed to move proximally and distally to effect articulation, and as such a length of the sleeve 1012 can be such that it is shorter than a distance between the closure yoke 250 and the most-distal position of the respective articulation bushing(s). The sleeve 1012 can be affixed to the housing 102, for example by use of one or more sinching plates 1014 that can be positioned between grooves within the housing 102. The sleeve 1012 can be made of a hydrophilic fiber component that has a high wettability and does not expand greatly in size as it absorbs fluid—such materials can be suited to attract the fluid and hold it via surface tension within the fibrous volume. These materials can include polyethylene, polystyrene, polyvinylchloride, polytetrafluorethylene, polydimethylsiloxane, polyesters, and polyurethanes foams, meshes, fibers and the like.

Figures 59A, 59B:
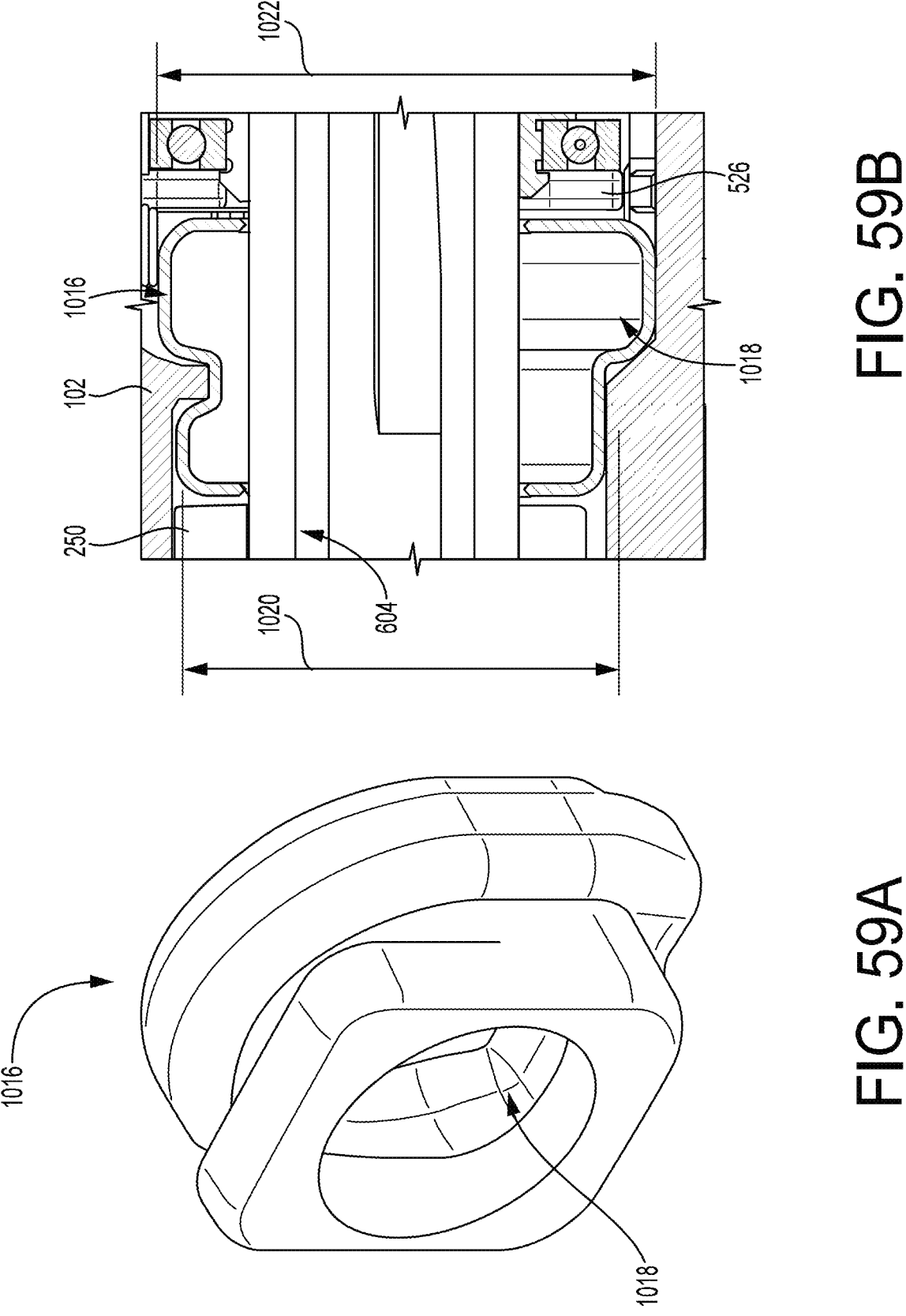
FIG. 59A shows an example fluid management trap collar.
FIG. 59B shows a cross sectional view of the positioning of the collar of FIG. 59A, according to aspects of the present disclosure.
Figure 59C:
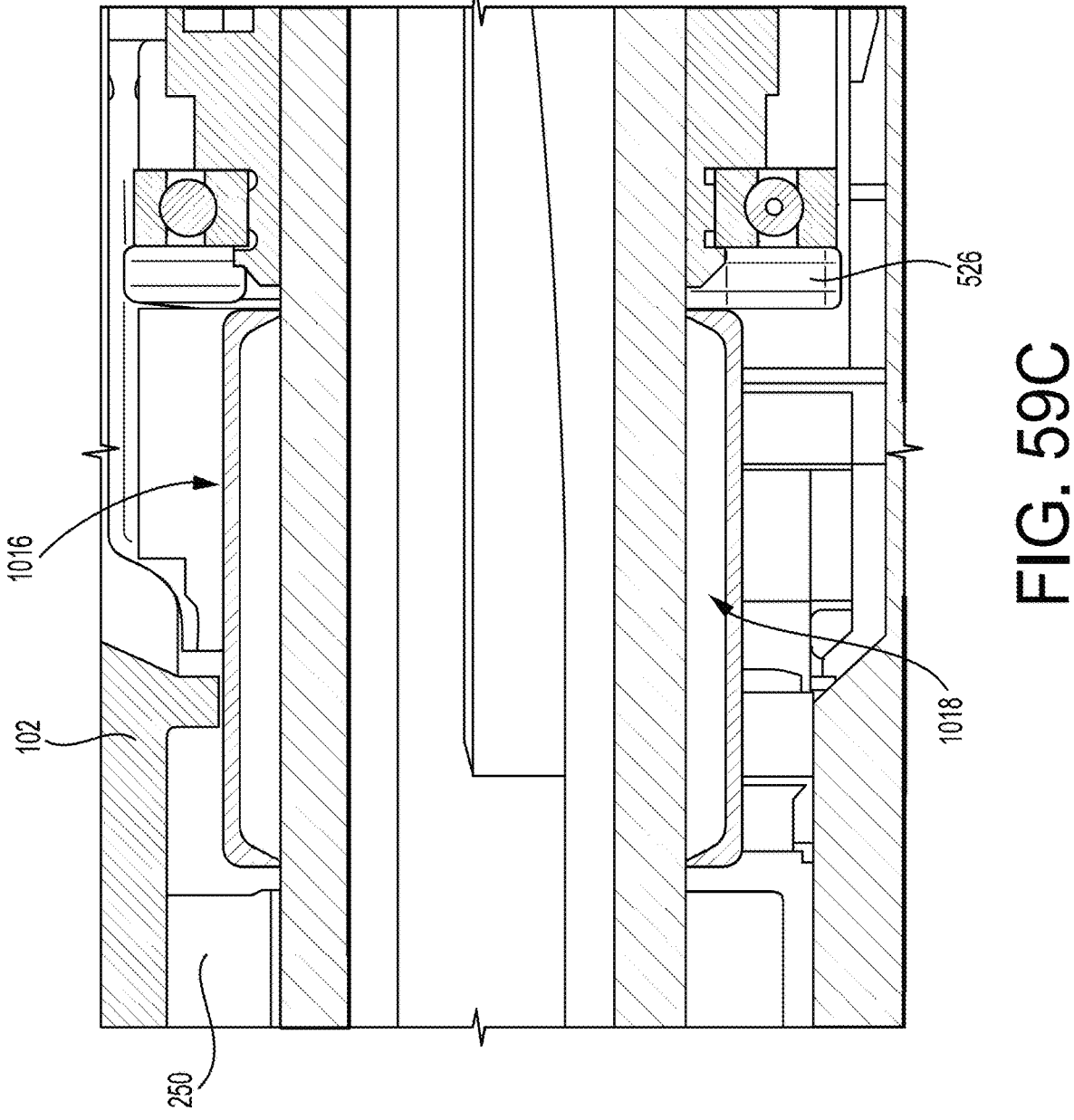
FIG. 59C is a similar example of a trap collar but without a separately defined trap.

FIG. 59A shows an example fluid management trap collar 1016, according to aspects of the present disclosure. The trap collar 1016 can be positioned such that it is close to a known area for fluid ingress, which is where the nose 1034 of the housing 102 meets the closure tube 212 (see FIG. 3). The trap collar 1016 can be positioned on the shaft 604 between the closure yoke 250 and the articulation bushings (first articulation bushing 526 is shown in the cross section of FIG. 59B, but the trap collar 1016 could equally be applied to the examples shown with first articulation bushing 426 and second articulation bushing 428). FIG. 59B shows the positioning of the trap collar 1016. As will be appreciated, the respective articulation bushings described herein are designed to move proximally and distally to effect articulation, and as such a length of the trap collar 1016 can be such that it is shorter than a distance between the closure yoke 250 and the most-distal position of the respective articulation bushing(s). The trap collar 1016 can be made of an elastomeric material that can hold a volume of fluid therein and/or redirect the fluid a different location within the housing 102. To capture the pooled liquid, the trap collar 1016 encircles the shaft 604. The stretch of the elastomeric material creates a seal against the shaft 604. In the example shown in FIGS. 59A and 59B, the trap collar has a defined trap 1018 wherein a width 1022 of the trap collar 1016 proximate the trap 1018 is larger than a width 1020 of the trap collar 1016 outside of the location of the trap 1018. Fluid can pool into the trap 1018. FIG. 59C is a similar trap collar 1016 but is cylindrical and does not have a separately defined trap 1018—the entire length of the trap collar 1016 can be considered a trap 1018.

Figures 60A, 60B:
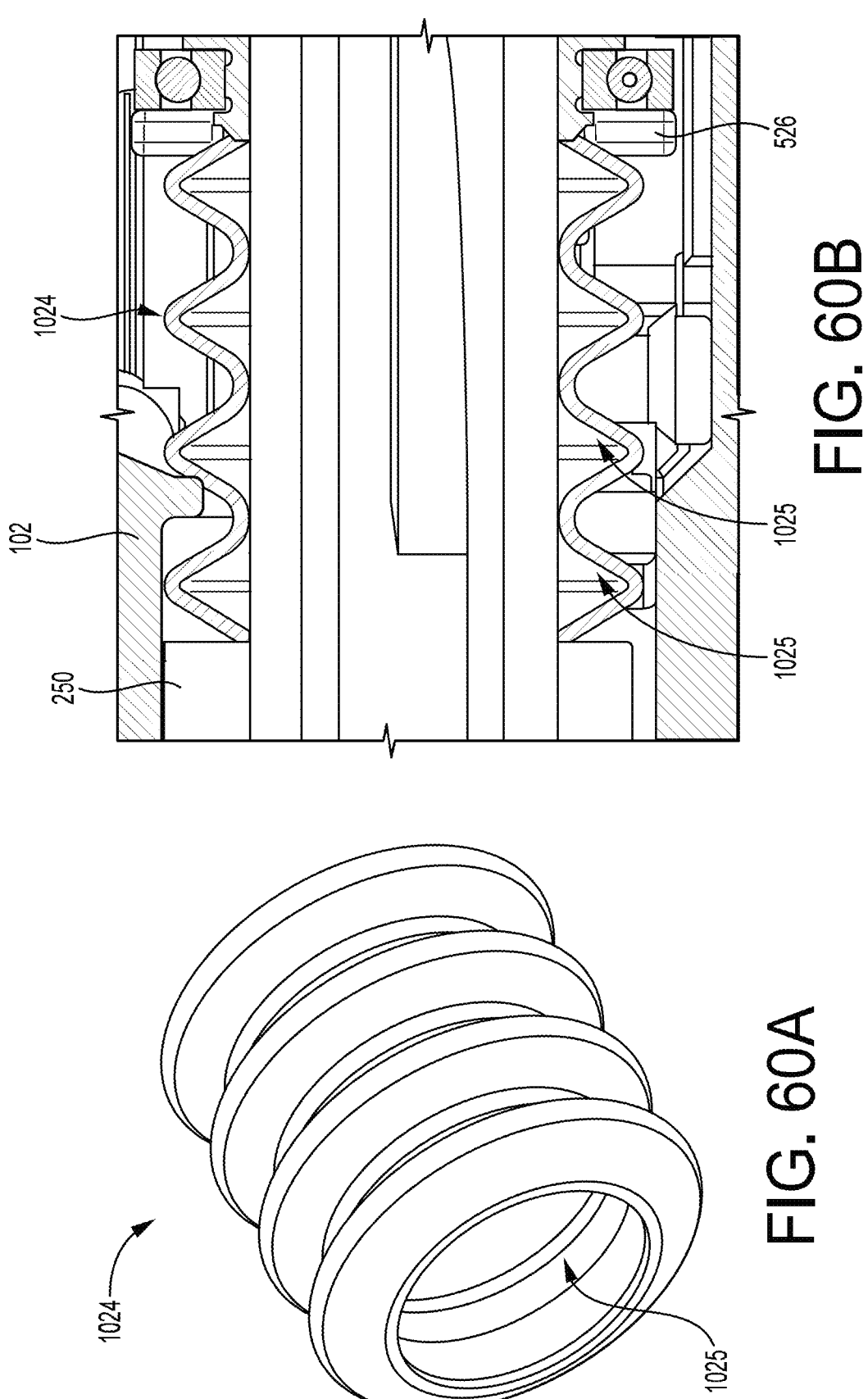
FIG. 60A shows an example fluid management flex collar, according to aspects of the present disclosure.
FIG. 60B shows a cross sectional view of the positioning of the collar, according to aspects of the present disclosure.

FIG. 60A shows an example fluid management flex collar 1024, according to aspects of the present disclosure. The flex collar 1024 can be positioned such that it is close to a known area for fluid ingress, which is where the nose 1034 of the housing 102 meets the closure tube 212 (see FIG. 3). The flex collar 1024 can be positioned on the shaft 604 between the closure yoke 250 and the articulation bushings (first articulation bushing 526 is shown in the cross section of FIG. 60B, but the flex collar 1024 could equally be applied to the examples shown with first articulation bushing 426 and second articulation bushing 428). FIG. 60B shows the positioning of the flex collar 1024. As will be appreciated, the respective articulation bushings described herein are designed to move proximally and distally to effect articulation. In this example, separate ends of the flex collar 1024 can be connected to the closure yoke 250 and respective articulation bushing(s) 426, 526, and the flex collar 1024 can expand and contract (like an accordion) with the axial movement of the articulation bushing(s) 426, 526. The flex collar 1024 can have an accordion-style shape, providing a plurality of traps 1025 to capture fluid.

Figure 61:
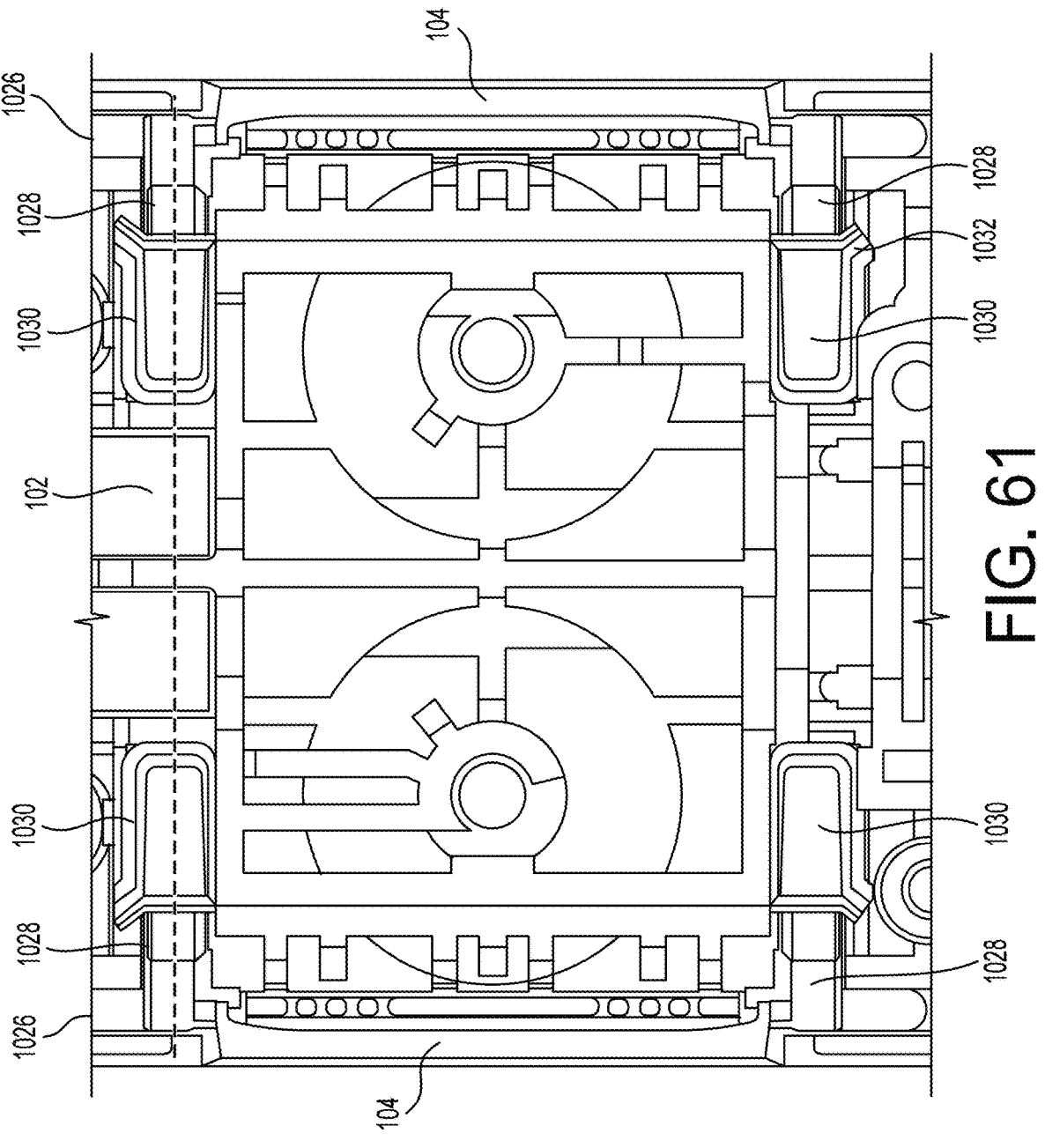
FIG. 61 shows example fluid diverters for a housing, according to aspects of the present disclosure.

FIG. 61 shows example fluid diverters 1030 for a housing 102, according to aspects of the present disclosure. Certain parts of the housing 102 can have openings that can allow fluid to flow into the housing 102. One such opening includes the one or more delatching bodies 1028 (also shown in FIG. 2) that aid in removing the surgical instrument 100 from a robotic arm (represented in FIG. 64) and/or from a sterile attachment that connects the surgical instrument 100 to the robotic arm. Exteriorly, as seen in FIG. 2, the delatching bodies 1028 can be positioned within delatch openings 1029 (see FIG. 2) that enable the housing 102 to be connected to an external robotic arm. These delatching bodies 1028 are connected to a release hinge 1026, and the release hinge 1026 is also connected to the release button 104. Actuation of the release button 104 can, therefore, move the delatching bodies 1028 such that they extend at least partially through the delatch openings 1029 to push the housing 102 from the robotic arm. This kinematic movement that cannot be blocked, so as to allow the attaching and detaching to the robotic arm. As such, fluid diverters 1030 can be positioned to cover at least a portion of the delatching bodies 1028 and the holes in the housing 102 that corresponds to the delatching bodies 1028. The fluid diverters 1030 can be elastomeric bodies that that can be trapped, glued, welded, etc. in place. When the delatching bodies 1028 needs to occupy the same space, the fluid diverters 1030 can flap or stretch to provide space for the delatching bodies 1028. Either position, though, allows the fluid to fill into an adjacent cavity (e.g., the cavities 1002 described with respect to FIG. 56A) and not egress from the housing 102. Each delatching bodies 1028 has channels 1032 that can divert fluid to adjacent cavities.

Figure 62:
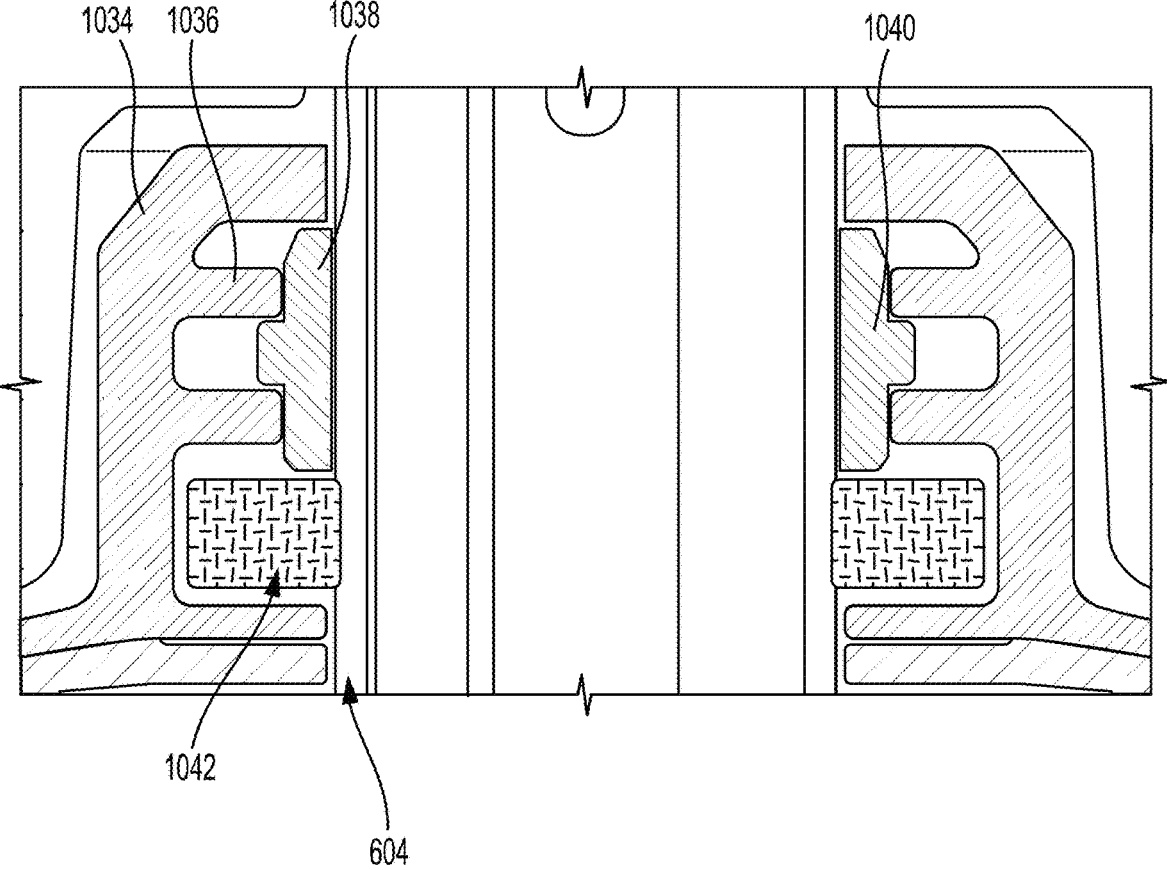
FIG. 62 shows a fluid management bushing for a housing, according to aspects of the present disclosure.

FIG. 62 shows a fluid management bushing 1038 for a housing, according to aspects of the present disclosure. The bushing 1038 can be positioned such that it is close to a known area for fluid ingress, which is where the nose 1034 of the housing 102 provides a tube opening 1035 for the closure tube 212 (see FIG. 3). The example bushing 1038 works like a traditional O-ring that take up the radial gap between the housing 102 and closure tube 212. The bushing 1038 can be positioned between adjacent flanges 1036 in the nose 1034 of the housing 102. The bushing 1038 may also not be a standard O-ring, but can also have bushing flanges 1040 that extend into areas between adjacent flanges 1036 in the nose 1034. Alternatively or additionally, an absorbent ring 1042 can be positioned to surround the closure tube 212 to prevent fluid movement through the nose 1034 of the housing 102. The absorbent ring 1042 can be similar to the absorbent 1006 described herein. An O-ring can also be positioned at any point between the closure tube 212 and the shaft 604.

Figures 63A, 63B:
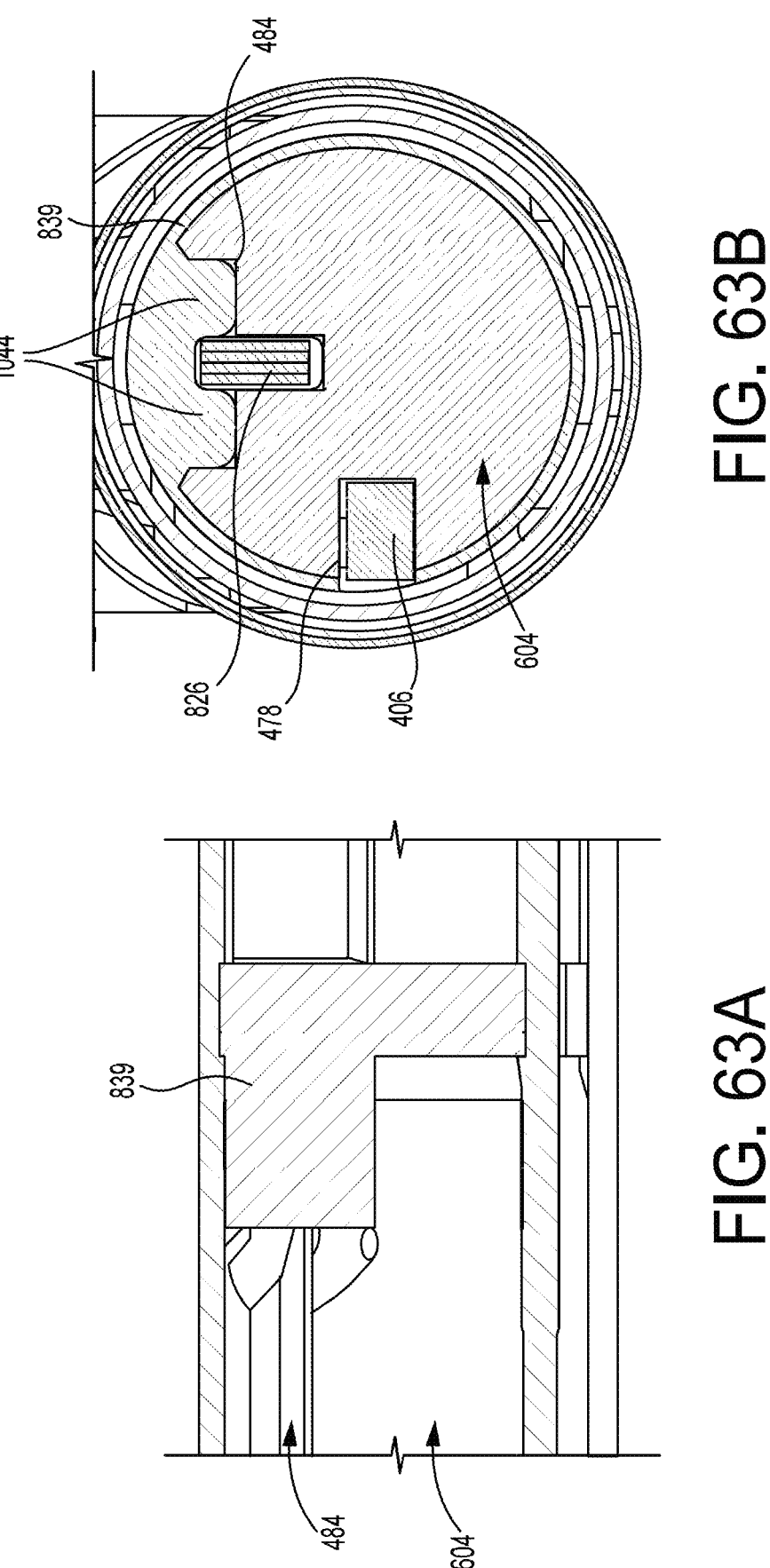
FIG. 63A shows an example fluid management seal extension for a knife insert retainer, according to aspects of the present disclosure.
FIG. 63B shows a cross sectional view of the positioning of the seal extension in FIG. 63A, according to aspects of the present disclosure.

FIG. 63A shows an example fluid management seal extension 1044 for a knife insert retainer 838 (see also FIG. 38). FIG. 63B shows a cross sectional view of the positioning of the seal extension 1044, according to aspects of the present disclosure. The challenge with a simple O-ring is that it does not seal where there are discontinuities in the circular diameter of the shaft 604, such as discontinuities for the band slot 484 for the bands 826, or for the rod groove 478 for the articulation rod 406. To accommodate this a seal, for example a seal extending from the knife insert retainer 838, can include one or more seal extensions 1044 extending therefrom. In FIG. 63B, there is a C-shape seal extensions 1044 extending within the band slot 484. The main job of the knife insert retainer 838 is to provide the knife with solid boundaries laterally, to minimize Euler buckling of the bands 826. By adding a feature like a "C-shaped" seal extension 1044 to that section, the seal extensions 1044 will plug the space that fluid can flow near the bands 826.

Control Devices and Methods

FIG. 64 is an illustration of an example control device 1110 for controlling the robotic arm 1100 and the surgical instrument 100. As shown, the control device 1110 can include a processor 1112; an input/output device; and a memory 1116 containing an operating system (OS) 1118, a storage device 1120, which can be any suitable repository of data, and a program 1122. The input/output device can be configured to receive and to output commands to control the robotic arm 1100 and the surgical instrument 100. The control device 1110 can include a user interface (U/I) 1124 device for receiving user input data (e.g., from a physician, technician, etc.), such as data representative of a click, a scroll, a tap, a press, movement of a control lever, or typing on an input device that can detect tactile inputs. The control device 1110 can include a display.

The control device 1110 can include a peripheral interface, which can include the hardware, firmware, and/or software that enables communication with various peripheral devices, such as media drives (e.g., magnetic disk, solid state, or optical disk drives), other processing devices, or any other input source used in connection with the instant techniques. The peripheral interface can include a serial port, a parallel port, a general-purpose input and output (GPIO) port, a game port, a universal serial bus (USB), a micro-USB port, a high definition multimedia (HDMI) port, a video port, an audio port, a Bluetooth™ port, a WiFi port, a near-field communication (NFC) port, another like communication interface, or any combination thereof to communicate with other devices via wired or wireless connections or networks, whether local or wide area, private or public, as known in the art. A power source can be configured to provide an appropriate alternating current (AC) or direct current (DC) to power components.

The processor 1112 can include one or more of an application specific integrated circuit (ASIC), programmable logic device, microprocessor, microcontroller, digital signal processor, co-processor or the like or combinations thereof capable of executing stored instructions and operating upon stored data. The memory 1116 can include one or more suitable types of memory (e.g., volatile or non-volatile memory, random access memory (RAM), read-only memory (ROM), programmable read-only memory (PROM), erasable programmable read-only memory (EPROM), electrically erasable programmable read-only memory (EEPROM), magnetic disks, optical disks, floppy disks, hard disks, removable cartridges, flash memory, a redundant array of independent disks (RAID), and the like) for storing files including the operating system 1118, application programs 1122 (including, for example, a web browser application, a widget or gadget engine, and or other applications, as necessary), executable instructions and data. One, some, or all of the processing techniques described herein can be implemented as a combination of executable instructions and data within the memory 1116.

The processor 1112 can be one or more known processing devices, such as a microprocessor from the Pentium™ family manufactured by Intel™, the Turion™ family manufactured by AMD™, or the Cortex™ family or SecurCore™ manufactured by ARM™ to provide just a few examples. The processor 1112 can constitute a single-core or multiple-core processor that executes parallel processes simultaneously. For example, the processor 1112 can be a single-core processor that is configured with virtual processing technologies. One skilled in the art will understand that other types of processor arrangements could be implemented that provide for the capabilities disclosed herein.

The control device 1110 can include one or more storage devices 1120 configured to store information used by the processor 1112 (or other components) to perform at least some of the functions disclosed herein. As an example, the control device 1110 can include memory 1116 that includes instructions to enable the processor 1112 to execute one or more applications, network communication processes, and any other type of application or software known to be available on computer systems. Alternatively, the instructions, application programs, or other software can be stored in an external storage and/or can be available from a remote memory over a network. The one or more storage devices can be a volatile or non-volatile, magnetic, semiconductor, tape, optical, removable, non-removable, or other type of storage device or tangible computer-readable medium.

The control device 1110 can include memory 1116 that includes instructions that, when executed by the processor 1112, perform one or more processes consistent with the functionalities disclosed herein. Methods, systems, and articles of manufacture consistent with disclosed embodiments are not limited to separate programs or computers configured to perform dedicated tasks. For example, the control device 1110 can include memory 1116 that can include one or more programs 1122 to perform one or more functions of the disclosed technology. For example, the control device 1110 can access one or more programs 1122, that, when executed, perform at least one function disclosed herein. One or more programs 1122 can be configured to receive input from a user (e.g., a physician, a technician, etc.) and cause the control device 1110 to output one or more control signals to the robotic arm 1100. The one or more programs 1122 can be configured to cause the user interface 1124 to display images indicative of a function or condition associated with the robotic arm 1100.

The memory 1116 of the control device 1110 can include one or more memory devices that store data and instructions used to perform one or more of the methods and features disclosed herein. The memory 1116 can include software components that, when executed by the processor 1112, perform one or more processes consistent with those disclosed herein. The control device 1110 can include any number of hardware and/or software applications that are executed to facilitate any of the operations. The one or more I/O interfaces 1114 can be utilized to receive or collect data and/or user instructions from a wide variety of input devices. Received data can be processed by one or more computer processors 1112 as desired in various implementations of the disclosed technology and/or stored in one or more memory devices.

While the control device 1110 has been described above for implementing the techniques described herein, those skilled in the art will appreciate that other functionally equivalent techniques can be employed. For example, as known in the art, some or all of the functionality implemented via executable instructions can also be implemented using firmware and/or hardware devices such as application specific integrated circuits (ASICs), programmable logic arrays, state machines, etc. Furthermore, the control device 1110 can include a greater or lesser number of components than those illustrated and/or described above.

Figure 65:
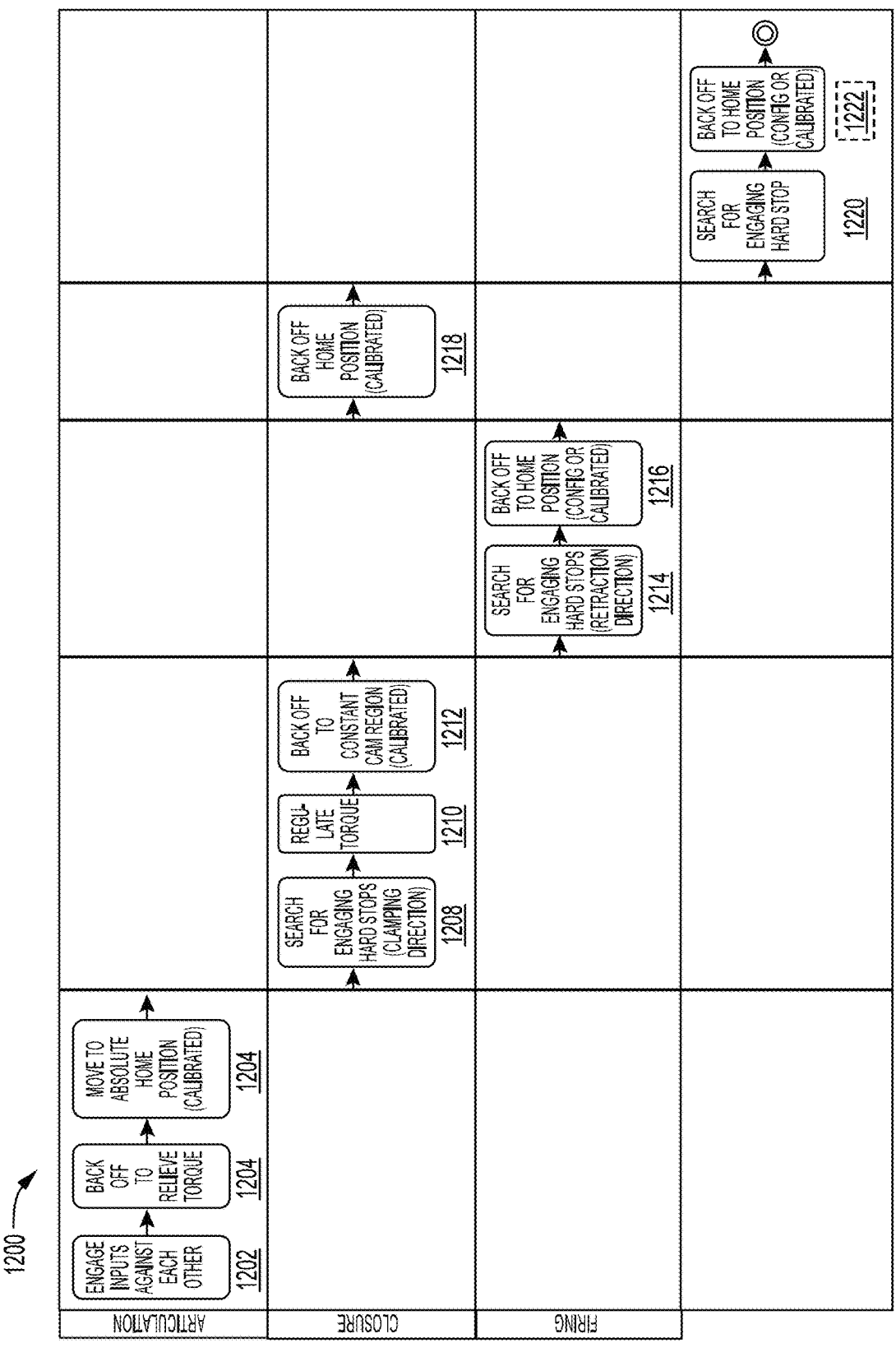
FIG. 65 is a flow chart depicting a method of engaging and homing the surgical instrument, according to aspects of the present disclosure.

Turning now to FIG. 65, a method 1200 of engaging and homing the surgical instrument 100 is shown and described. The term "engaging" refers to the act of aligning and mating the input pucks 202-802 of the surgical instrument 100 with corresponding pucks on a sterile adapter and the robotic arm 1100. Although not shown, the sterile adapter can be a component configured to interface with the surgical instrument 100 and the robotic arm 1100 and to keep the robotic arm 1100 sterile. The term "homing" refers to defining which motor positions correspond to zero joint positions and moving the joints to those positions (i.e., moving the joint to a home position).

As shown in FIG. 65, the method 1200 includes engaging and homing several of the subsystems shown and described herein. For example, the method 1200 can be utilized after first attaching the surgical instrument 100 to a robotic arm 1100. The method 1200 can include engaging and homing the articulation subsystem 400, the closure subsystem 200, the transection subsystem 800, and the roll subsystem 600. Although shown and described as being performed in a particular order, it will be understood that the method 1200 is not so limited and can be performed in various orders and include other intervening steps not shown and described herein.

The method 1200 includes engaging 1202 inputs (e.g., first and second articulation input pucks 402, 404) of the articulation subsystem 400 such that the inputs, through the various other components of the articulation subsystem 400, provide opposing forces on each other. For example, if the articulation subsystem 400 includes two racks 414, 418, the method 1200 can include turning the first articulation input puck 402 and the second articulation input puck 404 in opposite directions. On the other hand, if the articulation subsystem 400 includes a single rack 514, the method 1200 can include turning the first articulation input puck 402 and the second articulation input puck 404 in the same direction. By turning the first articulation input puck 402 and the second articulation input puck 404 in directions to cause opposing forces on each other, the control device 1110 can detect when the gears of the articulation subsystem 400 have bottomed out (e.g., via torque sensors, force sensors, or other suitable sensors) and the first articulation input puck 402 and the second articulation input puck 404 can engage with the corresponding pucks of the robotic arm 1100 and the sterile adapter. Stated otherwise, the method 1200 can include rotating a first input puck and a second input puck of the robotic 1100 arm until a predetermined threshold indicator on both the first input puck and the second input puck is detected, the first input puck and the second input puck being in mechanical communication with an articulation subsystem of the surgical instrument. The threshold indicator, for example, can be a threshold force, a threshold current, a threshold voltage, or other similar indicator.

The method 1200 includes turning 1204 the first articulation input puck 402 and the second articulation input puck 404 to relieve torque and moving 1206 the first articulation input puck 402 and the second articulation input puck 404 to a predetermined articulation home position.

The method 1200 includes turning 1208 the first closure puck 202 and the second closure puck 204 until the control device 1110 determines that the closure subsystem 200 has encountered a hard stop (e.g., the anvil 152 is fully closed). Stated otherwise, the method 1200 can include rotating one or more pucks of the closure subsystem until a second predetermined threshold indicator is detected. The threshold indicator, for example, can be a threshold force, a threshold current, a threshold voltage, or other similar indicator. In doing so, the first closure puck 202 and the second closure puck 204 engage with the corresponding pucks of the robotic arm 1100 and the sterile adapter and the control device 1110 will be able to determine the position of the first closure puck 202 and the second closure puck 204. The method 1200 includes regulating 1210 the torque by causing the first closure puck 202 and the second closure puck 204 to rotate only to a predetermined force (e.g., as detected by torque sensors, force sensors, or other suitable sensors) and moving 1212 the closure subsystem 200 to the constant force region 282.

The method 1200 includes moving 1214 the transection puck 802 of the transection subsystem 800 in a retraction direction until a hard stop is detected (e.g., as detected by torque, force, current, or other suitable sensors). The hard stop can be or include a stop at an end of travel of the firing rack 816, a stop feature formed into the knife 166, the distal hard stop 819, or other similar components to determine that the transection subsystem 800 has fully retracted. Stated otherwise, the method 1200 includes rotating an input puck of the transection subsystem until a third predetermined threshold indicator is detected. The threshold indicator, for example, can be a threshold force, a threshold current, a threshold voltage, or other similar indicator. In doing so, the transection puck 802 engages with the corresponding pucks of the robotic arm 1100 and the sterile adapter and the control device 1110 will be able to determine the position of the transection puck 802. The method 1200 includes backing off 1216 or otherwise moving the transection puck 802 in an opposite direction to a predetermined transection home position. As will be appreciated, determining the home position of the transection subsystem 800 while the closure subsystem 200 is in the constant force region 282 can help to ensure the home position of the transection subsystem 800 is determined while the surgical instrument 100 is in a clinically relevant position.

Once engaging and homing of the transection subsystem 800 is complete, the method 1200 further includes backing off 1218 or otherwise moving the first closure puck 202 and the second closure puck 204 of the closure subsystem 200 in an opposite direction to a predetermined closure home position.

The method 1200 includes moving 1220 the roll input puck 602 until a hard stop is detected (e.g., as detected by torque, force, or other suitable sensors). Stated otherwise, the method 1200 includes rotating an input puck of the roll subsystem until a predetermined threshold indicator is detected. The threshold indicator, for example, can be a threshold force, a threshold current, a threshold voltage, or other similar indicator. The hard stop, for example, can be or include the housing tab 626 that causes the roll system 600 to stop rotating. In doing so, the roll input puck 602 will engage with the corresponding pucks of the robotic arm 1100 and the sterile adapter and the control device 1110 will be able to determine the position of the roll input puck 602. The method 1200 includes backing off 1222 or otherwise moving the roll input puck 602 in an opposite direction to a predetermined roll home position.

Figure 66:
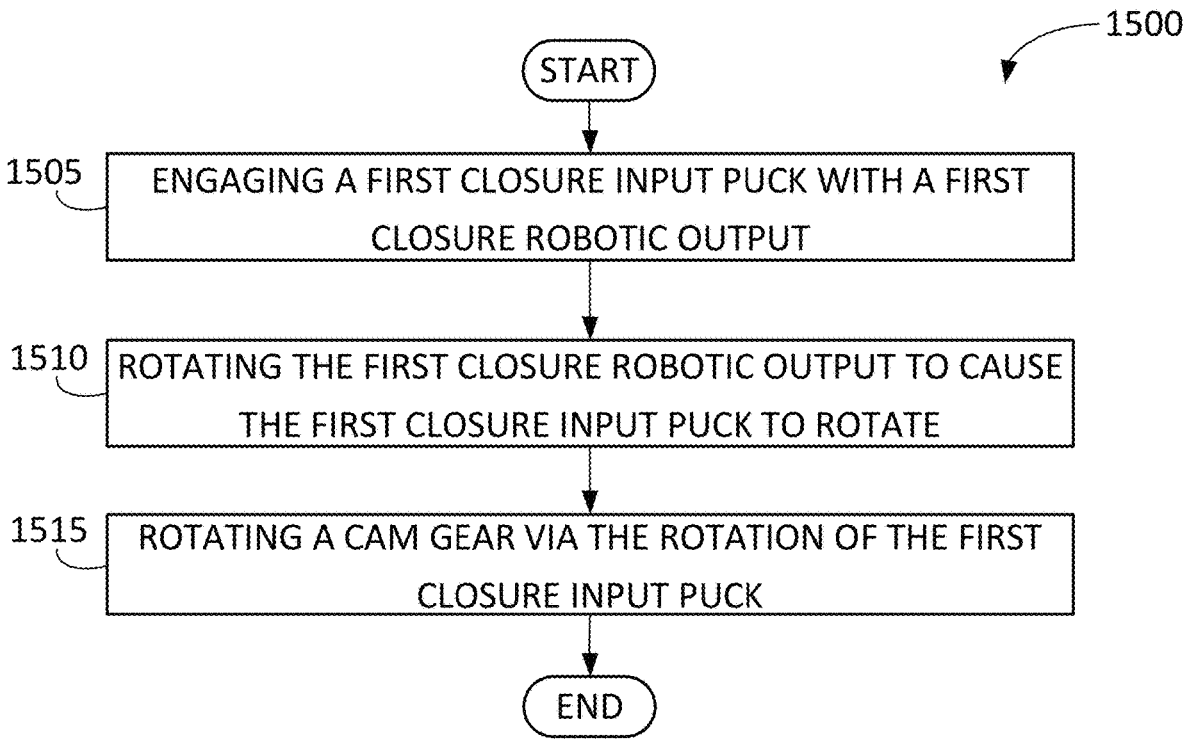
FIG. 66 is a flow chart depicting a method of operating a closure subsystem of a surgical instrument, according to aspects of the present disclosure.

Turning now to FIG. 66, a method 1500 of operating a closure subsystem of a surgical instrument 100 is shown and described. The method 1500 can include engaging 1505 a first closure input puck (e.g., first closure input puck 202) with a first closure robotic output (e.g., first closure robotic output 902). The method 1500 can include rotating 1510 the first closure robotic output to cause the first closure input puck to rotate. The method 1500 can include rotating 1515 a cam gear (e.g., cam gear 210) via the rotation of the first closure input puck. Rotation of the cam gear causes a yoke pin (e.g., yoke pin 216) to track through a cam track (e.g., cam track 214) in the cam gear. The yoke pin is directly or indirectly coupled to a closure tube, as described herein. Tracking of the yoke pin through the cam track causes the yoke pin to translate from a first position to a second position, thereby translating the closure tube. Method 1500 can end after engaging step 1515, or other steps can be performed in accordance with the examples outlined herein.

Any of the closure subsystems 200, articulation subsystems 400, roll subsystems 600, or transection subsystems 800 described herein can be, respectively, substituted by or combined with any of the closure subsystems 200, articulation subsystems 400, roll subsystems 600, or transection subsystems 800 described in U.S. Provisional Application No. 63/515,001 or those described in U.S. Provisional Application No. 63/634,171, both of which are incorporated herein by reference in their entireties. Any of the end effectors 150 described herein can be substituted by or combined with any of the end effectors 150 described in U.S. Provisional Application No. 63/515,001 or those described in U.S. Provisional Application No. 63/634,171, both of which are incorporated herein by reference in their entireties.

CLAUSES

Examples of the present disclosure can be implemented by any of the following numbered clauses:

Clause 1: A closure subsystem (200) for a surgical instrument (100) comprising: a first closure input puck (202) engageable with a first closure robotic output (902); a cam gear (210) rotatably engaged with the first closure input puck (202); and a yoke pin (216) coupled to a closure tube (212) and movable from a first position to a second position in response to a rotation of the cam gear (210), wherein movement of the yoke pin (216) from the first position to the second position translates the closure tube (212) distally onto an anvil ramp (154) of an anvil (152).

Clause 2: The closure subsystem (200) according to Clause 1, wherein the cam gear (210) comprises a cam track (214), and the yoke pin (216) is positioned within the cam track (214).

Clause 3: The closure subsystem (200) according to Clause 2, wherein the cam track (214) comprises a first zone (222) and a second zone (224), wherein rotation of the cam gear (210) provides a non-linear movement profile to the yoke pin (216) through the first zone (222) and the second zone (224).

Clause 4: The closure subsystem (200) according to Clause 3, wherein rotation of the cam gear (210) through the first zone (222) provides faster distal movement of the yoke pin (216) than rotation of the cam gear (210) through the second zone (224), and rotation of the cam gear (210) through the second zone (224) provides a higher mechanical advantage to the yoke pin (216) than rotation of the cam gear (210) through the first zone (222).

Clause 5: The closure subsystem (200) according to Clause 3 or 4, wherein the cam track (214) is polynomial in shape and includes a non-linear portion and a constant radius portion.

Clause 6: The closure subsystem (200) according to Clause 3 or 4, wherein the cam track (214) is a logarithmic spiral.

Clause 7: The closure subsystem (200) according to Clause 1 further comprising a second closure input puck (204) engageable with a second closure robotic output (904), wherein the cam gear (210) is rotatably engaged with the second closure input puck (204).

Clause 8: The closure subsystem (200) according to Clause 7 further comprising a first input rod (203) extending from the first closure input puck (202); a first spur gear (206) positioned on the first input rod (203) and rotatably engaged with the cam gear (210) and turnable by rotation of the first closure input puck (202); a second input rod (205) extending from the second closure input puck (204); and a second spur gear (208) positioned on the second input rod (205) and rotatably engaged with the second closure input puck (204).

Clause 9: The closure subsystem (200) according to Clause 1 further comprising a closure yoke (250), wherein the yoke pin (216) extends from the closure yoke (250) and moves with the yoke pin (216).

Clause 10: The closure subsystem (200) according to Clause 9 further comprising a rotatable shaft (604) disposed within the closure tube (212), the rotatable shaft (604) being rotationally independent of the closure tube (212).

Clause 11: The closure subsystem (200) according to any one of the preceding clauses further comprising a manual closure handle (234) and a manual closure spur gear (230), the manual closure spur gear (230) being turnable by rotation of the manual closure handle (234) and configured to cause rotation of the cam gear (210).

Clause 12: The closure subsystem (200) according to Clause 11, wherein the manual closure handle (234) comprises a manual closure handle grip (236) engaged with the manual closure spur gear (230) and a manual closure handle clip (238) configured to secure the manual closure handle (234) to an enclosure of the surgical instrument (100).

Clause 13: A closure subsystem comprising: a cam gear (210) comprising a cam track (214); and a yoke pin (216)

coupled to a closure tube (212) and movable from a first position to a second position in response to a rotation of the cam gear (210), the yoke pin (216) extending into the cam track (214), wherein the cam track (214) is shaped to provide a non-linear movement profile of the yoke pin (216) and comprises an open position (272), a high-speed compression region (274), a high force region (278), and a constant force region (282), wherein the high-speed compression region (274), the high force region (278), and the constant force region (282) each have different curvatures, and wherein the constant force region (282) is shaped such that the yoke pin (216) remains stationary when tracking through the constant force region (282) as the cam gear (210) rotates.

Clause 14: An articulation subsystem (400) for a surgical instrument (100) comprising: a rotatable shaft (604) having a longitudinal axis (474); a distal channel retainer (408) coupled to an end effector (150), the distal channel retainer (408) being pivotable about an articulation joint (466); a first articulation bushing (426, 526) slidable from a first position to a second position along the longitudinal axis (474) of the rotatable shaft (604); an articulation rod (406) extending distally from the first articulation bushing (426) and coupled at a distal end (472) to the distal channel retainer (408); and a first rack (414, 514) movable with respect to the longitudinal axis (474) of the rotatable shaft (604), wherein movement of the first rack (414, 514) with respect to the longitudinal axis (474) imparts an axial force onto the first articulation bushing (426, 526) moving the first articulation bushing (426, 526) from the first position to the second position, and wherein movement of the first articulation bushing (426) from the first position to the second position actuates the articulation rod (406) causing the distal channel retainer (408) to pivot about the articulation joint (466).

Clause 15: The articulation subsystem (400) according to Clause 14, wherein the first articulation bushing (426) is rotationally independent of the first rack (414).

Clause 16: The articulation subsystem (400) according to Clause 14 or 15 further comprising a first rack gear (434) engaged with the first rack (414, 514), wherein rotation of the first rack gear (434) moves the first rack (414, 514) with respect to the longitudinal axis (474).

Clause 17: The articulation subsystem (400) according to Clause 16 further comprising: a first articulation input puck (402) engageable with a first articulation robotic output (906); a first articulation drive shaft (432) extending from the first articulation input puck (402) and comprising a first drive gear (430); and a first compound gear (442) engaged with the first drive gear (430) and the first rack gear (434), wherein rotation of the first articulation input puck (402) rotates the first rack gear (434) moving the first rack (414, 514) with respect to the longitudinal axis (474).

Clause 18: The articulation subsystem (400) according to Clause 17, wherein the first rack gear (434) is a tube gear, and the first articulation drive shaft (432) is positioned within the first rack gear (434).

Clause 19: The articulation subsystem (400) according to any one of Clauses 14 to 18 further comprising: a second articulation bushing (428) slidable from a third position to a fourth position along the longitudinal axis (474) of the rotatable shaft (604); and a second rack (418, 518) movable with respect to the longitudinal axis (474) of the rotatable shaft (604), movement of the second rack (418, 518) with respect to the longitudinal axis (474) imparts an axial force onto the second articulation bushing (428) to move the second articulation bushing (428) from the third position to the fourth position.

Clause 20: The articulation subsystem (400) according to Clause 19 further comprising a second rack gear (440) engaged with the second rack (418), wherein rotation of the second rack gear (440) moves the second rack (418) with respect to the longitudinal axis (474).

Clause 21: The articulation subsystem (400) according to Clause 20 further comprising: a second articulation input puck (404) engageable with a second articulation robotic output (908); a second articulation drive shaft (438) extending from the second articulation input puck (404) and comprising a second drive gear (436); and a second compound gear (448) engaged with the second drive gear (436) and the second rack gear (440), rotation of the second articulation input puck (404) rotates the second rack gear (440) moving the second rack (418) with respect to the longitudinal axis (474).

Clause 22: The articulation subsystem (400) according to Clause 21, wherein the second rack gear (440) is a tube gear, and the second articulation drive shaft (438) is positioned within the second rack gear (440).

Clause 23: The articulation subsystem (400) according to Clause 20 or 22, wherein movement of the second articulation bushing (428) and the first articulation bushing (426) is antagonistic such that the second articulation bushing (428) is movable by the second rack (418) to translate the first articulation bushing (426) distally along the longitudinal axis (474), and the first articulation bushing (426) is movable by the first rack (414) to translate the second articulation bushing (428) proximally along the longitudinal axis (474).

Clause 24: The articulation subsystem (400) according to any one of Clauses 19 to 23, wherein the second articulation bushing (428) and the first articulation bushing (426) are coupled.

Clause 25: The articulation subsystem (400) according to any one of Clauses 14 to 24 further comprising a first articulation bearing (422, 522), wherein the first rack (414, 514) comprises a first bearing surface (458, 558), and the first articulation bearing (422, 522) is disposed between the first bearing surface (458, 558) and the first articulation bushing (426, 526).

Clause 26: The articulation subsystem (400) according to Clause 25, wherein the first bearing surface (458) is semi-circular.

Clause 27: The articulation subsystem (400) according to Clause 25 or 26, wherein the first rack (414, 514) comprises a first housing track surface (462, 562a, 562b) slidable within a track (176) in an outer housing (102).

Clause 28: The articulation subsystem (400) according to Clause 27, wherein the first housing track surface (462) and the first bearing surface (458) are at 90° with respect to each other.

Clause 29: The articulation subsystem (400) according to any one of Clauses 14 to 28, wherein the articulation rod (406) is slidable through a rod groove (478) in the rotatable shaft (604).

Clause 30: The articulation subsystem (400) according to any one of Clauses 14 to 29, further comprising a first rack gear (434), wherein rotation of the first rack gear (434) causes the movement of the first rack (414, 514).

Clause 31: The articulation subsystem (400) according to Clause 30, wherein the first rack gear (434) comprises first gear teeth (446), wherein the first rack (414, 514) comprises first rack gearing (416, 516), and wherein the first gear teeth (446) are configured to engage with the first rack gearing (416, 516).

Clause 32: The articulation subsystem (400) according to Clause 31, wherein the first rack (514) is positioned between the first rack gear (434) and the rotatable shaft (604).

Clause 33: The articulation subsystem (400) according to Clause 31, wherein the first rack gear (434) is positioned between the first rack (414) and the rotatable shaft (604).

Clause 34: The articulation subsystem (400) according to any one of Clauses 30-33 further comprising: a second rack (418, 518) movable with respect to the longitudinal axis (474) of the rotatable shaft (604); and a second rack gear (440), wherein rotation of the second rack gear (440) causes the movement of the second rack (418, 518).

Clause 35: The articulation subsystem (400) according to Clause 34, wherein the second rack gear (440) comprises second gear teeth (452), wherein the second rack (418, 518) comprises second rack gearing (420, 520), and wherein the second gear teeth (452) are configured to engage with the second rack gearing (420, 520).

Clause 36: The articulation subsystem (400) according to Clause 34, wherein the second rack (518) is positioned between the second rack gear (440) and the rotatable shaft (604).

Clause 37: The articulation subsystem (400) according to Clause 34, wherein the second rack gear (440) is positioned between the second rack (418) and the rotatable shaft (604).

Clause 38: An articulation subsystem (400) for a surgical instrument (100) comprising: a rotatable shaft (604) having a longitudinal axis (474); an articulation rod (406) extending along the longitudinal axis (474) of the rotatable shaft (604) and being rotationally coupled to the rotatable shaft (604); a first articulation bushing (426, 526) slidable from a first position to a second position along the longitudinal axis (474) of the rotatable shaft (604), the first articulation bushing (426, 526) being rotationally coupled to the rotatable shaft (604); a first rack (414, 514) movable with respect to the longitudinal axis (474) of the rotatable shaft (604), the first rack (414, 514) being rotationally independent of the rotatable shaft (604) and the first articulation bushing (426, 526); and a first rack gear (434) engaged with the first rack (414, 514), wherein rotation of the first rack gear (434) moves the first rack (414, 514) with respect to the longitudinal axis (474), and wherein movement of the first rack (414, 514) with respect to the longitudinal axis (474) imparts an axial force onto the first articulation bushing (426, 526) moving the first articulation bushing (426, 526) from the first position to the second position.

Clause 39: The articulation subsystem (400) according to Clause 38, further comprising a first rack gear (434), wherein rotation of the first rack gear (434) causes the movement of the first rack (414, 514).

Clause 40: The articulation subsystem (400) according to Clause 38 or 39 further comprising: a second rack (418, 518) movable with respect to the longitudinal axis (474) of the rotatable shaft (604); and a second rack gear (440), wherein rotation of the second rack gear (440) causes the movement of the second rack (418, 518).

Clause 41: The articulation subsystem (400) according to Clause 40, wherein the second rack gear (440) comprises second gear teeth (452), wherein the second rack (418, 518) comprises second rack gearing (420, 520), and wherein the second gear teeth (452) are configured to engage with the second rack gearing (420, 520).

Clause 42: The articulation subsystem (400) according to Clause 40 or 41, wherein the second rack (518) is positioned between the second rack gear (440) and the rotatable shaft (604).

Clause 43: The articulation subsystem (400) according to Clause 40 or 41, wherein the second rack gear (440) is positioned between the second rack (418) and the rotatable shaft (604).

Clause 44: The articulation subsystem (400) according to Clause 40, wherein the first rack (514) and the second rack (514) abut to form a hollow cylinder.

Clause 45: The articulation subsystem (400) according to Clause 40, wherein the second rack gear (440) comprises second gear teeth (452), wherein the first rack (514) comprises second rack gearing (520), and wherein the second gear teeth (452) are configured to engage with the second rack gearing (520).

Clause 46: The articulation subsystem (400) according to Clause 45, wherein the second rack gearing (520) is positioned diametrically opposite the first rack gearing (516) on a surface of the first rack (514).

Clause 47: The articulation subsystem (400) according to any one of Clauses 38 to 46, wherein the first rack (514) is a cylindrical component comprising a lumen (530) extending through, wherein the first articulation bushing (526) is positioned within the lumen (530).

Clause 48: The articulation subsystem (400) according to Clause 47, wherein the first articulation bushing (526) comprises a distal flange (528), and the first rack (514) is axially constrained distally by the distal flange (528).

Clause 49: The articulation subsystem (400) according to Clause 48, wherein the first articulation bushing (526) is axially constrained proximally by a locking ring (568).

Clause 50: A roll subsystem (600) for a surgical instrument (100) comprising: a rotatable shaft (604); a first roll input puck (602) engageable with a roll robotic output; a worm gear (608) coupled to and rotatable by the first roll input puck (602); and a worm follower (610) coupled to the rotatable shaft (604), wherein rotation of the first roll input puck (602) causes the worm gear (608) to rotate the worm follower (610) and thereby roll the rotatable shaft (604).

Clause 51: The roll subsystem (600) according to Clause 50 further comprising a roll stop bushing (618) engaged with the rotatable shaft (604) and comprising a stop (620).

Clause 52: The roll subsystem (600) according to Clause 51 further comprising an outer housing (102) comprising a housing tab (626), the stop (620) contactable with the housing tab (626) providing a degree of rotation for the rotatable shaft (604).

Clause 53: The roll subsystem (600) according to Clause 52 further comprising a follower bushing (622) comprising a follower bushing stop (624), the follower bushing stop (624) contactable with the stop (620) providing the degree of rotation for the rotatable shaft (604).

Clause 54: The roll subsystem (600) according to any of Clauses 50 to 53 further comprising: a stabilization plate (612); a roll bearing (614); and roll bearing plate (616).

Clause 55: The roll subsystem (600) according to any one of Clause 50 to 54, wherein the first roll input puck (602) comprises an input shaft (605) extending at least partially through the worm gear (608), the input shaft (605) comprising a flat section (772) positioned to correspond to a worm drive flat (770) of the worm gear (608).

Clause 56: The roll subsystem (600) according to any one of Clause 50 to 55, wherein the worm follower (610) comprises a first anti-backlash feature (756, 762, 766), wherein the rotatable shaft (604) comprises a second anti-backlash feature (758, 764, 768), and wherein the first anti-backlash feature (756, 762, 766) is configured to engage with the second anti-backlash feature (758, 764, 768).

Clause 57: The roll subsystem (600) according to any one of Clause 50 to 56, wherein the worm follower (610) comprises a first gear flat (756A), the rotatable shaft (604) comprises a first shaft flat (758A), and the first gear flat (756A) is configured to engage with the first shaft flat (758A) to reduce backlash as the worm gear (608) actuates the worm follower (610).

Clause 58: The roll subsystem (600) according to Clause 57, wherein the worm follower (610) comprises a second gear flat (756B), the rotatable shaft (604) comprises a second shaft flat (758B), and wherein the second gear flat (756B) is configured to engage with the second shaft flat (758B) to reduce backlash as the worm gear (608) actuates the worm follower (610).

Clause 59: The roll subsystem (600) according to Clause 57 or 58, wherein first shaft flat (758A) comprises a rod groove (478) sized to accept an articulation rod (406) therethrough.

Clause 60: The roll subsystem (600) according to any one of Clauses 57 to 59, wherein a first end of the first gear flat (756A) is rounded and inwardly turned so as to come to a singular point (760), a first end of the second gear flat (756B) is rounded and inwardly turned so as to come to the singular point (760), and wherein the singular point (760) contacts the rotatable shaft (604).

Clause 61: The roll subsystem (600) according to Clause 60, wherein a portion of the worm follower (610) between the first gear flat (756A) and the singular point (760) is separated from the rotatable shaft (604) by a first gap (761A), and wherein a portion of the worm follower (610) between the second gear flat (756B) and the singular point (760) is separated from the rotatable shaft (604) by a second gap (761B).

Clause 62: The roll subsystem (600) according to any one of Clause 50 to 61, wherein the worm follower (610) comprises a first key (792), the rotatable shaft (604) comprises a first keyway (764), and first key (792) is configured to engage with the first keyway (764) to reduce backlash as the worm gear (608) actuates the worm follower (610).

Clause 63: The roll subsystem (600) according to any one of Clause 50 to 62, wherein the worm follower (610) comprises a first key (792), the rotatable shaft (604) comprises a first keyway (764), and the first key (792) is configured to engage with the first keyway (764) to reduce backlash as the worm gear (608) actuates the worm follower (610).

Clause 64: The roll subsystem (600) according to any one of Clause 50 to 63, wherein: the worm follower (610) has a first portion with a first wall thickness (767A) and a second portion with a second wall thickness (767B), the first wall thickness (767A) being thicker than the second wall thickness (767B) thereby forming a gear step (766); the rotatable shaft (604) has a first portion with a first wall thickness (769A) and a second portion with a second wall thickness (769B), the first wall thickness (769A) being thicker than the second wall thickness (769B) thereby forming a shaft step (768); and the gear step (766) is configured to engage with the shaft step (768) to reduce backlash as the worm gear (608) actuates the worm follower (610).

Clause 65: The roll subsystem (600) according to any one of Clause 50 to 64 further comprising a thrust block (712) positioned distal to the worm follower (610), the thrust block (712) engaging at least a portion of a housing (102).

Clause 66: The roll subsystem (600) according to Clause 65, wherein the thrust block (712) has a thickness of greater than 1.0 cm.

Clause 67: A transection subsystem (800) for a surgical instrument (100) comprising: a rotatable shaft (604) having a lumen (606); a firing rod (820) extending at least partially through the lumen (606); a firing rack (816) coupled to a proximal end of the firing rod (820) such that the firing rod (820) is rotationally independent of the firing rack (816); and a firing gear (814) engaged with the firing rack (816), wherein rotation of the firing gear (814) moves the firing rack (816) and the firing rod (820) axially.

Clause 68: The transection subsystem (800) according to Clause 67 further comprising a transection input puck (802) engageable with a first transection robotic output, wherein rotation of the firing gear (814) is dependent on rotation of the transection input puck (802).

Clause 69: The transection subsystem (800) according to Clause 68 further comprising: a transection drive shaft (804) coupled to the transection input puck (802); a transection spur gear (806) coupled to the transection drive shaft (804); a transection ramp gear (808) engaged with the transection spur gear (806); a ramp gear shaft (810) coupled to the transection ramp gear (808); and a speed gear (812) engaged with the ramp gear shaft (810).

Clause 70: The transection subsystem (800) according to any one of Clauses 67 to 69, wherein: the firing rack (816) comprise a slot (824); the firing rod (820) comprises a T-shaped tab (822); and the T-shaped tab (822) is engaged with the slot (824) to enable rotation of the firing rod (820) while maintaining a longitudinal connection.

Clause 71: The transection subsystem (800) according to any one of Clauses 67 to 70 further comprising: a key receiver (830) in mechanical communication with the firing gear (814); and a key (836) configured to engage with the key receiver (830), wherein rotating the key (836) when engaged with the key receiver (830) causes the key receiver (830) and the firing gear (814) to rotate, thereby moving the firing rod (820) axially.

Clause 72: The transection subsystem (800) according to Clause 71, the key receiver (830) comprising one or more unidirectional ramps (831); and the key (836) comprising one or more corresponding unidirectional ramps configured to engage with the unidirectional ramps in a first direction and to slide along the unidirectional ramps in a second direction.

Clause 73: The transection subsystem (800) according to Clause 72, further comprising a spring (880) configured to permit the key receiver 830 to move away from the key (836) when the key (836) is rotated in the second direction.

Clause 74: The transection subsystem (800) according to any one of Clauses 71 to 73, the key (836) comprising one or more locking tabs (839) configured to attach the key (836) to the key receiver (830).

Clause 75: The transection subsystem (800) according to Clause 71, the key comprising threads (840) configured to engage with a housing (102) of the surgical instrument (100).

Clause 76: The transection subsystem (800) according to Clause 75, wherein, when the key (836) is turned in a first direction, the threads (840) cause the key (836) to move toward the key receiver (830) and, when the key (836) is turned in a second direction, the threads (840) cause the key (836) to move away from the key receiver (830).

Clause 77: The transection subsystem (800) according to any one of Clauses 71-76 further comprising a tether (844) attached to the key (836) and a housing 102 of the surgical instrument (100).

Clause 78: The transection subsystem (800) according to Clause 71, wherein the key (836) comprises a cam surface (850) and the key receiver (830) comprises a spline (852) configured to engage with the cam surface.

Clause 79: The transection subsystem (800) according to Clause 71, wherein the key (836) comprises a cam surface (850) and the key receiver (830) comprises a protrusion (892) configured to engage with the cam surface.

Clause 80: A housing (102) for a surgical instrument (100) configured to engage with a robotic arm, the housing comprising: a first opening (1029) positioned to be engaged with at least a portion of a robotic arm; a second opening (1035) positioned proximate a rod (212, 604) extending from within the housing; and a fluid management system positioned within the housing (102) proximate one of the first opening (1029) or the second opening (1035), the fluid management system being configured to hold or divert fluid within the housing (102).

Clause 81: The housing (102) according to Clause 80, wherein the fluid management system comprises one or more walls (1004) forming a cavity (1002) within the housing (102) to hold or divert the fluid.

Clause 82: The housing (102) according to Clause 81, further comprising an absorbent (1006) positioned within the cavity (1002).

Clause 83: The housing (102) according to Clause 82, wherein the one or more walls (1004) comprises a retention feature (1008) configured to secure the absorbent (1006) within the cavity (1002).

Clause 84: The housing (102) according to Clause 83, wherein the retention feature (1008) is a rounded undercut positioned such that the absorbent (1006) rests between the retention feature (1008) and an interior surface (1000) of the housing (102).

Clause 85: The housing (102) according to Clause 83, wherein the retention feature (1008) is a one-way-ramp undercut positioned such that the absorbent (1006) rests between the retention feature (1008) and an interior surface (1000) of the housing (102).

Clause 86: The housing (102) according to Clause 83, wherein the retention feature (1008) is a barb positioned on an interior surface (1000) of the housing (102).

Clause 87: The housing (102) according to Clause 83, wherein the retention feature (1008) is a pin, and the absorbent (1006) comprises an aperture (1007) sized to accept the pin therethrough.

Clause 88: The housing (102) according to Clause 83, wherein the retention feature (1008) is a rivet positioned to attach the absorbent (1006) to an interior surface (1000) of the housing (102).

Clause 89: The housing (102) according to Clause 80, wherein the fluid management system comprises a fluid diverter (1030) positioned proximate the first opening (1029).

Clause 90: The housing (102) according to Clause 89, wherein the fluid management system further comprises one or more walls (1004) forming a cavity (1002) within the housing (102) to hold or divert the fluid, and wherein the fluid diverter (1030) comprises a channel (1032) configured to divert fluid into the cavity (1002).

Clause 91: The housing (102) according to Clause 90, further comprising an absorbent (1006) positioned within the cavity (1002).

Clause 92: The housing (102) according to any one of Clauses 89 to 91 further comprising a delatching body (1028) positioned within a delatch opening (1029) of the housing (102).

Clause 93: The housing (102) according to Clause 92, further comprising a release button (104) connected to the delatching body (1028) by a release hinge (1026), wherein the delatching body (1028) is configured to be actuated by the release button (104).

Clause 94: The housing (102) according to Clause 93, wherein the fluid diverter (1030) comprises an elastomeric material and is configured to stretch with the delatching body (1028).

Clause 95: The housing (102) according to any one of Clauses 80 to 94 further comprising a nose (1034) positioned proximate the rod (212, 604), wherein the fluid management system comprises a shaft bushing (1038) surrounding the rod (212, 604), and engaging with the nose (1034).

Clause 96: The housing (102) according to any one of the preceding clauses further comprising a nose (1034) positioned proximate the rod (212, 604), wherein the fluid management system comprises an absorbent ring positioned proximate the nose (1034).

Clause 97: The housing (102) according to any one of Clauses 80 to 96, wherein the surgical instrument (100) further comprises a knife insert retainer (838), wherein the rod (604) comprises a slot (824), the knife insert retainer (838) comprising an elastomeric seal extension (1044) extending into the slot (824).

Clause 98: The housing (102) according to any one of Clauses 80 to 97, wherein the fluid management system comprises a sleeve (1012) surrounding the rod (212, 604), the sleeve comprising an absorbent material.

Clause 99: The housing (102) according to Clause 98, wherein the sleeve (1014) is connected to the housing (102) by a sinching plate (1014).

Clause 100: The housing (102) according to any one of the preceding clauses, wherein the fluid management system comprises a collar (1016, 1024) surrounding the rod (212, 604).

Clause 101: The housing (102) according to Clause 100, wherein the collar (1016) comprises a trap (1018) to pool fluid therein.

Clause 102: The housing (102) according to Clause 100, wherein the collar (1024) comprises a plurality of traps (1025) to pool fluid therein.

Clause 103: A surgical instrument (100) comprising: a housing (102); a closure subsystem (200) disposed within the housing (102), the closure subsystem (200) engaged with a shaft (604); an articulation subsystem (400) movable along the shaft (604) and independently of the closure subsystem (200); and a fluid management system positioned between the closure subsystem (200) and the articulation subsystem (400) and in contact with the shaft (604).

Clause 104: The surgical instrument (100) according to Clause 103, wherein the fluid management system comprises a sleeve (1012) surrounding the shaft (604), the sleeve (1012) comprising an absorbent material.

Clause 105: The surgical instrument (100) according to Clause 104, wherein the sleeve (1012) is connected to the housing (102) by a sinching plate (1014).

Clause 106: The surgical instrument (100) according to Clause 103 or 104, wherein the fluid management system comprises a collar (1016, 1024) surrounding the shaft (604).

Clause 107: The surgical instrument (100) according to Clause 106, wherein the collar (1016) comprises a trap (1018) to pool fluid therein.

Clause 108: The surgical instrument (100) according to Clause 106, wherein the collar (1024) comprises a plurality of traps (1025) to pool fluid therein.

Clause 109: The surgical instrument (100) according to Clause 108, wherein the collar (1016) is attached at a first end to the closure subsystem (200) and at a second end to the articulation subsystem (400).

Clause 110: The surgical instrument (100) according to Clause 109, comprising the closure subsystem (200) of any one of Clauses 1 to 13 and the articulation subsystem (400) of any one of Clauses 14 to 49.

Clause 111: A method comprising: attaching a surgical instrument to a robotic arm; rotating a first input puck and a second input puck of the robotic arm until a predetermined threshold force on both the first input puck and the second input puck is detected, the first input puck and the second input puck being in mechanical communication with an articulation subsystem of the surgical instrument; and rotating the first input puck and the second input puck to a predetermined articulation home position.

Clause 112: The method according to Clause 111 further comprising: rotating a third input puck until a second predetermined threshold force is detected, the third input puck being in mechanical communication with a closure subsystem of the surgical instrument; and rotating the third input puck until the closure subsystem is in a constant clamp region of the closure subsystem.

Clause 113: The method according to Clause 111 or 112 further comprising: rotating a fourth input puck until a third predetermined threshold force is detected, the fourth input puck being in mechanical communication with a transection subsystem of the surgical instrument; and rotating the fourth input puck to a predetermined transection home position.

Clause 114: The method according to Clause 113 further comprising: rotating the third input puck to a predetermined closure home position.

Clause 115: The method according to any one of Clauses 111 to 114 further comprising: rotating a fifth input puck until a fourth predetermined threshold force is detected, the fifth input puck being in mechanical communication with a roll subsystem of the surgical instrument; and rotating the fifth input puck to a predetermine roll home position.

Clause 116: A surgical instrument (100) comprising: the articulation subsystem (400) according to any one of Clauses 14 to 49; and the closure subsystem (200) according to any one of Clauses 1 to 13.

Clause 117: A surgical instrument (100) comprising: the closure subsystem (200) according to any one of Clauses 1 to 13; and the roll subsystem (600) according to any one of Clauses 50 to 66.

Clause 118: A surgical instrument (100) comprising: the closure subsystem (200) according to any one of Clauses 1 to 13; and the transection subsystem (800) according to any one of Clauses 67 to 79.

Clause 119: A surgical instrument (100) comprising: the articulation subsystem (400) according to any one of Clauses 14 to 49; and the roll subsystem (600) according to any one of Clauses 50 to 66.

Clause 120: A surgical instrument (100) comprising: the articulation subsystem (400) according to any one of Clauses 14 to 49; and the transection subsystem (800) according to any one of Clauses 67 to 79.

Clause 121: A surgical instrument (100) comprising: the roll subsystem (600) according to any one of Clauses 50 to 66; and the transection subsystem (800) according to any one of Clauses 67 to 79.

Clause 122: A surgical instrument (100) comprising: the closure subsystem (200) according to any one of Clauses 1 to 13; the articulation subsystem (400) according to any one of Clauses 14 to 49; the roll subsystem (600) according to any one of Clauses 50 to 66; and the transection subsystem (800) according to any one of Clauses 67 to 79.

Clause 123: A method of operating a closure subsystem (200) of a surgical instrument (100), the method comprising: engaging a first closure input puck (202) with a first closure robotic output (902); rotating the first closure robotic output (902) to cause the first closure input puck (202) to rotate; and rotating a cam gear (210) via the rotation of the first closure input puck (202); wherein rotation of the cam gear (210) causes a yoke pin (216) to track through a cam track (214) in the cam gear (210), the yoke pin (216) being directly or indirectly coupled to a closure tube (212), and wherein tracking of the yoke pin (216) through the cam track (214) causes the yoke pin (216) to translate from a first position to a second position, thereby translating the closure tube (212).

Clause 124: The method of Clause 123 further comprising rotating the first closure robotic output (902) until a predetermined threshold indictor is detected.

Clause 125: The method of Clause 124 further comprising rotating the first closure robotic output (902) to a predetermined home position, the predetermined home position being based at least in part on detecting the predetermined threshold indictor.

Clause 126: The method of Clause 124 or 125, wherein the predetermined threshold indicator comprises a threshold force.

Clause 127: The method of Clause 124 or 125, wherein the predetermined threshold indicator comprises a threshold current.

Clause 128: The method of Clause 124 or 125, wherein the predetermined threshold indicator comprises a threshold voltage.

Clause 129: The method of any of the preceding Clauses further comprising: engaging a second closure input puck (204) with a second closure robotic output (904); rotating the second closure robotic output (904) to cause the second closure input puck (204) to rotate; and rotating the cam gear (210) via the rotation of the second closure input puck (204).

Clause 130: The method of Clause 129 further comprising: rotating a first spur gear (206) via rotation of the first closure input puck (202), the first spur gear (206) rotating in a same direction as the first closure input puck (202); and rotating a second spur gear (208) via rotation of the second closure input puck (204), the second spur gear (208) rotating in a same direction as the second closure input puck (204).

Clause 131: The method of Clause 130, wherein: the first spur gear (206) is rotatably engaged with the cam gear (210); and the second closure input puck (204) is rotatably engaged with the cam gear (210).

Clause 133: The method of any one of Clauses 130 to 131, wherein the second spur gear (208) and the first spur gear (206) are configured to rotate concurrently to share a mechanical load for distal translation of the yoke pin (216).

Clause 132: The method of Clause 130 or 132, wherein the second spur gear (208) rotates in an opposite direction of the first spur gear (206).

Clause 134: The method of any one of any one of the preceding Clauses, wherein movement of the yoke pin (216) from the first position to the second position translates the closure tube (212) distally onto an anvil ramp (154) of an anvil (152).

Clause 135: The method of Clause 134 further comprising clamping tissue between the anvil (152) and a cartridge (120) of an end effector (150).

Clause 136: The method of any one of any one of the preceding Clauses, wherein the cam track (214) comprises an open position (272), a high-speed compression region (274), a high force region (278), and a constant force region (282).

Clause 137: The method of Clause 136, wherein the high-speed compression region (274), the high force region (278), and the constant force region (282) each have different curvatures.

Clause 138: The method of Clause 137, wherein the constant force region (282) is shaped such that the yoke pin (216) remains stationary when tracking through the constant force region (282) as the cam gear (210) rotates.

Clause 139: The method of Clause 123, wherein the cam track (214) comprises a first zone (222) and a closure zone (224).

Clause 140: The method of Clause 139, wherein rotation of the cam gear (210) through the first zone (222) provides faster distal movement of the yoke pin (216) than rotation of the cam gear (210) through the closure zone (224), and rotation of the cam gear (210) through the closure zone (224) provides a greater mechanical advantage to the yoke pin (216) than rotation of the cam gear (210) through the first zone (222).

Clause 141: The method of Clause 139 or 140, wherein the cam track (214) is polynomial in shape and includes a non-linear portion and a constant radius portion.

Clause 142: The method of any one of Clauses 139 to 141, wherein the cam track (214) is a logarithmic spiral.

The invention is not necessarily limited to the examples described, which can be varied in construction and detail. The terms "distal" and "proximal" are used throughout the preceding description and are meant to refer to a positions and directions relative to attachment to a robotic arm. As such, "distal" or distally" refer to a position distant to or a direction away from the robotic arm (i.e., a direction toward a patient). Similarly, "proximal" or "proximally" refer to a position near or a direction towards the robotic arm. Furthermore, the singular forms "a," "an," and "the" include plural referents unless the context clearly dictates otherwise. Furthermore, the use of "couple", "coupled", or similar phrases should not be construed as being limited to a certain number of components or a particular order of components unless the context clearly dictates otherwise.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g., "about 90%" may refer to the range of values from 71% to 99%.

Use of the term "transection" or "transection subsystem" is not intended to be limiting to any particular method of use for the components being described. The term "transection" is used since the exemplary embodiments shown in the figures include a knife 166 that transects tissue as it is fired, whereas the same feature can also be used to drive the staples 126. Some implementations may not include a knife 166 at the end, and thus the system may be for stapling alone. The subsystems described herein, including the transection subsystem, can be effective in those staple-only examples as well. Accordingly, the term "transection" and "transection subsystem" can be understood to mean a firing, or driving, of the components of the end effector, whether those components be a knife, a staple, or both.

In describing example embodiments, terminology has been resorted to for the sake of clarity. As a result, not all possible combinations have been listed, and such variants are often apparent to those of skill in the art and are intended to be within the scope of the claims which follow. It is intended that each term contemplates its broadest meaning as understood by those skilled in the art and includes all technical equivalents that operate in a similar manner to accomplish a similar purpose without departing from the scope and spirit of the invention. It is also to be understood that the mention of one or more steps of a method does not preclude the presence of additional method steps or intervening method steps between those steps expressly identified. Similarly, some steps of a method can be performed in a different order than those described herein without departing from the scope of the disclosed technology.

What is claimed is:

1. A method of operating a closure subsystem of a surgical instrument, the method comprising:

engaging a first closure input puck with a first closure robotic output;

rotating the first closure robotic output to cause the first closure input puck to rotate, and continuing to rotate the first closure robotic output until a predetermined threshold indicator is detected;

rotating a cam gear via the rotation of the first closure input puck; and rotating, in response to the predetermined threshold indicator being detected, the first closure robotic output to a predetermined home position, wherein rotation of the cam gear causes a yoke pin to track through a cam track in the cam gear, the yoke pin being directly or indirectly coupled to a closure tube, wherein tracking of the yoke pin through the cam track causes the yoke pin to translate from a first position to a second position, thereby translating the closure tube, wherein the predetermined threshold indicator is detected when the yoke pin is positioned within a constant force region of the cam track; and wherein the yoke pin is positioned at an open position of the cam track when the first closure robotic output is in the predetermined home position.

2. The method of claim 1, wherein the predetermined threshold indicator comprises a threshold force.

3. The method of claim 1, wherein the predetermined threshold indicator comprises a threshold current.

4. The method of claim 1, wherein the predetermined threshold indicator comprises a threshold voltage.

5. The method of claim 1 further comprising:

engaging a second closure input puck with a second closure robotic output;

rotating the second closure robotic output to cause the second closure input puck to rotate; and rotating the cam gear via the rotation of the second closure input puck.

6. The method of claim 5 further comprising:

rotating a first spur gear via rotation of the first closure input puck, the first spur gear rotating in a same direction as the first closure input puck; and rotating a second spur gear via rotation of the second closure input puck, the second spur gear rotating in a same direction as the second closure input puck.

7. The method of claim 6, wherein:

the first spur gear is rotatably engaged with the cam gear; and the second closure input puck is rotatably engaged with the cam gear.

8. The method of claim 7, wherein the second spur gear and the first spur gear are configured to rotate concurrently to share a mechanical load for distal translation of the yoke pin.

9. The method of claim 7, wherein the second spur gear rotates in an opposite direction of the first spur gear.

10. The method of claim 1, wherein movement of the yoke pin from the first position to the second position translates the closure tube distally onto an anvil ramp of an anvil.

11. The method of claim 10 further comprising clamping tissue between the anvil and a cartridge of an end effector.

12. The method of claim 1, wherein the cam track comprises an open position, a high-speed compression region, a high force region, and a constant force region.

13. The method of claim 12, wherein the high-speed compression region, the high force region, and the constant force region each have different curvatures.

14. The method of claim 13, wherein the constant force region is shaped such that the yoke pin remains stationary when tracking through the constant force region as the cam gear rotates.

15. The method of claim 1, wherein the cam track comprises a first zone and a closure zone.

16. The method of claim 15, wherein rotation of the cam gear through the first zone provides faster distal movement of the yoke pin than rotation of the cam gear through the closure zone, and rotation of the cam gear through the closure zone provides a greater mechanical advantage to the yoke pin than rotation of the cam gear through the first zone.

17. A method of operating a closure subsystem of a surgical instrument, the method comprising:

engaging a first closure input puck with a first closure robotic output;

rotating the first closure robotic output in a first direction to rotate the first closure input puck and, via the first closure input puck, a cam gear until a predetermined threshold indicator is detected; and in response to detecting the predetermined threshold indicator, rotating the first closure robotic output in a second direction, opposite the first direction, to a predetermined home position;

wherein rotation of the cam gear causes a yoke pin directly or indirectly coupled to a closure tube to track along a cam track, thereby translating the closure tube;

wherein the predetermined threshold indicator is detected when the yoke pin is within a constant-force region of the cam track; and wherein, when the first closure robotic output is in the predetermined home position, the yoke pin is at an open position of the cam track.

18. The method of claim 17, wherein the predetermined threshold indicator comprises at least one of a threshold force, a threshold current, or a threshold voltage.

* * * * *